US008187606B2

(12) United States Patent
Zhu et al.

(10) Patent No.: US 8,187,606 B2
(45) Date of Patent: May 29, 2012

(54) HPV ANTIGEN FUSION PROTEIN VACCINE COMPOSITIONS AND USES THEREOF

(75) Inventors: Bing Zhu, Beijing (CN); Shifang Yang, Beijing (CN); Junsheng Cui, Beijing (CN)

(73) Assignee: Beijing Sunbio Biotech Co., Ltd., Beijing (CN)

( * ) Notice: Subject to any disclaimer, the term of this patent is extended or adjusted under 35 U.S.C. 154(b) by 191 days.

(21) Appl. No.: 12/446,382

(22) PCT Filed: Oct. 19, 2007

(86) PCT No.: PCT/CN2007/003000
§ 371 (c)(1),
(2), (4) Date: Apr. 20, 2009

(87) PCT Pub. No.: WO2008/049329
PCT Pub. Date: May 2, 2008

(65) Prior Publication Data
US 2010/0158930 A1    Jun. 24, 2010

(30) Foreign Application Priority Data

Oct. 19, 2006 (WO) ................ PCT/CN2006/002778

(51) Int. Cl.
*A61K 39/00* (2006.01)
(52) U.S. Cl. .................... 424/192.1; 530/300; 424/278.1
(58) Field of Classification Search .......................... None
See application file for complete search history.

(56) References Cited

U.S. PATENT DOCUMENTS

2008/0102084 A1* 5/2008 Wu et al. .................... 424/204.1

FOREIGN PATENT DOCUMENTS

| WO | 02/12281 A2 | 2/2002 |
| WO | WO 02/12281 A2 | 2/2002 |
| WO | 2006/081323 A2 | 8/2006 |

OTHER PUBLICATIONS

Cheng et al, Vaccine, 2005, [Available online Nov. 24, 2004] vol. 23, pp. 3864-3874.*
Lin, C.T. et al., "Enhancement of DNA Vaccine Potency Through Linkage of Antigen Gene to ER Chaperne Molecules, ER-60, Tapasin, and Calnexin" *Journal of Biomedical Science* (2005) pp. 279-287, vol. 12.
Zhao, K.J. et al., "Recombined DNA Vaccines Encoding Calreticulin Linked to HPV6bE7 Enhance Immune Response and Inhibit Angiogenic Activity in B16 Melanoma Mouse Model Expressing HPV 6bE7 Antigen" *Archives of Dermatological Research* (2006) pp. 64-72, vol. 298.
Cheng, W.F. et al., "Tumor-Specific Immunity and Antiangiogenesis Generated byu a DNA Vaccine Encoding Calreticulin Linked to a Tumor Antigen" *The Journal of Clinical Investigation* (2001) pp. 669-678, vol. 81(1).
Supplementary European Search Report dated Sep. 15, 2010.
Peng, S. et al., "A combination of DNA vaccines targeting human papillomavirus type 16 E6 and E7 generates potent antitumor effects", Gene Therapy (2006), vol. 13, pp. 257-265.
Cheng, Wen-Fang et al., "Characterization of DNA vaccines encoding the domains of calreticulin for their ability to elicit tumor-specific immunity and antiangiogenesis", Vaccine (2005), vol. 23, pp. 3864-3874.
Kim, JW et al., "Comparison of HPV DNA vaccines employing intracellular targeting strategies", Gene Therapy (2004), vol. 11, pp. 1011-1018.
Cheng, Wen-Fang et al., "Tumor-specific immunity and antiangiogenesis generated by a DNA vaccine encoding calreticulin linked to a tumor antigen", The Journal of Clinical Investigation (2001), vol. 108, No. 5, pp. 669-678.
Peng, Shiwen et al., "Development of a DNA Vaccine Targeting Human Papillomavirus Type 16 Oncoprotein E6", Journal of Virology (2004), vol. 78, No. 16, pp. 8468-8476.
Zhou, Xiaoshan et al., "Efficient Expression of Modified Human Papillomavirus 16 E6/E7 Fusion Protein and the Antitumor Efficacy in a Mouse Model", Biol. Pharm. Bull. (2004), vol. 27, No. 3, pp. 303-307.
Hsieh, Chia-Jung et al., "Enhancement of vaccinia vaccine potency by linkage of tumor antigen gene to gene encoding calreticulin", Vaccine (2004), vol. 22, pp. 3993-4001.
Shi, Wei et al., "Human Papillomavirus Type 16 E7 DNA Vaccine: Mutation in the Open Reading Frame of E7 Enhances Specific Cytotoxic T-Lymphocyte Induction and Antitumor Activity", Journal of Virology (1999), vol. 73, No. 9, pp. 7877-7881.
Smahel, Michal et al., "Modified HPV16 E7 Genes as DNA Vaccine against E7-Containing Oncogenic Cells", Virology (2001), vol. 281, pp. 231-238.
European Office Action dated Sep. 5, 2011 issued in corresponding European Patent Application No. 07816613.9-1223.

* cited by examiner

*Primary Examiner* — Ali R. Salimi
(74) *Attorney, Agent, or Firm* — Scully, Scott, Murphy & Presser, P.C.

(57) ABSTRACT

The present invention provides a fusion protein comprising an immunostimulatory polypeptide and a mutant E7 protein of a human papilloma virus. The present invention also provides a gene encoding the fusion protein, expression vectors containing the gene, a pharmaceutical composition comprising the fusion protein, a method for treating or preventing a human papilloma virus related disease by using the fusion protein and uses of the fusion protein in the preparation of a medicament for the treatment or prevention of the human papilloma virus related disease.

14 Claims, 10 Drawing Sheets

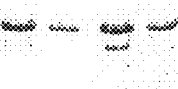
FIG. 1A  C6E7 (Fresh)    1 2 3 4
FIG. 1B  C6E7M2 (Fresh)   1 2 3 4
FIG. 1C  C6E7M3 (Fresh)   1 2 3 4
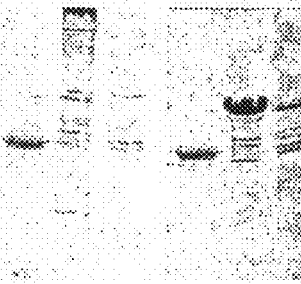
FIG. 1D  Storage: 4°C, 2 months
← Protein Aggregates
← Intact Proteins
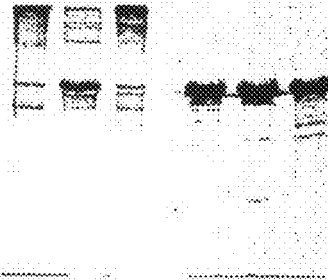
FIG. 1E  Storage: -80°C, 1.5 months
← Protein Aggregates
← Intact Proteins

SEQUENCE LISTING

```
<160> NUMBER OF SEQ ID NOS: 21

<210> SEQ ID NO 1
<211> LENGTH: 98
<212> TYPE: PRT
<213> ORGANISM: Human papillomavirus

<400> SEQUENCE: 1

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro
```

<210> SEQ ID NO 2
<211> LENGTH: 417
<212> TYPE: PRT
<213> ORGANISM: human calreticulin

<400> SEQUENCE: 2

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
            35                  40                  45

Phe Val Leu Ser Ser Gly Lys Phe Tyr Gly Asp Glu Glu Lys Asp Lys
        50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Glu Asp
370                 375                 380
```

Lys Glu Asp Asp Glu Asp Lys Asp Glu Asp Glu Asp Glu Asp
385                 390                 395                 400

Lys Glu Glu Asp Glu Glu Asp Val Pro Gly Gln Ala Lys Asp Glu
                405                 410                 415

Leu

<210> SEQ ID NO 3
<211> LENGTH: 1353
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: CDS
<222> LOCATION: (1)..(1353)

<400> SEQUENCE: 3

```
atg gag cct gcc gtc tac ttc aag gag cag ttt ctg gac gga gac ggg      48
Met Glu Pro Ala Val Tyr Phe Lys Glu Gln Phe Leu Asp Gly Asp Gly
1               5                   10                  15 tgg act tcc cgc tgg atc gaa tcc aaa cac aag tca gat ttt ggc aaa      96
Trp Thr Ser Arg Trp Ile Glu Ser Lys His Lys Ser Asp Phe Gly Lys
            20                  25                  30 ttc gtt ctc agt tcc ggc aag ttc tac ggt gac gag gag aaa gat aaa     144
Phe Val Leu Ser Ser Gly Lys Phe Tyr Gly Asp Glu Glu Lys Asp Lys
        35                  40                  45 ggt ttg cag aca agc cag gat gca cgc ttt tat gct ctg tcg gcc agt     192
Gly Leu Gln Thr Ser Gln Asp Ala Arg Phe Tyr Ala Leu Ser Ala Ser
    50                  55                  60 ttc gag cct ttc agc aac aaa ggc cag acg ctg gtg gtg cag ttc acg     240
Phe Glu Pro Phe Ser Asn Lys Gly Gln Thr Leu Val Val Gln Phe Thr
65                  70                  75                  80 gtg aaa cat gag cag aac atc gac tgt ggg ggc ggc tat gtg aag ctg     288
Val Lys His Glu Gln Asn Ile Asp Cys Gly Gly Gly Tyr Val Lys Leu
                85                  90                  95 ttt cct aat agt ttg gac cag aca gac atg cac gga gac tca gaa tac     336
Phe Pro Asn Ser Leu Asp Gln Thr Asp Met His Gly Asp Ser Glu Tyr
            100                 105                 110 aac atc atg ttt ggt ccc gac atc tgt ggc cct ggc acc aag aag gtt     384
Asn Ile Met Phe Gly Pro Asp Ile Cys Gly Pro Gly Thr Lys Lys Val
        115                 120                 125 cat gtc atc ttc aac tac aag ggc aag aac gtg ctg atc aac aag gac     432
His Val Ile Phe Asn Tyr Lys Gly Lys Asn Val Leu Ile Asn Lys Asp
    130                 135                 140 atc cgt tgc aag gat gat gag ttt aca cac ctg tac aca ctg att gtg     480
Ile Arg Cys Lys Asp Asp Glu Phe Thr His Leu Tyr Thr Leu Ile Val
145                 150                 155                 160 cgg cca gac aac acc tat gag gtg aag att gac aac agc cag gtg gag     528
Arg Pro Asp Asn Thr Tyr Glu Val Lys Ile Asp Asn Ser Gln Val Glu
                165                 170                 175 tcc ggc tcc ttg gaa gac gat tgg gac ttc ctg cca ccc aag aag ata     576
Ser Gly Ser Leu Glu Asp Asp Trp Asp Phe Leu Pro Pro Lys Lys Ile
            180                 185                 190 aag gat cct gat gct tca aaa ccg gaa gac tgg gat gag cgg gcc aag     624
Lys Asp Pro Asp Ala Ser Lys Pro Glu Asp Trp Asp Glu Arg Ala Lys
        195                 200                 205 atc gat gat ccc aca gac tcc aag cct gag gac tgg gac aag ccc gag     672
Ile Asp Asp Pro Thr Asp Ser Lys Pro Glu Asp Trp Asp Lys Pro Glu
    210                 215                 220 cat atc cct gac cct gat gct aag aag ccc gag gac tgg gat gaa gag     720
His Ile Pro Asp Pro Asp Ala Lys Lys Pro Glu Asp Trp Asp Glu Glu
```

```
atg gac gga gag tgg gaa ccc cca gtg att cag aac cct gag tac aag      768
Met Asp Gly Glu Trp Glu Pro Pro Val Ile Gln Asn Pro Glu Tyr Lys
            245                 250                 255 ggt gag tgg aag ccc cgg cag atc gac aac cca gat tac aag ggc act      816
Gly Glu Trp Lys Pro Arg Gln Ile Asp Asn Pro Asp Tyr Lys Gly Thr
        260                 265                 270 tgg atc cac cca gaa att gac aac ccc gag tat tct ccc gat ccc agt      864
Trp Ile His Pro Glu Ile Asp Asn Pro Glu Tyr Ser Pro Asp Pro Ser
    275                 280                 285 atc tat gcc tat gat aac ttt ggc gtg ctg ggc ctg gac ctc tgg cag      912
Ile Tyr Ala Tyr Asp Asn Phe Gly Val Leu Gly Leu Asp Leu Trp Gln
290                 295                 300 gtc aag tct ggc acc atc ttt gac aac ttc ctc atc acc aac gat gag      960
Val Lys Ser Gly Thr Ile Phe Asp Asn Phe Leu Ile Thr Asn Asp Glu
305                 310                 315                 320 gca tac gct gag gag ttt ggc aac gag acg tgg ggc gta aca aag gca     1008
Ala Tyr Ala Glu Glu Phe Gly Asn Glu Thr Trp Gly Val Thr Lys Ala
                325                 330                 335 gca gag aaa caa atg aag gac aaa cag gac gag gag cag agg gtc gac     1056
Ala Glu Lys Gln Met Lys Asp Lys Gln Asp Glu Glu Gln Arg Val Asp
            340                 345                 350 atg cat ggt gat act ccg act ctt cat gaa tat atg ctg gat ctg caa     1104
Met His Gly Asp Thr Pro Thr Leu His Glu Tyr Met Leu Asp Leu Gln
        355                 360                 365 ccg gaa act act gat ctg tac tgt tat gaa caa ctg aat gat agc tct     1152
Pro Glu Thr Thr Asp Leu Tyr Cys Tyr Glu Gln Leu Asn Asp Ser Ser
    370                 375                 380 gaa gag gaa gat gaa att gat ggt cca gct ggt caa gca gaa ccg gat     1200
Glu Glu Glu Asp Glu Ile Asp Gly Pro Ala Gly Gln Ala Glu Pro Asp
385                 390                 395                 400 cgt gct cat tat aat att gta act ttt tgt tgt aaa tgt gat tct act     1248
Arg Ala His Tyr Asn Ile Val Thr Phe Cys Cys Lys Cys Asp Ser Thr
                405                 410                 415 ctg cgt ctg tgt gta caa agc act cat gtt gat att cgt act ctg gaa     1296
Leu Arg Leu Cys Val Gln Ser Thr His Val Asp Ile Arg Thr Leu Glu
            420                 425                 430 gat ctg ctt atg ggt act ctg ggt att gtt tgt ccg att tgt tct cag     1344
Asp Leu Leu Met Gly Thr Leu Gly Ile Val Cys Pro Ile Cys Ser Gln
        435                 440                 445 aaa cca taa                                                          1353
Lys Pro
450
```

<210> SEQ ID NO 4
<211> LENGTH: 450
<212> TYPE: PRT
<213> ORGANISM: Artificial sequence
<220> FEATURE:
<223> OTHER INFORMATION: Synthetic protein construct

<400> SEQUENCE: 4

```
Met Glu Pro Ala Val Tyr Phe Lys Glu Gln Phe Leu Asp Gly Asp Gly
1               5                   10                  15

Trp Thr Ser Arg Trp Ile Glu Ser Lys His Lys Ser Asp Phe Gly Lys
            20                  25                  30

Phe Val Leu Ser Ser Gly Lys Phe Tyr Gly Asp Glu Glu Lys Asp Lys
        35                  40                  45

Gly Leu Gln Thr Ser Gln Asp Ala Arg Phe Tyr Ala Leu Ser Ala Ser
    50                  55                  60
```

```
Phe Glu Pro Phe Ser Asn Lys Gly Gln Thr Leu Val Val Gln Phe Thr
 65                  70                  75                  80
Val Lys His Glu Gln Asn Ile Asp Cys Gly Gly Gly Tyr Val Lys Leu
                 85                  90                  95
Phe Pro Asn Ser Leu Asp Gln Thr Asp Met His Gly Asp Ser Glu Tyr
            100                 105                 110
Asn Ile Met Phe Gly Pro Asp Ile Cys Gly Pro Gly Thr Lys Lys Val
        115                 120                 125
His Val Ile Phe Asn Tyr Lys Gly Lys Asn Val Leu Ile Asn Lys Asp
    130                 135                 140
Ile Arg Cys Lys Asp Asp Glu Phe Thr His Leu Tyr Thr Leu Ile Val
145                 150                 155                 160
Arg Pro Asp Asn Thr Tyr Glu Val Lys Ile Asp Asn Ser Gln Val Glu
                165                 170                 175
Ser Gly Ser Leu Glu Asp Asp Trp Asp Phe Leu Pro Pro Lys Lys Ile
            180                 185                 190
Lys Asp Pro Asp Ala Ser Lys Pro Glu Asp Trp Asp Glu Arg Ala Lys
        195                 200                 205
Ile Asp Asp Pro Thr Asp Ser Lys Pro Glu Asp Trp Asp Lys Pro Glu
    210                 215                 220
His Ile Pro Asp Pro Asp Ala Lys Lys Pro Glu Asp Trp Asp Glu Glu
225                 230                 235                 240
Met Asp Gly Glu Trp Glu Pro Pro Val Ile Gln Asn Pro Glu Tyr Lys
                245                 250                 255
Gly Glu Trp Lys Pro Arg Gln Ile Asp Asn Pro Asp Tyr Lys Gly Thr
            260                 265                 270
Trp Ile His Pro Glu Ile Asp Asn Pro Glu Tyr Ser Pro Asp Pro Ser
        275                 280                 285
Ile Tyr Ala Tyr Asp Asn Phe Gly Val Leu Gly Leu Asp Leu Trp Gln
    290                 295                 300
Val Lys Ser Gly Thr Ile Phe Asp Asn Phe Leu Ile Thr Asn Asp Glu
305                 310                 315                 320
Ala Tyr Ala Glu Glu Phe Gly Asn Glu Thr Trp Gly Val Thr Lys Ala
                325                 330                 335
Ala Glu Lys Gln Met Lys Asp Lys Gln Asp Glu Glu Gln Arg Val Asp
            340                 345                 350
Met His Gly Asp Thr Pro Thr Leu His Glu Tyr Met Leu Asp Leu Gln
        355                 360                 365
Pro Glu Thr Thr Asp Leu Tyr Cys Tyr Glu Gln Leu Asn Asp Ser Ser
    370                 375                 380
Glu Glu Glu Asp Glu Ile Asp Gly Pro Ala Gly Gln Ala Glu Pro Asp
385                 390                 395                 400
Arg Ala His Tyr Asn Ile Val Thr Phe Cys Cys Lys Cys Asp Ser Thr
                405                 410                 415
Leu Arg Leu Cys Val Gln Ser Thr His Val Asp Ile Arg Thr Leu Glu
            420                 425                 430
Asp Leu Leu Met Gly Thr Leu Gly Ile Val Cys Pro Ile Cys Ser Gln
        435                 440                 445
Lys Pro
    450

<210> SEQ ID NO 5
<211> LENGTH: 1353
<212> TYPE: DNA
<213> ORGANISM: Artificial sequence
```

<220> FEATURE:
<223> OTHER INFORMATION: Synthetic nucleic acid sequence
<220> FEATURE:
<221> NAME/KEY: CDS
<222> LOCATION: (1)..(1353)

<400> SEQUENCE: 5

```
atg gag cct gcc gtc tac ttc aag gag cag ttt ctg gac gga gac ggg    48
Met Glu Pro Ala Val Tyr Phe Lys Glu Gln Phe Leu Asp Gly Asp Gly
1               5                   10                  15 tgg act tcc cgc tgg atc gaa tcc aaa cac aag tca gat ttt ggc aaa    96
Trp Thr Ser Arg Trp Ile Glu Ser Lys His Lys Ser Asp Phe Gly Lys
            20                  25                  30 ttc gtt ctc agt tcc ggc aag ttc tac ggt gac gag gag aaa gat aaa   144
Phe Val Leu Ser Ser Gly Lys Phe Tyr Gly Asp Glu Glu Lys Asp Lys
        35                  40                  45 ggt ttg cag aca agc cag gat gca cgc ttt tat gct ctg tcg gcc agt   192
Gly Leu Gln Thr Ser Gln Asp Ala Arg Phe Tyr Ala Leu Ser Ala Ser
    50                  55                  60 ttc gag cct ttc agc aac aaa ggc cag acg ctg gtg gtg cag ttc acg   240
Phe Glu Pro Phe Ser Asn Lys Gly Gln Thr Leu Val Val Gln Phe Thr
65                  70                  75                  80 gtg aaa cat gag cag aac atc gac tgt ggg ggc ggc tat gtg aag ctg   288
Val Lys His Glu Gln Asn Ile Asp Cys Gly Gly Gly Tyr Val Lys Leu
                85                  90                  95 ttt cct aat agt ttg gac cag aca gac atg cac gga gac tca gaa tac   336
Phe Pro Asn Ser Leu Asp Gln Thr Asp Met His Gly Asp Ser Glu Tyr
            100                 105                 110 aac atc atg ttt ggt ccc gac atc tgt ggc cct ggc acc aag aag gtt   384
Asn Ile Met Phe Gly Pro Asp Ile Cys Gly Pro Gly Thr Lys Lys Val
        115                 120                 125 cat gtc atc ttc aac tac aag ggc aag aac gtg ctg atc aac aag gac   432
His Val Ile Phe Asn Tyr Lys Gly Lys Asn Val Leu Ile Asn Lys Asp
    130                 135                 140 atc cgt tgc aag gat gat gag ttt aca cac ctg tac aca ctg att gtg   480
Ile Arg Cys Lys Asp Asp Glu Phe Thr His Leu Tyr Thr Leu Ile Val
145                 150                 155                 160 cgg cca gac aac acc tat gag gtg aag att gac aac agc cag gtg gag   528
Arg Pro Asp Asn Thr Tyr Glu Val Lys Ile Asp Asn Ser Gln Val Glu
                165                 170                 175 tcc ggc tcc ttg gaa gac gat tgg gac ttc ctg cca ccc aag aag ata   576
Ser Gly Ser Leu Glu Asp Asp Trp Asp Phe Leu Pro Pro Lys Lys Ile
            180                 185                 190 aag gat cct gat gct tca aaa ccg gaa gac tgg gat gag cgg gcc aag   624
Lys Asp Pro Asp Ala Ser Lys Pro Glu Asp Trp Asp Glu Arg Ala Lys
        195                 200                 205 atc gat gat ccc aca gac tcc aag cct gag gac tgg gac aag ccc gag   672
Ile Asp Asp Pro Thr Asp Ser Lys Pro Glu Asp Trp Asp Lys Pro Glu
    210                 215                 220 cat atc cct gac cct gat gct aag aag ccc gag gac tgg gat gaa gag   720
His Ile Pro Asp Pro Asp Ala Lys Lys Pro Glu Asp Trp Asp Glu Glu
225                 230                 235                 240 atg gac gga gag tgg gaa ccc cca gtg att cag aac cct gag tac aag   768
Met Asp Gly Glu Trp Glu Pro Pro Val Ile Gln Asn Pro Glu Tyr Lys
                245                 250                 255 ggt gag tgg aag ccc cgg cag atc gac aac cca gat tac aag ggc act   816
Gly Glu Trp Lys Pro Arg Gln Ile Asp Asn Pro Asp Tyr Lys Gly Thr
            260                 265                 270 tgg atc cac cca gaa att gac aac ccc gag tat tct ccc gat ccc agt   864
Trp Ile His Pro Glu Ile Asp Asn Pro Glu Tyr Ser Pro Asp Pro Ser
        275                 280                 285
```

| | | |
|---|---|---|
| atc tat gcc tat gat aac ttt ggc gtg ctg ggc ctg gac ctc tgg cag<br>Ile Tyr Ala Tyr Asp Asn Phe Gly Val Leu Gly Leu Asp Leu Trp Gln<br>290                              295                            300 | | 912 |
| gtc aag tct ggc acc atc ttt gac aac ttc ctc atc acc aac gat gag<br>Val Lys Ser Gly Thr Ile Phe Asp Asn Phe Leu Ile Thr Asn Asp Glu<br>305                            310                            315                        320 | | 960 |
| gca tac gct gag gag ttt ggc aac gag acg tgg ggc gta aca aag gca<br>Ala Tyr Ala Glu Glu Phe Gly Asn Glu Thr Trp Gly Val Thr Lys Ala<br>                            325                            330                        335 | | 1008 |
| gca gag aaa caa atg aag gac aaa cag gac gag cag agg gtc gac<br>Ala Glu Lys Gln Met Lys Asp Lys Gln Asp Glu Gln Arg Val Asp<br>                340                        345                            350 | | 1056 |
| atg cat ggt gat act ccg act ctt cat gaa tat atg ctg gat ctg caa<br>Met His Gly Asp Thr Pro Thr Leu His Glu Tyr Met Leu Asp Leu Gln<br>                          355                            360                        365 | | 1104 |
| ccg gaa act act gat ctg tac tgt tat gaa caa ctg aat gat agc tct<br>Pro Glu Thr Thr Asp Leu Tyr Cys Tyr Glu Gln Leu Asn Asp Ser Ser<br>370                              375                            380 | | 1152 |
| gaa gag gaa gat gaa att gat ggt cca gct ggt caa gca gaa ccg gat<br>Glu Glu Glu Asp Glu Ile Asp Gly Pro Ala Gly Gln Ala Glu Pro Asp<br>385                              390                            395                        400 | | 1200 |
| cgt gct cat tat aat att gta act ttt tgt tct aaa tgt gat tct act<br>Arg Ala His Tyr Asn Ile Val Thr Phe Cys Ser Lys Cys Asp Ser Thr<br>                          405                            410                        415 | | 1248 |
| ctg cgt ctg gtt gta caa agc act cat gtt gat att cgt act ctg gaa<br>Leu Arg Leu Val Val Gln Ser Thr His Val Asp Ile Arg Thr Leu Glu<br>                          420                            425                        430 | | 1296 |
| gat ctg ctt atg ggt act ctg ggt att gtt tgt ccg att tgt tct cag<br>Asp Leu Leu Met Gly Thr Leu Gly Ile Val Cys Pro Ile Cys Ser Gln<br>                          435                            440                        445 | | 1344 |
| aaa cca taa<br>Lys Pro<br>      450 | | 1353 |

```
<210> SEQ ID NO 6
<211> LENGTH: 450
<212> TYPE: PRT
<213> ORGANISM: Artificial sequence
<220> FEATURE:
<223> OTHER INFORMATION: Synthetic protein construct

<400> SEQUENCE: 6
```

Met Glu Pro Ala Val Tyr Phe Lys Glu Gln Phe Leu Asp Gly Asp Gly
1               5                   10                  15

Trp Thr Ser Arg Trp Ile Glu Ser Lys His Lys Ser Asp Phe Gly Lys
            20                  25                  30

Phe Val Leu Ser Ser Gly Lys Phe Tyr Gly Asp Glu Glu Lys Asp Lys
        35                  40                  45

Gly Leu Gln Thr Ser Gln Asp Ala Arg Phe Tyr Ala Leu Ser Ala Ser
    50                  55                  60

Phe Glu Pro Phe Ser Asn Lys Gly Gln Thr Leu Val Val Gln Phe Thr
65                  70                  75                  80

Val Lys His Glu Gln Asn Ile Asp Cys Gly Gly Gly Tyr Val Lys Leu
                85                  90                  95

Phe Pro Asn Ser Leu Asp Gln Thr Asp Met His Gly Asp Ser Glu Tyr
            100                 105                 110

Asn Ile Met Phe Gly Pro Asp Ile Cys Gly Pro Gly Thr Lys Lys Val
        115                 120                 125

His Val Ile Phe Asn Tyr Lys Gly Lys Asn Val Leu Ile Asn Lys Asp
    130                 135                 140

```
Ile Arg Cys Lys Asp Asp Glu Phe Thr His Leu Tyr Thr Leu Ile Val
145                 150                 155                 160
Arg Pro Asp Asn Thr Tyr Glu Val Lys Ile Asp Asn Ser Gln Val Glu
            165                 170                 175
Ser Gly Ser Leu Glu Asp Asp Trp Asp Phe Leu Pro Pro Lys Lys Ile
        180                 185                 190
Lys Asp Pro Asp Ala Ser Lys Pro Glu Asp Trp Asp Glu Arg Ala Lys
    195                 200                 205
Ile Asp Asp Pro Thr Asp Ser Lys Pro Glu Asp Trp Asp Lys Pro Glu
210                 215                 220
His Ile Pro Asp Pro Asp Ala Lys Lys Pro Glu Asp Trp Asp Glu Glu
225                 230                 235                 240
Met Asp Gly Glu Trp Glu Pro Pro Val Ile Gln Asn Pro Glu Tyr Lys
            245                 250                 255
Gly Glu Trp Lys Pro Arg Gln Ile Asp Asn Pro Asp Tyr Lys Gly Thr
        260                 265                 270
Trp Ile His Pro Glu Ile Asp Asn Pro Glu Tyr Ser Pro Asp Pro Ser
    275                 280                 285
Ile Tyr Ala Tyr Asp Asn Phe Gly Val Leu Gly Leu Asp Leu Trp Gln
290                 295                 300
Val Lys Ser Gly Thr Ile Phe Asp Asn Phe Leu Ile Thr Asn Asp Glu
305                 310                 315                 320
Ala Tyr Ala Glu Glu Phe Gly Asn Glu Thr Trp Gly Val Thr Lys Ala
            325                 330                 335
Ala Glu Lys Gln Met Lys Asp Lys Gln Asp Glu Glu Gln Arg Val Asp
        340                 345                 350
Met His Gly Asp Thr Pro Thr Leu His Glu Tyr Met Leu Asp Leu Gln
    355                 360                 365
Pro Glu Thr Thr Asp Leu Tyr Cys Tyr Glu Gln Leu Asn Asp Ser Ser
370                 375                 380
Glu Glu Glu Asp Glu Ile Asp Gly Pro Ala Gly Gln Ala Glu Pro Asp
385                 390                 395                 400
Arg Ala His Tyr Asn Ile Val Thr Phe Cys Ser Lys Cys Asp Ser Thr
            405                 410                 415
Leu Arg Leu Val Val Gln Ser Thr His Val Asp Ile Arg Thr Leu Glu
        420                 425                 430
Asp Leu Leu Met Gly Thr Leu Gly Ile Val Cys Pro Ile Cys Ser Gln
    435                 440                 445
Lys Pro
    450

<210> SEQ ID NO 7
<211> LENGTH: 1353
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: CDS
<222> LOCATION: (1)..(1353)

<400> SEQUENCE: 7 atg gag cct gcc gtc tac ttc aag gag cag ttt ctg gac gga gac ggg      48
Met Glu Pro Ala Val Tyr Phe Lys Glu Gln Phe Leu Asp Gly Asp Gly
1               5                   10                  15 tgg act tcc cgc tgg atc gaa tcc aaa cac aag tca gat ttt ggc aaa      96
Trp Thr Ser Arg Trp Ile Glu Ser Lys His Lys Ser Asp Phe Gly Lys
```

-continued

```
              20                  25                  30
ttc gtt ctc agt tcc ggc aag ttc tac ggt gac gag gag aaa gat aaa     144
Phe Val Leu Ser Ser Gly Lys Phe Tyr Gly Asp Glu Glu Lys Asp Lys
            35                  40                  45 ggt ttg cag aca agc cag gat gca cgc ttt tat gct ctg tcg gcc agt     192
Gly Leu Gln Thr Ser Gln Asp Ala Arg Phe Tyr Ala Leu Ser Ala Ser
 50                  55                  60 ttc gag cct ttc agc aac aaa ggc cag acg ctg gtg gtg cag ttc acg     240
Phe Glu Pro Phe Ser Asn Lys Gly Gln Thr Leu Val Val Gln Phe Thr
 65                  70                  75                  80 gtg aaa cat gag cag aac atc gac tgt ggg ggc ggc tat gtg aag ctg     288
Val Lys His Glu Gln Asn Ile Asp Cys Gly Gly Gly Tyr Val Lys Leu
                 85                  90                  95 ttt cct aat agt ttg gac cag aca gac atg cac gga gac tca gaa tac     336
Phe Pro Asn Ser Leu Asp Gln Thr Asp Met His Gly Asp Ser Glu Tyr
            100                 105                 110 aac atc atg ttt ggt ccc gac atc tgt ggc cct ggc acc aag aag gtt     384
Asn Ile Met Phe Gly Pro Asp Ile Cys Gly Pro Gly Thr Lys Lys Val
        115                 120                 125 cat gtc atc ttc aac tac aag ggc aag aac gtg ctg atc aac aag gac     432
His Val Ile Phe Asn Tyr Lys Gly Lys Asn Val Leu Ile Asn Lys Asp
130                 135                 140 atc cgt tgc aag gat gat gag ttt aca cac ctg tac aca ctg att gtg     480
Ile Arg Cys Lys Asp Asp Glu Phe Thr His Leu Tyr Thr Leu Ile Val
145                 150                 155                 160 cgg cca gac aac acc tat gag gtg aag att gac aac agc cag gtg gag     528
Arg Pro Asp Asn Thr Tyr Glu Val Lys Ile Asp Asn Ser Gln Val Glu
                165                 170                 175 tcc ggc tcc ttg gaa gac gat tgg gac ttc ctg cca ccc aag aag ata     576
Ser Gly Ser Leu Glu Asp Asp Trp Asp Phe Leu Pro Pro Lys Lys Ile
            180                 185                 190 aag gat cct gat gct tca aaa ccg gaa gac tgg gat gag cgg gcc aag     624
Lys Asp Pro Asp Ala Ser Lys Pro Glu Asp Trp Asp Glu Arg Ala Lys
        195                 200                 205 atc gat gat ccc aca gac tcc aag cct gag gac tgg gac aag ccc gag     672
Ile Asp Asp Pro Thr Asp Ser Lys Pro Glu Asp Trp Asp Lys Pro Glu
210                 215                 220 cat atc cct gac cct gat gct aag aag ccc gag gac tgg gat gaa gag     720
His Ile Pro Asp Pro Asp Ala Lys Lys Pro Glu Asp Trp Asp Glu Glu
225                 230                 235                 240 atg gac gga gag tgg gaa ccc cca gtg att cag aac cct gag tac aag     768
Met Asp Gly Glu Trp Glu Pro Pro Val Ile Gln Asn Pro Glu Tyr Lys
                245                 250                 255 ggt gag tgg aag ccc cgg cag atc gac aac cca gat tac aag ggc act     816
Gly Glu Trp Lys Pro Arg Gln Ile Asp Asn Pro Asp Tyr Lys Gly Thr
            260                 265                 270 tgg atc cac cca gaa att gac aac ccc gag tat tct ccc gat ccc agt     864
Trp Ile His Pro Glu Ile Asp Asn Pro Glu Tyr Ser Pro Asp Pro Ser
        275                 280                 285 atc tat gcc tat gat aac ttt ggc gtg ctg ggc ctg gac ctc tgg cag     912
Ile Tyr Ala Tyr Asp Asn Phe Gly Val Leu Gly Leu Asp Leu Trp Gln
290                 295                 300 gtc aag tct ggc acc atc ttt gac aac ttc ctc atc acc aac gat gag     960
Val Lys Ser Gly Thr Ile Phe Asp Asn Phe Leu Ile Thr Asn Asp Glu
305                 310                 315                 320 gca tac gct gag gag ttt ggc aac gag acg tgg ggc gta aca aag gca    1008
Ala Tyr Ala Glu Glu Phe Gly Asn Glu Thr Trp Gly Val Thr Lys Ala
                325                 330                 335 gca gag aaa caa atg aag gac aaa cag gac gag gag cag agg gtc gac    1056
Ala Glu Lys Gln Met Lys Asp Lys Gln Asp Glu Glu Gln Arg Val Asp
```

```
                 340                 345                 350
atg cat ggt gat act ccg act ctt cat gaa tat atg ctg gat ctg caa    1104
Met His Gly Asp Thr Pro Thr Leu His Glu Tyr Met Leu Asp Leu Gln
    355                 360                 365 ccg gaa act act gat ctg tac gtt tat gaa caa ctg aat gat agc tct    1152
Pro Glu Thr Thr Asp Leu Tyr Val Tyr Glu Gln Leu Asn Asp Ser Ser
370                 375                 380 gaa gag gaa gat gaa att gat ggt cca gct ggt caa gca gaa ccg gat    1200
Glu Glu Glu Asp Glu Ile Asp Gly Pro Ala Gly Gln Ala Glu Pro Asp
385                 390                 395                 400 cgt gct cat tat aat att gta act ttt tgt tct aaa tgt gat tct act    1248
Arg Ala His Tyr Asn Ile Val Thr Phe Cys Ser Lys Cys Asp Ser Thr
                405                 410                 415 ctg cgt ctg gtt gta caa agc act cat gtt gat att cgt act ctg gaa    1296
Leu Arg Leu Val Val Gln Ser Thr His Val Asp Ile Arg Thr Leu Glu
            420                 425                 430 gat ctg ctt atg ggt act ctg ggt att gtt tgt ccg att tgt tct cag    1344
Asp Leu Leu Met Gly Thr Leu Gly Ile Val Cys Pro Ile Cys Ser Gln
        435                 440                 445 aaa cca taa                                                        1353
Lys Pro
    450

<210> SEQ ID NO 8
<211> LENGTH: 450
<212> TYPE: PRT
<213> ORGANISM: Artificial sequence
<220> FEATURE:
<223> OTHER INFORMATION: Synthetic protein construct

<400> SEQUENCE: 8

Met Glu Pro Ala Val Tyr Phe Lys Glu Gln Phe Leu Asp Gly Asp Gly
1               5                   10                  15

Trp Thr Ser Arg Trp Ile Glu Ser Lys His Lys Ser Asp Phe Gly Lys
            20                  25                  30

Phe Val Leu Ser Ser Gly Lys Phe Tyr Gly Asp Glu Glu Lys Asp Lys
        35                  40                  45

Gly Leu Gln Thr Ser Gln Asp Ala Arg Phe Tyr Ala Leu Ser Ala Ser
    50                  55                  60

Phe Glu Pro Phe Ser Asn Lys Gly Gln Thr Leu Val Val Gln Phe Thr
65                  70                  75                  80

Val Lys His Glu Gln Asn Ile Asp Cys Gly Gly Gly Tyr Val Lys Leu
                85                  90                  95

Phe Pro Asn Ser Leu Asp Gln Thr Asp Met His Gly Asp Ser Glu Tyr
            100                 105                 110

Asn Ile Met Phe Gly Pro Asp Ile Cys Gly Pro Gly Thr Lys Lys Val
        115                 120                 125

His Val Ile Phe Asn Tyr Lys Gly Lys Asn Val Leu Ile Asn Lys Asp
    130                 135                 140

Ile Arg Cys Lys Asp Asp Glu Phe Thr His Leu Tyr Thr Leu Ile Val
145                 150                 155                 160

Arg Pro Asp Asn Thr Tyr Glu Val Lys Ile Asp Asn Ser Gln Val Glu
                165                 170                 175

Ser Gly Ser Leu Glu Asp Asp Trp Asp Phe Leu Pro Pro Lys Lys Ile
            180                 185                 190

Lys Asp Pro Asp Ala Ser Lys Pro Glu Asp Trp Asp Glu Arg Ala Lys
        195                 200                 205

Ile Asp Asp Pro Thr Asp Ser Lys Pro Glu Asp Trp Asp Lys Pro Glu
```

```
                   210                 215                 220
His Ile Pro Asp Pro Asp Ala Lys Lys Pro Glu Asp Trp Asp Glu Glu
225                 230                 235                 240

Met Asp Gly Glu Trp Glu Pro Pro Val Ile Gln Asn Pro Glu Tyr Lys
                245                 250                 255

Gly Glu Trp Lys Pro Arg Gln Ile Asp Asn Pro Asp Tyr Lys Gly Thr
            260                 265                 270

Trp Ile His Pro Glu Ile Asp Asn Pro Glu Tyr Ser Pro Asp Pro Ser
        275                 280                 285

Ile Tyr Ala Tyr Asp Asn Phe Gly Val Leu Gly Leu Asp Leu Trp Gln
    290                 295                 300

Val Lys Ser Gly Thr Ile Phe Asp Asn Phe Leu Ile Thr Asn Asp Glu
305                 310                 315                 320

Ala Tyr Ala Glu Glu Phe Gly Asn Glu Thr Trp Gly Val Thr Lys Ala
                325                 330                 335

Ala Glu Lys Gln Met Lys Asp Lys Gln Asp Glu Glu Arg Val Asp
            340                 345                 350

Met His Gly Asp Thr Pro Thr Leu His Glu Tyr Met Leu Asp Leu Gln
        355                 360                 365

Pro Glu Thr Thr Asp Leu Tyr Val Tyr Glu Gln Leu Asn Asp Ser Ser
    370                 375                 380

Glu Glu Asp Glu Ile Asp Gly Pro Ala Gly Gln Ala Glu Pro Asp
385                 390                 395                 400

Arg Ala His Tyr Asn Ile Val Thr Phe Cys Ser Lys Cys Asp Ser Thr
                405                 410                 415

Leu Arg Leu Val Val Gln Ser Thr His Val Asp Ile Arg Thr Leu Glu
            420                 425                 430

Asp Leu Leu Met Gly Thr Leu Gly Ile Val Cys Pro Ile Cys Ser Gln
        435                 440                 445

Lys Pro
    450

<210> SEQ ID NO 9
<211> LENGTH: 1506
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: CDS
<222> LOCATION: (1)..(1506)

<400> SEQUENCE: 9 atg gag cct gcc gtc tac ttc aag gag cag ttt ctg gac gga gac ggg     48
Met Glu Pro Ala Val Tyr Phe Lys Glu Gln Phe Leu Asp Gly Asp Gly
1               5                   10                  15 tgg act tcc cgc tgg atc gaa tcc aaa cac aag tca gat ttt ggc aaa     96
Trp Thr Ser Arg Trp Ile Glu Ser Lys His Lys Ser Asp Phe Gly Lys
            20                  25                  30 ttc gtt ctc agt tcc ggc aag ttc tac ggt gac gag gag aaa gat aaa    144
Phe Val Leu Ser Ser Gly Lys Phe Tyr Gly Asp Glu Glu Lys Asp Lys
        35                  40                  45 ggt ttg cag aca agc cag gat gca cgc ttt tat gct ctg tcg gcc agt    192
Gly Leu Gln Thr Ser Gln Asp Ala Arg Phe Tyr Ala Leu Ser Ala Ser
    50                  55                  60 ttc gag cct ttc agc aac aaa ggc cag acg ctg gtg gtg cag ttc acg    240
Phe Glu Pro Phe Ser Asn Lys Gly Gln Thr Leu Val Val Gln Phe Thr
65                  70                  75                  80
```

```
                                                                    -continued
gtg aaa cat gag cag aac atc gac tgt ggg ggc ggc tat gtg aag ctg        288
Val Lys His Glu Gln Asn Ile Asp Cys Gly Gly Gly Tyr Val Lys Leu
             85                  90                  95 ttt cct aat agt ttg gac cag aca gac atg cac gga gac tca gaa tac        336
Phe Pro Asn Ser Leu Asp Gln Thr Asp Met His Gly Asp Ser Glu Tyr
        100                 105                 110 aac atc atg ttt ggt ccc gac atc tgt ggc cct ggc acc aag aag gtt        384
Asn Ile Met Phe Gly Pro Asp Ile Cys Gly Pro Gly Thr Lys Lys Val
        115                 120                 125 cat gtc atc ttc aac tac aag ggc aag aac gtg ctg atc aac aag gac        432
His Val Ile Phe Asn Tyr Lys Gly Lys Asn Val Leu Ile Asn Lys Asp
130                 135                 140 atc cgt tgc aag gat gat gag ttt aca cac ctg tac aca ctg att gtg        480
Ile Arg Cys Lys Asp Asp Glu Phe Thr His Leu Tyr Thr Leu Ile Val
145                 150                 155                 160 cgg cca gac aac acc tat gag gtg aag att gac aac agc cag gtg gag        528
Arg Pro Asp Asn Thr Tyr Glu Val Lys Ile Asp Asn Ser Gln Val Glu
                165                 170                 175 tcc ggc tcc ttg gaa gac gat tgg gac ttc ctg cca ccc aag aag ata        576
Ser Gly Ser Leu Glu Asp Asp Trp Asp Phe Leu Pro Pro Lys Lys Ile
            180                 185                 190 aag gat cct gat gct tca aaa ccg gaa gac tgg gat gag cgg gcc aag        624
Lys Asp Pro Asp Ala Ser Lys Pro Glu Asp Trp Asp Glu Arg Ala Lys
        195                 200                 205 atc gat gat ccc aca gac tcc aag cct gag gac tgg gac aag ccc gag        672
Ile Asp Asp Pro Thr Asp Ser Lys Pro Glu Asp Trp Asp Lys Pro Glu
210                 215                 220 cat atc cct gac cct gat gct aag aag ccc gag gac tgg gat gaa gag        720
His Ile Pro Asp Pro Asp Ala Lys Lys Pro Glu Asp Trp Asp Glu Glu
225                 230                 235                 240 atg gac gga gag tgg gaa ccc cca gtg att cag aac cct gag tac aag        768
Met Asp Gly Glu Trp Glu Pro Pro Val Ile Gln Asn Pro Glu Tyr Lys
                245                 250                 255 ggt gag tgg aag ccc cgg cag atc gac aac cca gat tac aag ggc act        816
Gly Glu Trp Lys Pro Arg Gln Ile Asp Asn Pro Asp Tyr Lys Gly Thr
            260                 265                 270 tgg atc cac cca gaa att gac aac ccc gag tat tct ccc gat ccc agt        864
Trp Ile His Pro Glu Ile Asp Asn Pro Glu Tyr Ser Pro Asp Pro Ser
        275                 280                 285 atc tat gcc tat gat aac ttt ggc gtg ctg ggc ctg gac ctc tgg cag        912
Ile Tyr Ala Tyr Asp Asn Phe Gly Val Leu Gly Leu Asp Leu Trp Gln
290                 295                 300 gtc aag tct ggc acc atc ttt gac aac ttc ctc atc acc aac gat gag        960
Val Lys Ser Gly Thr Ile Phe Asp Asn Phe Leu Ile Thr Asn Asp Glu
305                 310                 315                 320 gca tac gct gag gag ttt ggc aac gag acg tgg ggc gta aca aag gca       1008
Ala Tyr Ala Glu Glu Phe Gly Asn Glu Thr Trp Gly Val Thr Lys Ala
                325                 330                 335 gca gag aaa caa atg aag gac aaa cag gac gag gag cag agg ctt aag       1056
Ala Glu Lys Gln Met Lys Asp Lys Gln Asp Glu Glu Gln Arg Leu Lys
            340                 345                 350 gag gag gaa gaa gac aag aaa cgc aaa gag gag gag gca gag gac           1104
Glu Glu Glu Glu Asp Lys Lys Arg Lys Glu Glu Glu Ala Glu Asp
        355                 360                 365 aag gag gat gat gag gac aaa gat gag gat gag gag gat gag gag gac       1152
Lys Glu Asp Asp Glu Asp Lys Asp Glu Asp Glu Glu Asp Glu Glu Asp
370                 375                 380 aag gag gaa gat gag gag gaa gat gtc ccc ggc cag gcc aag gac gag       1200
Lys Glu Glu Asp Glu Glu Glu Asp Val Pro Gly Gln Ala Lys Asp Glu
385                 390                 395                 400
```

```
ctg gtc gac atg cat ggt gat act ccg act ctt cat gaa tat atg ctg      1248
Leu Val Asp Met His Gly Asp Thr Pro Thr Leu His Glu Tyr Met Leu
            405                 410                 415 gat ctg caa ccg gaa act act gat ctg tac tgt tat gaa caa ctg aat      1296
Asp Leu Gln Pro Glu Thr Thr Asp Leu Tyr Cys Tyr Glu Gln Leu Asn
        420                 425                 430 gat agc tct gaa gag gaa gat gaa att gat ggt cca gct ggt caa gca      1344
Asp Ser Ser Glu Glu Glu Asp Glu Ile Asp Gly Pro Ala Gly Gln Ala
    435                 440                 445 gaa ccg gat cgt gct cat tat aat att gta act ttt tgt tgt aaa tgt      1392
Glu Pro Asp Arg Ala His Tyr Asn Ile Val Thr Phe Cys Cys Lys Cys
450                 455                 460 gat tct act ctg cgt ctg tgt gta caa agc act cat gtt gat att cgt      1440
Asp Ser Thr Leu Arg Leu Cys Val Gln Ser Thr His Val Asp Ile Arg
465                 470                 475                 480 act ctg gaa gat ctg ctt atg ggt act ctg ggt att gtt tgt ccg att      1488
Thr Leu Glu Asp Leu Leu Met Gly Thr Leu Gly Ile Val Cys Pro Ile
                485                 490                 495 tgt tct cag aaa cca taa                                              1506
Cys Ser Gln Lys Pro
            500

<210> SEQ ID NO 10
<211> LENGTH: 501
<212> TYPE: PRT
<213> ORGANISM: Artificial sequence
<220> FEATURE:
<223> OTHER INFORMATION: Synthetic protein construct

<400> SEQUENCE: 10

Met Glu Pro Ala Val Tyr Phe Lys Glu Gln Phe Leu Asp Gly Asp Gly
1               5                   10                  15

Trp Thr Ser Arg Trp Ile Glu Ser Lys His Lys Ser Asp Phe Gly Lys
            20                  25                  30

Phe Val Leu Ser Ser Gly Lys Phe Tyr Gly Asp Glu Glu Lys Asp Lys
        35                  40                  45

Gly Leu Gln Thr Ser Gln Asp Ala Arg Phe Tyr Ala Leu Ser Ala Ser
    50                  55                  60

Phe Glu Pro Phe Ser Asn Lys Gly Gln Thr Leu Val Val Gln Phe Thr
65                  70                  75                  80

Val Lys His Glu Gln Asn Ile Asp Cys Gly Gly Gly Tyr Val Lys Leu
                85                  90                  95

Phe Pro Asn Ser Leu Asp Gln Thr Asp Met His Gly Asp Ser Glu Tyr
            100                 105                 110

Asn Ile Met Phe Gly Pro Asp Ile Cys Gly Pro Gly Thr Lys Lys Val
        115                 120                 125

His Val Ile Phe Asn Tyr Lys Gly Lys Asn Val Leu Ile Asn Lys Asp
    130                 135                 140

Ile Arg Cys Lys Asp Asp Glu Phe Thr His Leu Tyr Thr Leu Ile Val
145                 150                 155                 160

Arg Pro Asp Asn Thr Tyr Glu Val Lys Ile Asp Asn Ser Gln Val Glu
                165                 170                 175

Ser Gly Ser Leu Glu Asp Asp Trp Asp Phe Leu Pro Pro Lys Lys Ile
            180                 185                 190

Lys Asp Pro Asp Ala Ser Lys Pro Glu Asp Trp Asp Glu Arg Ala Lys
        195                 200                 205

Ile Asp Asp Pro Thr Asp Ser Lys Pro Glu Asp Trp Asp Lys Pro Glu
    210                 215                 220
```

```
His Ile Pro Asp Pro Asp Ala Lys Lys Pro Glu Asp Trp Asp Glu Glu
225                 230                 235                 240

Met Asp Gly Glu Trp Glu Pro Pro Val Ile Gln Asn Pro Glu Tyr Lys
            245                 250                 255

Gly Glu Trp Lys Pro Arg Gln Ile Asp Asn Pro Asp Tyr Lys Gly Thr
        260                 265                 270

Trp Ile His Pro Glu Ile Asp Asn Pro Glu Tyr Ser Pro Asp Pro Ser
    275                 280                 285

Ile Tyr Ala Tyr Asp Asn Phe Gly Val Leu Gly Leu Asp Leu Trp Gln
290                 295                 300

Val Lys Ser Gly Thr Ile Phe Asp Asn Phe Leu Ile Thr Asn Asp Glu
305                 310                 315                 320

Ala Tyr Ala Glu Glu Phe Gly Asn Glu Thr Trp Gly Val Thr Lys Ala
                325                 330                 335

Ala Glu Lys Gln Met Lys Asp Lys Gln Asp Glu Glu Gln Arg Leu Lys
            340                 345                 350

Glu Glu Glu Glu Asp Lys Lys Arg Lys Glu Glu Glu Ala Glu Asp
        355                 360                 365

Lys Glu Asp Asp Glu Asp Lys Asp Glu Asp Glu Glu Asp Glu Glu Asp
    370                 375                 380

Lys Glu Glu Asp Glu Glu Asp Val Pro Gly Gln Ala Lys Asp Glu
385                 390                 395                 400

Leu Val Asp Met His Gly Asp Thr Pro Thr Leu His Glu Tyr Met Leu
                405                 410                 415

Asp Leu Gln Pro Glu Thr Thr Asp Leu Tyr Cys Tyr Glu Gln Leu Asn
            420                 425                 430

Asp Ser Ser Glu Glu Glu Asp Glu Ile Asp Gly Pro Ala Gly Gln Ala
        435                 440                 445

Glu Pro Asp Arg Ala His Tyr Asn Ile Val Thr Phe Cys Cys Lys Cys
    450                 455                 460

Asp Ser Thr Leu Arg Leu Cys Val Gln Ser Thr His Val Asp Ile Arg
465                 470                 475                 480

Thr Leu Glu Asp Leu Leu Met Gly Thr Leu Gly Ile Val Cys Pro Ile
                485                 490                 495

Cys Ser Gln Lys Pro
            500

<210> SEQ ID NO 11
<211> LENGTH: 1506
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: CDS
<222> LOCATION: (1)..(1506)

<400> SEQUENCE: 11 atg gag cct gcc gtc tac ttc aag gag cag ttt ctg gac gga gac ggg    48
Met Glu Pro Ala Val Tyr Phe Lys Glu Gln Phe Leu Asp Gly Asp Gly
1               5                   10                  15 tgg act tcc cgc tgg atc gaa tcc aaa cac aag tca gat ttt ggc aaa    96
Trp Thr Ser Arg Trp Ile Glu Ser Lys His Lys Ser Asp Phe Gly Lys
            20                  25                  30 ttc gtt ctc agt tcc ggc aag ttc tac ggt gac gag gag aaa gat aaa   144
Phe Val Leu Ser Ser Gly Lys Phe Tyr Gly Asp Glu Glu Lys Asp Lys
        35                  40                  45 ggt ttg cag aca agc cag gat gca cgc ttt tat gct ctg tcg gcc agt   192
```

```
Gly Leu Gln Thr Ser Gln Asp Ala Arg Phe Tyr Ala Leu Ser Ala Ser
    50              55                  60 ttc gag cct ttc agc aac aaa ggc cag acg ctg gtg gtg cag ttc acg      240
Phe Glu Pro Phe Ser Asn Lys Gly Gln Thr Leu Val Val Gln Phe Thr
 65              70                  75                  80 gtg aaa cat gag cag aac atc gac tgt ggg ggc ggc tat gtg aag ctg      288
Val Lys His Glu Gln Asn Ile Asp Cys Gly Gly Gly Tyr Val Lys Leu
                 85                  90                  95 ttt cct aat agt ttg gac cag aca gac atg cac gga gac tca gaa tac      336
Phe Pro Asn Ser Leu Asp Gln Thr Asp Met His Gly Asp Ser Glu Tyr
            100                 105                 110 aac atc atg ttt ggt ccc gac atc tgt ggc cct ggc acc aag aag gtt      384
Asn Ile Met Phe Gly Pro Asp Ile Cys Gly Pro Gly Thr Lys Lys Val
        115                 120                 125 cat gtc atc ttc aac tac aag ggc aag aac gtg ctg atc aac aag gac      432
His Val Ile Phe Asn Tyr Lys Gly Lys Asn Val Leu Ile Asn Lys Asp
    130                 135                 140 atc cgt tgc aag gat gat gag ttt aca cac ctg tac aca ctg att gtg      480
Ile Arg Cys Lys Asp Asp Glu Phe Thr His Leu Tyr Thr Leu Ile Val
145                 150                 155                 160 cgg cca gac aac acc tat gag gtg aag att gac aac agc cag gtg gag      528
Arg Pro Asp Asn Thr Tyr Glu Val Lys Ile Asp Asn Ser Gln Val Glu
                165                 170                 175 tcc ggc tcc ttg gaa gac gat tgg gac ttc ctg cca ccc aag aag ata      576
Ser Gly Ser Leu Glu Asp Asp Trp Asp Phe Leu Pro Pro Lys Lys Ile
            180                 185                 190 aag gat cct gat gct tca aaa ccg gaa gac tgg gat gag cgg gcc aag      624
Lys Asp Pro Asp Ala Ser Lys Pro Glu Asp Trp Asp Glu Arg Ala Lys
        195                 200                 205 atc gat gat ccc aca gac tcc aag cct gag gac tgg gac aag ccc gag      672
Ile Asp Asp Pro Thr Asp Ser Lys Pro Glu Asp Trp Asp Lys Pro Glu
    210                 215                 220 cat atc cct gac cct gat gct aag aag ccc gag gac tgg gat gaa gag      720
His Ile Pro Asp Pro Asp Ala Lys Lys Pro Glu Asp Trp Asp Glu Glu
225                 230                 235                 240 atg gac gga gag tgg gaa ccc cca gtg att cag aac cct gag tac aag      768
Met Asp Gly Glu Trp Glu Pro Pro Val Ile Gln Asn Pro Glu Tyr Lys
                245                 250                 255 ggt gag tgg aag ccc cgg cag atc gac aac cca gat tac aag ggc act      816
Gly Glu Trp Lys Pro Arg Gln Ile Asp Asn Pro Asp Tyr Lys Gly Thr
            260                 265                 270 tgg atc cac cca gaa att gac aac ccc gag tat tct ccc gat ccc agt      864
Trp Ile His Pro Glu Ile Asp Asn Pro Glu Tyr Ser Pro Asp Pro Ser
        275                 280                 285 atc tat gcc tat gat aac ttt ggc gtg ctg ggc ctg gac ctc tgg cag      912
Ile Tyr Ala Tyr Asp Asn Phe Gly Val Leu Gly Leu Asp Leu Trp Gln
    290                 295                 300 gtc aag tct ggc acc atc ttt gac aac ttc ctc atc acc aac gat gag      960
Val Lys Ser Gly Thr Ile Phe Asp Asn Phe Leu Ile Thr Asn Asp Glu
305                 310                 315                 320 gca tac gct gag gag ttt ggc aac gag acg tgg ggc gta aca aag gca     1008
Ala Tyr Ala Glu Glu Phe Gly Asn Glu Thr Trp Gly Val Thr Lys Ala
                325                 330                 335 gca gag aaa caa atg aag gac aaa cag gac gag gag cag agg ctt aag     1056
Ala Glu Lys Gln Met Lys Asp Lys Gln Asp Glu Glu Gln Arg Leu Lys
            340                 345                 350 gag gag gaa gaa gac aag aaa cgc aaa gag gag gag gca gag gac         1104
Glu Glu Glu Glu Asp Lys Lys Arg Lys Glu Glu Glu Ala Glu Asp
        355                 360                 365 aag gag gat gat gag gac aaa gat gag gat gag gag gat gag gag gac     1152
```

```
                                      -continued

Lys Glu Asp Asp Glu Asp Lys Asp Glu Asp Glu Glu Asp
                      370                 375                 380 aag gag gaa gat gag gag gaa gat gtc ccc ggc cag gcc aag gac gag           1200
Lys Glu Glu Asp Glu Glu Glu Asp Val Pro Gly Gln Ala Lys Asp Glu
385                 390                 395                 400 ctg gtc gac atg cat ggt gat act ccg act ctt cat gaa tat atg ctg           1248
Leu Val Asp Met His Gly Asp Thr Pro Thr Leu His Glu Tyr Met Leu
                405                 410                 415 gat ctg caa ccg gaa act act gat ctg tac tgt tat gaa caa ctg aat           1296
Asp Leu Gln Pro Glu Thr Thr Asp Leu Tyr Cys Tyr Glu Gln Leu Asn
            420                 425                 430 gat agc tct gaa gag gaa gat gaa att gat ggt cca gct ggt caa gca           1344
Asp Ser Ser Glu Glu Glu Asp Glu Ile Asp Gly Pro Ala Gly Gln Ala
        435                 440                 445 gaa ccg gat cgt gct cat tat aat att gta act ttt tgt tct aaa tgt           1392
Glu Pro Asp Arg Ala His Tyr Asn Ile Val Thr Phe Cys Ser Lys Cys
    450                 455                 460 gat tct act ctg cgt ctg gtt gta caa agc act cat gtt gat att cgt           1440
Asp Ser Thr Leu Arg Leu Val Val Gln Ser Thr His Val Asp Ile Arg
465                 470                 475                 480 act ctg gaa gat ctg ctt atg ggt act ctg ggt att gtt tgt ccg att           1488
Thr Leu Glu Asp Leu Leu Met Gly Thr Leu Gly Ile Val Cys Pro Ile
                485                 490                 495 tgt tct cag aaa cca taa                                                   1506
Cys Ser Gln Lys Pro
                500

<210> SEQ ID NO 12
<211> LENGTH: 501
<212> TYPE: PRT
<213> ORGANISM: Artificial sequence
<220> FEATURE:
<223> OTHER INFORMATION: Synthetic protein construct

<400> SEQUENCE: 12

Met Glu Pro Ala Val Tyr Phe Lys Glu Gln Phe Leu Asp Gly Asp Gly
1               5                   10                  15

Trp Thr Ser Arg Trp Ile Glu Ser Lys His Lys Ser Asp Phe Gly Lys
            20                  25                  30

Phe Val Leu Ser Ser Gly Lys Phe Tyr Gly Asp Glu Glu Lys Asp Lys
        35                  40                  45

Gly Leu Gln Thr Ser Gln Asp Ala Arg Phe Tyr Ala Leu Ser Ala Ser
    50                  55                  60

Phe Glu Pro Phe Ser Asn Lys Gly Gln Thr Leu Val Val Gln Phe Thr
65                  70                  75                  80

Val Lys His Glu Gln Asn Ile Asp Cys Gly Gly Gly Tyr Val Lys Leu
                85                  90                  95

Phe Pro Asn Ser Leu Asp Gln Thr Asp Met His Gly Asp Ser Glu Tyr
            100                 105                 110

Asn Ile Met Phe Gly Pro Asp Ile Cys Gly Pro Gly Thr Lys Lys Val
        115                 120                 125

His Val Ile Phe Asn Tyr Lys Gly Lys Asn Val Leu Ile Asn Lys Asp
    130                 135                 140

Ile Arg Cys Lys Asp Asp Glu Phe Thr His Leu Tyr Thr Leu Ile Val
145                 150                 155                 160

Arg Pro Asp Asn Thr Tyr Glu Val Lys Ile Asp Asn Ser Gln Val Glu
                165                 170                 175

Ser Gly Ser Leu Glu Asp Asp Trp Asp Phe Leu Pro Pro Lys Lys Ile
            180                 185                 190
```

Lys Asp Pro Asp Ala Ser Lys Pro Glu Asp Trp Asp Glu Arg Ala Lys
            195                 200                 205

Ile Asp Asp Pro Thr Asp Ser Lys Pro Glu Asp Trp Asp Lys Pro Glu
        210                 215                 220

His Ile Pro Asp Pro Asp Ala Lys Lys Pro Glu Asp Trp Asp Glu Glu
225                 230                 235                 240

Met Asp Gly Glu Trp Glu Pro Pro Val Ile Gln Asn Pro Glu Tyr Lys
                245                 250                 255

Gly Glu Trp Lys Pro Arg Gln Ile Asp Asn Pro Asp Tyr Lys Gly Thr
            260                 265                 270

Trp Ile His Pro Glu Ile Asp Asn Pro Glu Tyr Ser Pro Asp Pro Ser
        275                 280                 285

Ile Tyr Ala Tyr Asp Asn Phe Gly Val Leu Gly Leu Asp Leu Trp Gln
    290                 295                 300

Val Lys Ser Gly Thr Ile Phe Asp Asn Phe Leu Ile Thr Asn Asp Glu
305                 310                 315                 320

Ala Tyr Ala Glu Glu Phe Gly Asn Glu Thr Trp Gly Val Thr Lys Ala
                325                 330                 335

Ala Glu Lys Gln Met Lys Asp Lys Gln Asp Glu Glu Gln Arg Leu Lys
            340                 345                 350

Glu Glu Glu Glu Asp Lys Lys Arg Lys Glu Glu Glu Ala Glu Asp
        355                 360                 365

Lys Glu Asp Asp Glu Asp Lys Asp Glu Asp Glu Glu Asp
    370                 375                 380

Lys Glu Glu Asp Glu Glu Asp Val Pro Gly Gln Ala Lys Asp Glu
385                 390                 395                 400

Leu Val Asp Met His Gly Asp Thr Pro Thr Leu His Glu Tyr Met Leu
                405                 410                 415

Asp Leu Gln Pro Glu Thr Thr Asp Leu Tyr Cys Tyr Glu Gln Leu Asn
            420                 425                 430

Asp Ser Ser Glu Glu Glu Asp Glu Ile Asp Gly Pro Ala Gly Gln Ala
        435                 440                 445

Glu Pro Asp Arg Ala His Tyr Asn Ile Val Thr Phe Cys Ser Lys Cys
    450                 455                 460

Asp Ser Thr Leu Arg Leu Val Val Gln Ser Thr His Val Asp Ile Arg
465                 470                 475                 480

Thr Leu Glu Asp Leu Leu Met Gly Thr Leu Gly Ile Val Cys Pro Ile
                485                 490                 495

Cys Ser Gln Lys Pro
            500

<210> SEQ ID NO 13
<211> LENGTH: 1506
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: CDS
<222> LOCATION: (1)..(1506)

<400> SEQUENCE: 13 atg gag cct gcc gtc tac ttc aag gag cag ttt ctg gac gga gac ggg    48
Met Glu Pro Ala Val Tyr Phe Lys Glu Gln Phe Leu Asp Gly Asp Gly
1               5                   10                  15 tgg act tcc cgc tgg atc gaa tcc aaa cac aag tca gat ttt ggc aaa    96
Trp Thr Ser Arg Trp Ile Glu Ser Lys His Lys Ser Asp Phe Gly Lys

```
                    20                  25                  30
ttc gtt ctc agt tcc ggc aag ttc tac ggt gac gag gag aaa gat aaa         144
Phe Val Leu Ser Ser Gly Lys Phe Tyr Gly Asp Glu Glu Lys Asp Lys
             35                  40                  45 ggt ttg cag aca agc cag gat gca cgc ttt tat gct ctg tcg gcc agt         192
Gly Leu Gln Thr Ser Gln Asp Ala Arg Phe Tyr Ala Leu Ser Ala Ser
 50                  55                  60 ttc gag cct ttc agc aac aaa ggc cag acg ctg gtg gtg cag ttc acg         240
Phe Glu Pro Phe Ser Asn Lys Gly Gln Thr Leu Val Val Gln Phe Thr
 65                  70                  75                  80 gtg aaa cat gag cag aac atc gac tgt ggg ggc ggc tat gtg aag ctg         288
Val Lys His Glu Gln Asn Ile Asp Cys Gly Gly Gly Tyr Val Lys Leu
                     85                  90                  95 ttt cct aat agt ttg gac cag aca gac atg cac gga gac tca gaa tac         336
Phe Pro Asn Ser Leu Asp Gln Thr Asp Met His Gly Asp Ser Glu Tyr
            100                 105                 110 aac atc atg ttt ggt ccc gac atc tgt ggc cct ggc acc aag aag gtt         384
Asn Ile Met Phe Gly Pro Asp Ile Cys Gly Pro Gly Thr Lys Lys Val
            115                 120                 125 cat gtc atc ttc aac tac aag ggc aag aac gtg ctg atc aac aag gac         432
His Val Ile Phe Asn Tyr Lys Gly Lys Asn Val Leu Ile Asn Lys Asp
130                 135                 140 atc cgt tgc aag gat gat gag ttt aca cac ctg tac aca ctg att gtg         480
Ile Arg Cys Lys Asp Asp Glu Phe Thr His Leu Tyr Thr Leu Ile Val
145                 150                 155                 160 cgg cca gac aac acc tat gag gtg aag att gac aac agc cag gtg gag         528
Arg Pro Asp Asn Thr Tyr Glu Val Lys Ile Asp Asn Ser Gln Val Glu
                165                 170                 175 tcc ggc tcc ttg gaa gac gat tgg gac ttc ctg cca ccc aag aag ata         576
Ser Gly Ser Leu Glu Asp Asp Trp Asp Phe Leu Pro Pro Lys Lys Ile
            180                 185                 190 aag gat cct gat gct tca aaa ccg gaa gac tgg gat gag cgg gcc aag         624
Lys Asp Pro Asp Ala Ser Lys Pro Glu Asp Trp Asp Glu Arg Ala Lys
            195                 200                 205 atc gat gat ccc aca gac tcc aag cct gag gac tgg gac aag ccc gag         672
Ile Asp Asp Pro Thr Asp Ser Lys Pro Glu Asp Trp Asp Lys Pro Glu
210                 215                 220 cat atc cct gac cct gat gct aag aag ccc gag gac tgg gat gaa gag         720
His Ile Pro Asp Pro Asp Ala Lys Lys Pro Glu Asp Trp Asp Glu Glu
225                 230                 235                 240 atg gac gga gag tgg gaa ccc cca gtg att cag aac cct gag tac aag         768
Met Asp Gly Glu Trp Glu Pro Pro Val Ile Gln Asn Pro Glu Tyr Lys
                245                 250                 255 ggt gag tgg aag ccc cgg cag atc gac aac cca gat tac aag ggc act         816
Gly Glu Trp Lys Pro Arg Gln Ile Asp Asn Pro Asp Tyr Lys Gly Thr
            260                 265                 270 tgg atc cac cca gaa att gac aac ccc gag tat tct ccc gat ccc agt         864
Trp Ile His Pro Glu Ile Asp Asn Pro Glu Tyr Ser Pro Asp Pro Ser
            275                 280                 285 atc tat gcc tat gat aac ttt ggc gtg ctg ggc ctg gac ctc tgg cag         912
Ile Tyr Ala Tyr Asp Asn Phe Gly Val Leu Gly Leu Asp Leu Trp Gln
            290                 295                 300 gtc aag tct ggc acc atc ttt gac aac ttc ctc atc acc aac gat gag         960
Val Lys Ser Gly Thr Ile Phe Asp Asn Phe Leu Ile Thr Asn Asp Glu
305                 310                 315                 320 gca tac gct gag gag ttt ggc aac gag acg tgg ggc gta aca aag gca        1008
Ala Tyr Ala Glu Glu Phe Gly Asn Glu Thr Trp Gly Val Thr Lys Ala
                325                 330                 335 gca gag aaa caa atg aag gac aaa cag gac gag gag cag agg ctt aag        1056
Ala Glu Lys Gln Met Lys Asp Lys Gln Asp Glu Glu Gln Arg Leu Lys
```

```
                          340                 345                 350
gag gag gaa gaa gac aag aaa cgc aaa gag gag gag gag gca gag gac              1104
Glu Glu Glu Glu Asp Lys Lys Arg Lys Glu Glu Glu Glu Ala Glu Asp
            355                 360                 365 aag gag gat gat gag gac aaa gat gag gat gag gag gat gag gag gac              1152
Lys Glu Asp Asp Glu Asp Lys Asp Glu Asp Glu Glu Asp Glu Glu Asp
370                 375                 380 aag gag gaa gat gag gag gaa gat gtc ccc ggc cag gcc aag gac gag              1200
Lys Glu Glu Asp Glu Glu Glu Asp Val Pro Gly Gln Ala Lys Asp Glu
385                 390                 395                 400 ctg gtc gac atg cat ggt gat act ccg act ctt cat gaa tat atg ctg              1248
Leu Val Asp Met His Gly Asp Thr Pro Thr Leu His Glu Tyr Met Leu
                405                 410                 415 gat ctg caa ccg gaa act act gat ctg tac gtt tat gaa caa ctg aat              1296
Asp Leu Gln Pro Glu Thr Thr Asp Leu Tyr Val Tyr Glu Gln Leu Asn
            420                 425                 430 gat agc tct gaa gag gaa gat gaa att gat ggt cca gct ggt caa gca              1344
Asp Ser Ser Glu Glu Glu Asp Glu Ile Asp Gly Pro Ala Gly Gln Ala
        435                 440                 445 gaa ccg gat cgt gct cat tat aat att gta act ttt tgt tct aaa tgt              1392
Glu Pro Asp Arg Ala His Tyr Asn Ile Val Thr Phe Cys Ser Lys Cys
450                 455                 460 gat tct act ctg cgt ctg gtt gta caa agc act cat gtt gat att cgt              1440
Asp Ser Thr Leu Arg Leu Val Val Gln Ser Thr His Val Asp Ile Arg
465                 470                 475                 480 act ctg gaa gat ctg ctt atg ggt act ctg ggt att gtt tgt ccg att              1488
Thr Leu Glu Asp Leu Leu Met Gly Thr Leu Gly Ile Val Cys Pro Ile
                485                 490                 495 tgt tct cag aaa cca taa                                                      1506
Cys Ser Gln Lys Pro
            500
```

<210> SEQ ID NO 14
<211> LENGTH: 501
<212> TYPE: PRT
<213> ORGANISM: Artificial sequence
<220> FEATURE:
<223> OTHER INFORMATION: Synthetic protein construct

<400> SEQUENCE: 14

```
Met Glu Pro Ala Val Tyr Phe Lys Glu Gln Phe Leu Asp Gly Asp Gly
1               5                   10                  15

Trp Thr Ser Arg Trp Ile Glu Ser Lys His Lys Ser Asp Phe Gly Lys
            20                  25                  30

Phe Val Leu Ser Ser Gly Lys Phe Tyr Gly Asp Glu Lys Asp Lys
        35                  40                  45

Gly Leu Gln Thr Ser Gln Asp Ala Arg Phe Tyr Ala Leu Ser Ala Ser
    50                  55                  60

Phe Glu Pro Phe Ser Asn Lys Gly Gln Thr Leu Val Val Gln Phe Thr
65                  70                  75                  80

Val Lys His Glu Gln Asn Ile Asp Cys Gly Gly Gly Tyr Val Lys Leu
                85                  90                  95

Phe Pro Asn Ser Leu Asp Gln Thr Asp Met His Gly Asp Ser Glu Tyr
            100                 105                 110

Asn Ile Met Phe Gly Pro Asp Ile Cys Gly Pro Gly Thr Lys Lys Val
        115                 120                 125

His Val Ile Phe Asn Tyr Lys Gly Lys Asn Val Leu Ile Asn Lys Asp
    130                 135                 140

Ile Arg Cys Lys Asp Asp Glu Phe Thr His Leu Tyr Thr Leu Ile Val
```

```
                145                 150                 155                 160
Arg Pro Asp Asn Thr Tyr Glu Val Lys Ile Asp Asn Ser Gln Val Glu
                165                 170                 175

Ser Gly Ser Leu Glu Asp Asp Trp Asp Phe Leu Pro Pro Lys Lys Ile
            180                 185                 190

Lys Asp Pro Asp Ala Ser Lys Pro Glu Asp Trp Asp Glu Arg Ala Lys
        195                 200                 205

Ile Asp Asp Pro Thr Asp Ser Lys Pro Glu Asp Trp Asp Lys Pro Glu
    210                 215                 220

His Ile Pro Asp Pro Asp Ala Lys Lys Pro Glu Asp Trp Asp Glu Glu
225                 230                 235                 240

Met Asp Gly Glu Trp Glu Pro Pro Val Ile Gln Asn Pro Glu Tyr Lys
                245                 250                 255

Gly Glu Trp Lys Pro Arg Gln Ile Asp Asn Pro Asp Tyr Lys Gly Thr
            260                 265                 270

Trp Ile His Pro Glu Ile Asp Asn Pro Glu Tyr Ser Pro Asp Pro Ser
        275                 280                 285

Ile Tyr Ala Tyr Asp Asn Phe Gly Val Leu Gly Leu Asp Leu Trp Gln
    290                 295                 300

Val Lys Ser Gly Thr Ile Phe Asp Asn Phe Leu Ile Thr Asn Asp Glu
305                 310                 315                 320

Ala Tyr Ala Glu Glu Phe Gly Asn Glu Thr Trp Gly Val Thr Lys Ala
                325                 330                 335

Ala Glu Lys Gln Met Lys Asp Lys Gln Asp Glu Glu Gln Arg Leu Lys
            340                 345                 350

Glu Glu Glu Glu Asp Lys Lys Arg Lys Glu Glu Glu Glu Ala Glu Asp
        355                 360                 365

Lys Glu Asp Asp Glu Asp Lys Asp Glu Asp Glu Asp Glu Glu Asp
    370                 375                 380

Lys Glu Glu Asp Glu Glu Glu Asp Val Pro Gly Gln Ala Lys Asp Glu
385                 390                 395                 400

Leu Val Asp Met His Gly Asp Thr Pro Thr Leu His Glu Tyr Met Leu
                405                 410                 415

Asp Leu Gln Pro Glu Thr Thr Asp Leu Tyr Val Tyr Glu Gln Leu Asn
            420                 425                 430

Asp Ser Ser Glu Glu Glu Asp Glu Ile Asp Gly Pro Ala Gly Gln Ala
        435                 440                 445

Glu Pro Asp Arg Ala His Tyr Asn Ile Val Thr Phe Cys Ser Lys Cys
    450                 455                 460

Asp Ser Thr Leu Arg Leu Val Val Gln Ser Thr His Val Asp Ile Arg
465                 470                 475                 480

Thr Leu Glu Asp Leu Leu Met Gly Thr Leu Gly Ile Val Cys Pro Ile
                485                 490                 495

Cys Ser Gln Lys Pro
            500

<210> SEQ ID NO 15
<211> LENGTH: 10
<212> TYPE: PRT
<213> ORGANISM: Human papillomavirus

<400> SEQUENCE: 15

Tyr Met Leu Asp Leu Gln Pro Glu Thr Thr
1               5                   10
```

```
<210> SEQ ID NO 16
<211> LENGTH: 8
<212> TYPE: PRT
<213> ORGANISM: Human papillomavirus

<400> SEQUENCE: 16

Thr Leu Gly Ile Val Cys Pro Ile
1               5

<210> SEQ ID NO 17
<211> LENGTH: 9
<212> TYPE: PRT
<213> ORGANISM: Human papillomavirus

<400> SEQUENCE: 17

Leu Leu Met Gly Thr Leu Gly Ile Val
1               5

<210> SEQ ID NO 18
<211> LENGTH: 44
<212> TYPE: DNA
<213> ORGANISM: Artificial sequence
<220> FEATURE:
<223> OTHER INFORMATION: Synthetic oligonucleotide primer

<400> SEQUENCE: 18
ggaattccat atggagcctg ccgtctactt caaggagcag tttc              44

<210> SEQ ID NO 19
<211> LENGTH: 42
<212> TYPE: DNA
<213> ORGANISM: Artificial sequence
<220> FEATURE:
<223> OTHER INFORMATION: Synthetic oligonucleotide primer

<400> SEQUENCE: 19
cgcgtcgacc ctctgctcct cgtcctgttt gtccttcatt tg                42

<210> SEQ ID NO 20
<211> LENGTH: 44
<212> TYPE: DNA
<213> ORGANISM: Artificial sequence
<220> FEATURE:
<223> OTHER INFORMATION: Synthetic oligonucleotide primer

<400> SEQUENCE: 20
ggaattccat atggagcctg ccgtctactt caaggagcag tttc              44

<210> SEQ ID NO 21
<211> LENGTH: 42
<212> TYPE: DNA
<213> ORGANISM: Artificial sequence
<220> FEATURE:
<223> OTHER INFORMATION: Synthetic oligonucleotide primer

<400> SEQUENCE: 21
cgcgtcgacc agctcgtcct tggcctggcc ggggacatct tc                42
```

HPV ANTIGEN FUSION PROTEIN VACCINE COMPOSITIONS AND USES THEREOF

CROSS-REFERENCE TO RELATED APPLICATIONS

This application claims priority to PCT Application No. PCT/CN2006/002778, filed Oct. 19, 2006, the entire disclosure of which is incorporated herein by reference.

FIELD OF THE INVENTION

The present invention relates generally to vaccine compositions useful in the treatment and/or prevention of disease. In particular, the present invention relates to vaccine compositions comprising a fusion polypeptide of a mutated E7 antigen for human papillomavirus and an immunostimulatory polypeptide.

BACKGROUND OF THE INVENTION

The following description is provided to assist the understanding of the reader. None of the information provided or references cited is admitted to be prior art to the present invention.

Human papillomavirus (HPV) is a generic name for a group of epithelial cell specific viruses which have a diversity of DNA restriction enzyme profiles and different capsid protein antigenicity. Such viruses show similar shapes and are widespread in human and animals. They are highly specific, without cross-species transmission. Up to now, the number of defined types of HPV is more than 110. They are grouped into high-risk types and low-risk types, based on the correlation of the HPV types and oncogenic risks. Low-risk type HPVs, e.g., HPV6, 11, 42, 43, 44, often cause benign lesions, such as external genital warts. High-risk type HPVs, e.g., HPV16, 18, 31, 33, 35, 39, 45, 51, 52, 56, 58, 59, 68, are associated with the developments of cervical cancer and cervical intraepithelial neoplasm (CIN). Research on specimens from worldwide cervical cancer tissues indicated that HPV16 and 18 have the highest infection rates. Among all of the detected types, HPV16 accounts for 50%, HPV18 for 14%, HPV45 for 8%, HPV31 for 5% and HPVs of other types account for 23% of infections. The HPV viral genome consists of three gene regions: early region (E), late region (L) and non-coding upstream regulatory region (URR), in which the early region comprises six early open reading frames, respectively defined as E1, E2, E4, E5, E6 and E7. Proteins E6 and E7 are oncoproteins, and play an important role in viral replication and immortalization and transformation of cells (Park et al., *Cancer* 76:1902-1913 (1995)).

One early region gene, E7, encodes a small polypeptide with a molecular weight of about 10 KD, which can bind to a gene expression product of retinoblastoma, Rb. Rb is a tumor suppressor, which can bind to transcription factor E2F and inactivate it. E2F regulates the transcription of many growth related genes. The formation of Rb-E2F complex prevents the expression of these genes in $G_0$ and $G_1$ phases, and thus limits their expression to S phase. In S phase, Rb-E2F complex is "programmed" to be disassociated, so as to release active transcription factor E2F. The formation of Rb-E7 complex will prevent the formation of Rb-E2F complex and shorten S phase, i.e., promote the cell cycle progression. E7 protein of HPV types with high oncogenicity has a higher affinity to Rb when compared to E7 protein of non-tumorigenic HPV types.

SUMMARY OF THE INVENTION

This invention relates generally to the preparation of HPV fusion polypeptides and uses of the same. In particular, the present invention relates to the preparation of vaccines that stimulate an immune response against cells expressing an HPV antigen to provide a prophylactic and/or therapeutic benefit.

In one aspect, the present invention provides a vaccine composition comprising a fusion protein of an immunostimulatory polypeptide and a mutant HPV antigen, wherein the mutant HPV antigen is an E7 polypeptide comprising substitutions in at least two cysteine residues. In particular embodiments, the fusion protein comprises a sequence selected from the group consisting of: SEQ ID NOS: 6, 8, 12, and 14.

In certain embodiments, the present invention provides a vaccine composition comprising a fusion protein of an immunostimulatory polypeptide and a mutant HPV antigen, which is soluble when expressed in recombinant *E. coli* cells. In a particular embodiment, a HPV fusion polypeptide comprising calreticulin and an E7 polypeptide exhibits greater solubility in *E. coli* compared to the fusion proteins Hsp70 and E7 or Hsp60 and E7.

In various embodiments, the immunostimulatory polypeptide may be selected from the group consisting of: calreticulin, calnexin, tapasin, ER60, Hsp27, Hsp40, Hsp70, Hsp90, Hsp100, and Hsp110. In one embodiment, the immunostimulatory polypeptide is calreticulin or a biologically active domain, fragment, or homolog thereof. In particular embodiments, the immunostimulatory polypeptide is an N-terminal domain of human calreticulin comprising amino acids 18-366 of SEQ ID NO: 2 or amino acids 18-180 of SEQ ID NO: 2.

In one embodiment, the mutant E7 polypeptide has substitutions at one or more cysteine residues of SEQ ID NO:1 selected from the group consisting of cysteine-24, cysteine-59, and cysteine-68. In a one embodiment, the mutant E7 polypeptide has two substitutions at cysteine-59 and cysteine-68 of SEQ ID NO:1. In another embodiment, the mutant E7 polypeptide has three substitutions at cysteine-24, cysteine-59, and cysteine-68 of SEQ ID NO:1.

In one embodiment, the vaccine composition comprises a fusion protein of an immunostimulatory polypeptide and a mutant HPV antigen and an adjuvant. The adjuvant may be, for example, BCG.

In one aspect, the present invention provides a pharmaceutical composition for the treatment or prevention of a human papilloma virus-related disease, comprising an effective amount of the fusion protein of an immunostimulatory polypeptide and a mutant HPV antigen, wherein the mutant HPV antigen is an E7 polypeptide comprising substitutions in at least two cysteine residues, and a pharmaceutically acceptable carrier. In one embodiment, the pharmaceutical composition further comprises an adjuvant, for example, BCG.

In one aspect, the present invention provides nucleic acid molecules encoding a fusion protein of an immunostimulatory polypeptide and a mutant HPV antigen, wherein the mutant HPV antigen is an E7 polypeptide comprising substitutions in at least two cysteine residues. In particular embodiments, the nucleic acid encoding the fusion protein is selected from the group consisting of: SEQ ID NOS: 5, 7, 11, and 13.

In one aspect, the present invention provides expression vectors and host cells comprising nucleic acid molecules encoding a fusion protein of an immunostimulatory polypeptide and a mutant HPV antigen, wherein the mutant HPV antigen is an E7 polypeptide comprising substitutions in at least two cysteine residues.

In one aspect, the present invention provides a method for the treatment or prevention of a human papilloma virus related disease, comprising the administration of an effective amount of a fusion protein comprising an immunostimulatory polypeptide and a mutant HPV antigen, wherein the mutant HPV antigen is an E7 polypeptide comprising substitutions in at least two cysteine residues. In various embodiments, the human papilloma virus-related disease is selected from the group consisting of: cervical cancer, anal intraepithelial neoplasia, cervical intraepithelial neoplasia, anogenital warts, recurrent respiratory tract papilloma, and vaginal intraepithelial neoplasia.

In one embodiment, the fusion protein is administered prior to the occurrence of a human papilloma virus-related disease. In another embodiment, the fusion protein is administered after diagnosis of a human papilloma virus-related disease.

In one aspect, the present invention provides a method for the treatment or prevention of a human papilloma virus-related disease, comprising the administration of an effective amount of a nucleic acid encoding a fusion protein comprising an immunostimulatory polypeptide and a mutant HPV antigen, wherein the mutant HPV antigen is an E7 polypeptide comprising substitutions in at least two cysteine residues. In particular embodiments, the nucleic acid encoding the fusion protein is selected from the group consisting of: SEQ ID NOS: 5, 7, 11, and 13. In one embodiment, the nucleic acid may be provided directly to a subject. In another embodiment, the nucleic acid is contacted with immune cells ex vivo.

In one aspect, the present invention provides, a method of making a vaccine composition comprising expressing a nucleic acid encoding a recombinant fusion protein of an immunostimulatory polypeptide and a mutant HPV antigen in a host cell, wherein the mutant HPV antigen is an E7 polypeptide comprising substitutions in at least two cysteine residues. In one embodiment, the host cell is an *E. coli* cell.

BRIEF DESCRIPTION OF THE DRAWINGS

FIG. 1 shows SDS-PAGE analysis of recombinant HPV fusion polypeptides. FIG. 1A shows duplicate samples of freshly prepared C6E7 protein run under non-reducing (lanes 1-2) or reducing (lanes 3-4) conditions. FIG. 1B shows duplicate samples of freshly prepared C6E7m2 protein run under non-reducing (lanes 1-2) or reducing (lanes 3-4) conditions. FIG. 1C shows duplicate samples of freshly prepared C6E7m3 protein run under non-reducing (lanes 1-2) or reducing (lanes 3-4) conditions. FIG. 1D shows samples of C6E7, C6E7m2, and C6E7m3 protein stored at 4° C. for 2 months run under non-reducing (lanes 1-3, respectively) or reducing (lanes 4-6 respectively) conditions. FIG. 1E shows samples of C6E7, C6E7m2, and C6E7m3 protein stored at −80° C. for 1.5 months run under non-reducing (lanes 1-3, respectively) or reducing (lanes 4-6 respectively) conditions.

FIG. 3 shows graphs of tumor incidence in mice administered recombinant HPV fusion polypeptides of the present invention prior to challenge with TC-1 tumor cells.

FIG. 4 shows graphs of tumor incidence in mice administered recombinant HPV fusion polypeptides of the present invention after challenge with TC-1 tumor cells.

FIG. 6 is a graph of cytotoxic T-lymphocyte mediated lysis caused by cells isolated from mice immunized with recombinant HPV fusion polypeptides of the present invention.

FIG. 7 is a graph of IFN-γ production in isolated splenocytes from mice immunized with recombinant HPV fusion polypeptides of the present invention.

DETAILED DESCRIPTION

Figure 2A:
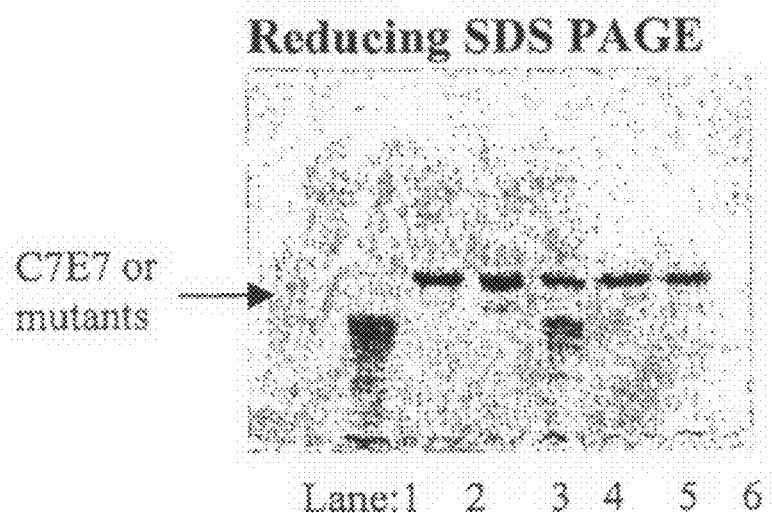
FIG. 2 shows SDS-PAGE analysis of recombinant HPV fusion polypeptides conducted under reducing (FIG. 1A) or non-reducing (FIG. 1B) conditions. In both gels, the samples were: Lane 1, C7E7 stored at 4° C. for 7 d; Lane 2, C7E7m2 stored at 4° C. for 7d; Lane 3, C7E7m3 stored at 4° C. for 7 d; Lane 4, C7E7 stored at −20° C. for 7 d; Lane 5, C7E7m2 stored at −20° C. for 7 d; Lane 6, C7E7m3 stored at −20° C. for 7 d.

It is to be appreciated that certain aspects, modes, embodiments, variations and features of the invention are described below in various levels of detail in order to provide a substantial understanding of the present invention.

The present invention generally relates to fusion proteins comprising mutant forms of the HPV E7 antigen and an immunostimulatory polypeptide, which are useful as vaccines for the prevention and/or treatment of HPV-related diseases. While not wishing to be limited by theory, a fusion of an immunostimulatory polypeptide with an HPV antigen can promote the immune response against HPV by, for example, assisting MHC class I/peptide assembly. Thus, the combination may enhance the therapeutic effect of vaccines in the treatment or prevention of an HPV-related disease.

Definitions. In the description that follows, a number of terms are utilized extensively. Definitions are herein provided to facilitate understanding of the invention. The terms defined below are more fully defined by reference to the specification as a whole.

Units, prefixes, and symbols may be denoted in their accepted SI form. Unless otherwise indicated, nucleic acids are written left to right in 5' to 3' orientation; amino acid sequences are written left to right in amino to carboxy orientation. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes.

The terms "a" and "an" as used herein mean "one or more" unless the singular is expressly specified.

As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, the term "antibody" means a polypeptide comprising a framework region from an immunoglobulin gene or fragments thereof that specifically binds and recognizes an antigen, e.g., an HPV E7 antigen. Use of the term antibody is meant to include whole antibodies, including single-chain whole antibodies, and antigen-binding fragments thereof. The term "antibody" includes bispecific antibodies and multispecific antibodies so long as they exhibit the desired biological activity or function.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the invention are any combinations of variable region(s) and hinge region, $CH_1$, $CH_2$, and $CH_3$ domains. Antibody-related molecules useful as binding agents of the invention include, e.g., but are not limited to, Fab, Fab' and $F(ab')_2$, Fd, single-chain Fvs (scFv), single-chain antibodies, disulfide-linked Fvs (sdFv) and fragments comprising either a $V_L$, or $V_H$ domain. Examples include: (i) a Fab fragment, a monovalent fragment consisting of the $V_L$, $V_H$, $C_L$, and $CH_1$ domains; (ii) a $F(ab')_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$, and $V_H$ domains of a single arm of an antibody, (v) a dAb fragment (Ward et al., Nature 341: 544-546, 1989), which consists of a $V_H$ domain; and (vi) an isolated complementarity determining region (CDR). As such "antibody fragments" can comprise a portion of a full length antibody, generally the antigen binding or variable region thereof. Examples of antibody fragments include Fab, Fab', $F(ab')_2$, and Fv fragments; diabodies; linear antibodies; single-chain antibody molecules; and multispecific antibodies formed from antibody fragments. Single-chain antibody molecules may comprise a polymer with a number of individual molecules, for example, dimmer, trimer or other polymers.

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. An effector cell can also phagocytose a target antigen, target cell, metastatic cancer cell, or microorganism.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated, e.g., an HPV-related disease. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds. In the methods of the present invention, HPV fusion polypeptide compositions may be administered to a subject having or at risk for having a disease caused by HPV infection. For example, in one embodiment, a "therapeutically effective amount" of a HPV fusion polypeptide may include an amount in which the occurrence of cervical cancer is prevented.

As used herein, "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "HPV fusion polypeptide" refers to a polypeptide comprising an immunostimulatory protein or fragment thereof linked to an protein antigen from human papilloma virus. The linkage may be non-covalent or covalent (e.g., via a peptide bond). In particular embodiments, the protein antigen is the E7 antigen. Exemplary embodiments and domains of the HPV fusion polypeptides may be referred to by abbreviations, as shown in Table 1.

TABLE 1

Abbreviations Used for Exemplary Fusion Protein Constructs

| Abbreviation | Description |
|---|---|
| C6 | N-terminal domain of human CRT (amino acids 18-366, SEQ ID NO: 2) |
| C7 | Full-length human CRT (amino acids 18-417, SEQ ID NO: 2) |
| E7 | Wild-type HPV 16 E7 protein. |
| E7m2 | Mutated E7 with 2 amino acid substitutions. |
| E7m3 | Mutated E7 with 3 amino acid substitutions. |
| C6E7 | Fusion protein of C6 and E7. |
| C6E7m2 | Fusion protein of C6 and mutated E7 with 2 amino acid substitutions. |
| C6E7m3 | Fusion protein of C6 and mutated E7 with 3 amino acid substitutions. |
| C7E7 | Fusion protein of C7 and E7. |
| C7E7m2 | Fusion protein of C7 and mutated E7 with 2 amino acid substitutions. |
| C7E7m3 | Fusion protein of C7 and mutated E7 with 3 amino acid substitutions. |

The term "human papilloma virus related disease" or "HPV-related disease" as used herein, refers to a disease or condition related to human HPV infection including, but not limited to, cervical cancer, anal intraepithelial neoplasia, cervical intraepithelial neoplasia, anogenital warts, recurrent respiratory papillomatosis, and vulval intraepithelial neoplasia.

As used herein, the terms "identical" or percent "identity", when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This term also refers to, or can be applied to, the complement of a test sequence. The term also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An "isolated" or "purified" polypeptide or biologically-active portion thereof is substantially free of cellular material or other contaminating polypeptides from the cell or tissue source from which the HPV fusion polypeptide is derived, or substantially free from chemical precursors or other chemicals when chemically synthesized. For example, an isolated HPV fusion polypeptide would be free of materials that would interfere with diagnostic or therapeutic uses of the agent. Such interfering materials may include enzymes, hormones and other proteinaceous and nonproteinaceous solutes.

As used herein, the term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, malignant melanoma, invading pathogens, cells or tissues infected with pathogens, or, in cases of autoimmunity or pathological inflammation, normal human cells or tissues.

As used herein, the term "immunostimulatory polypeptide" refers to a polypeptide that enhances the immune response against a particular antigen. Immunostimulatory effects include, but are not limited to, those that directly or indirectly enhance cellular or humoral immune responses. Examples of immunostimulatory effects include, but are not limited to, increased antigen-specific antibody production; activation or proliferation of a lymphocyte population such as NK cells, CD4+ T lymphocytes, CD8+ T lymphocytes, macrophages and the like; as well as increased synthesis of Th1 associated immunostimulatory cytokines including, but not limited to, IL-6, IL-12, IL-18, IFN-$\alpha$, -$\beta$. and -$\gamma$, TNF-$\alpha$ and the like. In some embodiments, the immunostimulatory polypeptide is a protein belonging to a super-family of molecular chaperones which facilitate the folding of non-native polypeptides, including, but not limited to, Hsp27, Hsp40, Hsp70, Hsp90, Hsp100, Hsp110 and other small Hsps. In particular embodiments, the immunostimulatory polypeptide is involved in the assembly of MHC class I/peptide complexes in antigen presenting cells, including, but not limited to calreticulin, calnexin, tapasin, and ER60.

As used herein, the term "lymphocyte" means any of the mononuclear, nonphagocytic leukocytes, found in the blood, lymph, and lymphoid tissues, e.g., B and T lymphocytes.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons. In a particular embodiment, the polynucleotide contains polynucleotide sequences from an immunostimulatory protein gene and a mutant HPV E7 antigen.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature. In a particular embodiment, the polypeptide contains polypeptide sequences from an immunostimulatory protein and a mutant HPV E7 antigen.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed or not expressed at all.

As used herein, the term "subject" means that preferably the subject is a mammal, such as a human, but can also be an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the term "substitution" is one of mutations that is generally used in the art. Those substitution variants have at least one amino acid residue in the HPV fusion polypeptide molecule replaced by a different residue. "Conservative substitutions" typically provide similar biological activity as the unmodified polypeptide sequence from which the conservatively modified variant was derived. Conservative substitutions typically include the substitution of one amino acid for another with similar characteristics. Conservative substitution tables providing functionally similar amino acids are well known in the art. For example, the following six groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic (Cationic): Arginine (R), Lysine (K), Histidine (H); Acidic (Anionic): Aspartic acid (D), Glutamic acid (E); Amide: Asparagine (N), Glutamine (Q). Examples of conservative substitutions are shown in the table below under the heading of "preferred substitutions". "Exemplary substitutions" in Table 2 may result in more substantial changes to biological activity.

TABLE 2

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a HPV-related disease, if after receiving a therapeutic amount of the HPV vaccine compositions according to the methods of the present invention, the subject shows observable and/or measurable reduction in or absence of one or more signs and symptoms of HPV-related disease. For example, for HPV-induced cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues.

COMPOSITIONS OF THE PRESENT INVENTION

General. In one aspect, the present invention provides HPV vaccine compositions comprising a fusion protein of an immunostimulatory polypeptide and a mutant HPV E7 antigen useful in the treatment of HPV-related diseases. The present inventors have discovered that mutant E7 antigens are resistant to degradation during storage and show reduced protein aggregation compared to wild-type E7 antigens. The combination also shows an enhanced therapeutic effect in the treatment or prevention of an HPV-related disease.

While not wishing to be limited by theory, it is believed that aggregates form between wild-type E7 polypeptides due to the cross-linking of free cysteine residues within E7 sequence. These polypeptides are also unstable, especially when stored at 4° C. The present inventors have found that certain mutants of E7, which change two or more cysteine residues within the E7 sequence, are resistant to degradation during storage and do not form irreversible protein aggregates compared to wild-type E7 antigens. Thus, the HPV fusion polypeptides of the present invention have the advantage of enhanced stability during storage. Enhanced stability of the HPV fusion polypeptides from the time of manufacture until administration to a subject can provide a more effective treatment compared to a degraded immunologic preparation.

Furthermore, the HPV fusion polypeptides of the present invention are typically expressed in soluble form in recombinant E. coli cells and are not localized to inclusion bodies. Furthermore, fusion proteins comprising the mutant E7 antigens of the present invention typically exhibit immunogenicity greater than or equal to that of the fusion proteins comprising the wild-type E7 antigen.

In some embodiments, the HPV antigen in the constructs of the present invention is an HPV antigen having one or more amino acid substitutions as compared to wild-type. The E7 protein of HPV included in the fusion protein of the present invention can be a full-length sequence of E7 or an immunogenic fragment thereof. The sequence of the full-length E7 antigen is shown in Table 3. As used herein, the term "immunogenic fragment" refers to a fragment which can initiate an immune response and/or enhance an existing immune response in a subject. One skilled in the art can obtain the immunogenic fragment of E7 protein of HPV through conventional immunologic experiments. For example, the fragment can be an E7 protein with its amino terminal and/or carboxyl terminal being truncated by, e.g., from 1 to 30 amino acids, 1 to 20 amino acids, 1 to 10 amino acids, or 1 to 5 amino acids. The fragment can also be any fragment which comprises a human T cell epitope, such as HLA-A*0201 restricted cytotoxic T-lymphocyte epitope peptide, including amino acids 11-20 (YMLDLQPETT, SEQ ID NO: 15), amino acids 86 to 93 (TLGIVCPI, SEQ ID NO: 16) or amino acids 82 to 90 (LLMGTLGIV, SEQ ID NO: 17).

TABLE 3

| Sequence of the HPV E7 (SEQ ID NO: 1) |
| --- |
| MHGDTPTLHEYMLDLQPETTDLYCYEQLNDSSEEEDEIDGPAGQAEPDRA |
| HYNIVTFCCKCDSTLRLCVQSTHVDIRTLEDLLMGTLGIVCPICSQKP |

In some embodiments, the E7 protein or immunogenic fragment used in the HPV fusion polypeptides of the present invention is a mutant HPV antigen. In particular embodiments, two, three, four, five, six, seven or more cysteine residues are substituted with a different amino acid residue, e.g. serine or valine. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned HPV E7 DNA to produce the mutant HPV E7 antigens. In further embodiments, additional amino acid substitutions (i.e., in non-cysteine residues) are made to enhance the solubility of the HPV fusion polypeptide.

In one embodiment, the HPV fusion polypeptide comprises a mutant E7 antigen with two amino acid substitutions at cysteine residues. In one example, referred to herein as "E7m2," two cysteine substitutions were introduced at cysteine-59 and cysteine-68 of SEQ ID NO: 1. In particular embodiments, the substitutions were C59S and C68V. However, substitutions with other aliphatic (e.g., glycine, alanine, valine, leucine, isoleucine) or polar (e.g., serine, threonine, asparagines, and glutamine) amino acids might also be made.

HPV fusion polypeptides comprising the E7m2 antigen exhibits greater stability upon storage without significant irreversible aggregation problems observed with the wild-type E7 antigen.

In one embodiment, the HPV fusion polypeptide comprises a mutant E7 antigen with three amino acid substitutions at cysteine residues. In one example, referred to herein as "E7m3," three cysteine substitutions were introduced at cysteine-24, cysteine-59, and cysteine-68 of SEQ ID NO: 1. In particular embodiments, the substitutions were C24V, C59S, and C68V. However, substitutions with other aliphatic (e.g., glycine, alanine, valine, leucine, isoleucine) or polar (e.g., serine, threonine, asparagines, and glutamine) amino acids might also be made.

In some embodiments, the immunostimulatory polypeptide is a calreticulin (CRT) polypeptide, or a biologically active fragment, domain, variant, or homologue thereof. In suitable embodiments, the immunostimulatory polypeptide comprises the full-length CRT polypeptide (Table 4). In other embodiments the immunostimulatory polypeptide comprises an N-terminal fragment of CRT (referred to herein as "C7"), e.g., a fragment comprising amino acids 18-366 of SEQ ID NO: 2 (referred to herein as "CRT366" or "C6"), or a fragment comprising amino acids 18-180 of SEQ ID NO: 2 (referred to herein as "CRT180").

TABLE 4

| Sequence of the Human CRT (SEQ ID NO: 2) |
| --- |
| MLLSVPLLLGLLGLAVAEPAVYFKEQFLDGDGWTSRWIESKHKSDFGKFV |
| LSSGKFYGDEEKDKGLQTSQDARFYALSASFEPFSNKGQTLVVQFTVKHE |
| QNIDCGGGYVKLFPNSLDQTDMHGDSEYNIMFGPDICGPGTKKVHVIFNY |
| KGKNVLINKDIRCKDDEFTHLYTLIVRPDNTYEVKIDNSQVESGSLEDDW |
| DFLPPKKIKDPDASKPEDWDERAKIDDPTDSKPEDWDKPEHIPDPDAKKP |
| EDWDEEMDGEWEPPVIQNPEYKGEWKPRQIDNPDYKGTWIHPEIDNPEYS |
| PDPSIYAYDNFGVLGLDLWQVKSGTIFDNFLITNDEAYAEEFGNETWGVT |
| KAAEKQMKDKQDEEQRLKEEEEDKKRKEEEEAEDKEDDEDKDEDEEDEED |
| KEEDEEEDVPGQAKDEL |

To generate the HPV fusion polypeptides of the present invention, the immunostimulatory polypeptide is linked to the mutant HPV E7 antigen. The two polypeptides may be linked in either orientation. In one embodiment, the immunostimulatory polypeptide is linked to the N-terminus of the mutant E7 antigen. In another embodiment, the immunostimulatory polypeptide is linked to the C-terminus of the E7 antigen. The polypetides may be linked by either covalent or non-covalent attachment. In one embodiment, the polypetides are linked covalently via a peptide bond. For example, the fusion polypeptide may be synthesized by expressing a nucleic acid encoding the fusion polypeptide as a single open reading frame.

In one embodiment, the N-terminal domain (e.g., amino acids 18-366 of SEQ ID NO: 2, abbreviated as C6) of human CRT is linked to the HPV-16 E7 antigen to form the C6E7 fusion protein. The nucleotide sequence encoding C6E7 is shown in Table 5. In this embodiment, the codons have been optimized for expression in E. coli. The amino acid sequence of C6E7 is shown in Table 6.

TABLE 5

Sequence of Polynucleotide Encoding C6E7 (SEQ ID NO: 3)

ATGGAGCCTGCCGTCTACTTCAAGGAGCAGTTTCTGGACGGAGACGGGTG
GACTTCCCGCTGGATCGAATCCAAACACAAGTCAGATTTTGGCAAATTCG
TTCTCAGTTCCGGCAAGTTCTACGGTGACGAGGAGAAAGATAAAGGTTTG
CAGACAAGCCAGGATGCACGCTTTTATGCTCTGTCGGCCAGTTTCGAGCC
TTTCAGCAACAAAGGCCAGACGCTGGTGGTGCAGTTCACGGTGAAACATG
AGCAGAACATCGACTGTGGGGGCGGCTATGTGAAGCTGTTTCCTAATAGT
TTGGACCAGACAGACATGCACGGAGACTCAGAATACAACATCATGTTTGG
TCCCGACATCTGTGGCCCTGGCACCAAGAAGGTTCATGTCATCTTCAACT
ACAAGGGCAAGAACGTGCTGATCAACAAGGACATCCGTTGCAAGGATGAT
GAGTTTACACACCTGTACACACTGATTGTGCGGCCAGACAACACCTATGA
GGTGAAGATTGACAACAGCCAGGTGGAGTCCGGCTCCTTGGAAGACGATT
GGGACTTCCTGCCACCCAAGAAGATAAAGGATCCTGATGCTTCAAAACCG
GAAGACTGGGATGAGCGGGCCAAGATCGATGATCCCACAGACTCCAAGCC
TGAGGACTGGGACAAGCCCGAGCATATCCCTGACCCTGATGCTAAGAAGC
CCGAGGACTGGGATGAAGAGATGGACGGAGAGTGGGAACCCCCAGTGATT
CAGAACCCTGAGTACAAGGGTGAGTGGAAGCCCCGGCAGATCGACAACCC
AGATTACAAGGGCACTTGGATCCACCCAGAAATTGACAACCCCGAGTATT
CTCCCGATCCCAGTATCTATGCCTATGATAACTTTGGCGTGCTGGGCCTG
GACCTCTGGCAGGTCAAGTCTGGCACCATCTTTGACAACTTCCTCATCAC
CAACGATGAGGCATACGCTGAGGAGTTTGGCAACGAGACGTGGGGCGTAA
CAAAGGCAGCAGAGAAACAAATGAAGGACAAACAGGACGAGGAGCAGAGG
GTCGACATGCATGGTGATACTCCGACTCTTCATGAATATATGCTGGATCT
GCAACCGGAAACTACTGATCTGTACTGTTATGAACAACTGAATGATAGCT
CTGAAGAGGAAGATGAAATTGATGGTCCAGCTGGTCAAGCAGAACCGGAT
CGTGCTCATTATAATATTGTAACTTTTTGTTGTAAATGTGATTCTACTCT
GCGTCTGTGTGTACAAAGCACTCATGTTGATATTCGTACTCTGGAAGATC
TGCTTATGGGTACTCTGGGTATTGTTTGTCCGATTTGTTCTCAGAAACCA
TAA

TABLE 6

Sequence of the C6E7 Polypeptide (SEQ ID NO: 4)

MEPAVYFKEQFLDGDGWTSRWIESKHKSDFGKFVLSSGKFYGDEEKDKGL
QTSQDARFYALSASFEPFSNKGQTLVVQFTVKHEQNIDCGGGYVKLFPNS
LDQTDMHGDSEYNIMFGPDICGPGTKKVHVIFNYKGKNVLINKDIRCKDD
EFTHLYTLIVRPDNTYEVKIDNSQVESGSLEDDWDFLPPKKIKDPDASKP
EDWDERAKIDDPTDSKPEDWDKPEHIPDPDAKKPEDWDEEMDGEWEPPVI
QNPEYKGEWKPRQIDNPDYKGTWIHPEIDNPEYSPDPSIYAYDNFGVLGL
DLWQVKSGTIFDNFLITNDEAYAEEFGNETWGVTKAAEKQMKDKQDEEQR

TABLE 6-continued

Sequence of the C6E7 Polypeptide (SEQ ID NO: 4)

VDMHGDTPTLHEYMLDLQPETTDLYCYEQLNDSSEEEDEIDGPAGQAEPD
RAHYNIVTFCCKCDSTLRLCVQSTHVDIRTLEDLLMGTLGIVCPICSQKP

In one embodiment, the N-terminal domain (e.g., amino acids 18-366 of SEQ ID NO: 2, abbreviated as C6) of human CRT is linked to the HPV-16 E7m2 antigen to form the C6E7m2 fusion protein. The nucleotide sequence encoding C6E7m2 is shown in Table 7. The amino acid sequence of C6E7 is shown in Table 8.

TABLE 7

Sequence of Polynucleotide Encoding C6E7m2 (SEQ ID NO: 5)

ATGGAGCCTGCCGTCTACTTCAAGGAGCAGTTTCTGGACGGAGACGGGTG
GACTTCCCGCTGGATCGAATCCAAACACAAGTCAGATTTTGGCAAATTCG
TTCTCAGTTCCGGCAAGTTCTACGGTGACGAGGAGAAAGATAAAGGTTTG
CAGACAAGCCAGGATGCACGCTTTTATGCTCTGTCGGCCAGTTTCGAGCC
TTTCAGCAACAAAGGCCAGACGCTGGTGGTGCAGTTCACGGTGAAACATG
AGCAGAACATCGACTGTGGGGGCGGCTATGTGAAGCTGTTTCCTAATAGT
TTGGACCAGACAGACATGCACGGAGACTCAGAATACAACATCATGTTTGG
TCCCGACATCTGTGGCCCTGGCACCAAGAAGGTTCATGTCATCTTCAACT
ACAAGGGCAAGAACGTGCTGATCAACAAGGACATCCGTTGCAAGGATGAT
GAGTTTACACACCTGTACACACTGATTGTGCGGCCAGACAACACCTATGA
GGTGAAGATTGACAACAGCCAGGTGGAGTCCGGCTCCTTGGAAGACGATT
GGGACTTCCTGCCACCCAAGAAGATAAAGGATCCTGATGCTTCAAAACCG
GAAGACTGGGATGAGCGGGCCAAGATCGATGATCCCACAGACTCCAAGCC
TGAGGACTGGGACAAGCCCGAGCATATCCCTGACCCTGATGCTAAGAAGC
CCGAGGACTGGGATGAAGAGATGGACGGAGAGTGGGAACCCCCAGTGATT
CAGAACCCTGAGTACAAGGGTGAGTGGAAGCCCCGGCAGATCGACAACCC
AGATTACAAGGGCACTTGGATCCACCCAGAAATTGACAACCCCGAGTATT
CTCCCGATCCCAGTATCTATGCCTATGATAACTTTGGCGTGCTGGGCCTG
GACCTCTGGCAGGTCAAGTCTGGCACCATCTTTGACAACTTCCTCATCAC
CAACGATGAGGCATACGCTGAGGAGTTTGGCAACGAGACGTGGGGCGTAA
CAAAGGCAGCAGAGAAACAAATGAAGGACAAACAGGACGAGGAGCAGAGG
GTCGACATGCATGGTGATACTCCGACTCTTCATGAATATATGCTGGATCT
GCAACCGGAAACTACTGATCTGTACTGTTATGAACAACTGAATGATAGCT
CTGAAGAGGAAGATGAAATTGATGGTCCAGCTGGTCAAGCAGAACCGGAT
CGTGCTCATTATAATATTGTAACTTTTTGTTCTAAATGTGATTCTACTCT
GCGTCTGGTTGTACAAAGCACTCATGTTGATATTCGTACTCTGGAAGATC
TGCTTATGGGTACTCTGGGTATTGTTTGTCCGATTTGTTCTCAGAAACCA
TAA

TABLE 8

Sequence of the C6E7m2 Polypeptide (SEQ ID NO: 6)

MEPAVYFKEQFLDGDGWTSRWIESKHKSDFGKFVLSSGKFYGDEEKDKGL
QTSQDARFYALSASFEPFSNKGQTLVVQFTVKHEQNIDCGGGYVKLFPNS
LDQTDMHGDSEYNIMFGPDICGPGTKKVHVIFNYKGKNVLINKDIRCKDD
EETHLYTLIVRPDNTYEVKIDNSQVESGSLEDDWDFLPPKKIKDPDASKP
EDWDERAKIDDPTDSKPEDWDKPEHIPDPDAKKPEDWDEEMDGEWEPPVI
QNPEYKGEWKPRQIDNPDYKGTWIHPEIDNPEYSPDPSIYAYDNFGVLGL
DLWQVKSGTIFDNFLITNDEAYAEEFGNETWGVTKAAEKQMKDKQDEEQR
VDMHGDTPTLHEYMLDLQPETTDLYCYEQLNDSSEEEDEIDGPAGQAEPD
RAHYNIVTFCSKCDSTLRLVVQSTHVDIRTLEDLLMGTLGIVCPICSQKP

In one embodiment, the N-terminal domain (e.g., amino acids 18-366 of SEQ ID NO: 2, abbreviated as C6) of human CRT is linked to the HPV-16 E7m3 antigen to form the C6E7m3 fusion protein. The nucleotide sequence encoding C6E7m3 is shown in Table 9. The amino acid sequence of C6E7 is shown in Table 10.

TABLE 9

Sequence of Polynucleotide Encoding C6E7m3 (SEQ ID NO: 7)

ATGGAGCCTGCCGTCTACTTCAAGGAGCAGTTTCTGGACGGAGACGGGTG
GACTTCCCGCTGGATCGAATCCAAACACAAGTCAGATTTTGGCAAATTCG
TTCTCAGTTCCGGCAAGTTCTACGGTGACGAGGAGAAAGATAAAGGTTTG
CAGACAAGCCAGGATGCACGCTTTTATGCTCTGTCGGCCAGTTTCGAGCC
TTTCAGCAACAAAGGCCAGACGCTGGTGGTGCAGTTCACGGTGAAACATG
AGCAGAACATCGACTGTGGGGGCGGCTATGTGAAGCTGTTTCCTAATAGT
TTGGACCAGACAGACATGCACGGAGACTCAGAATACAACATCATGTTTGG
TCCCGACATCTGTGGCCCTGGCACCAAGAAGGTTCATGTCATCTTCAACT
ACAAGGGCAAGAACGTGCTGATCAACAAGGACATCCGTTGCAAGGATGAT
GAGTTTACACACCTGTACACACTGATTGTGCGGCCAGACAACACCTATGA
GGTGAAGATTGACAACAGCCAGGTGGAGTCCGGCTCCTTGGAAGACGATT
GGGACTTCCTGCCACCCAAGAAGATAAAGGATCCTGATGCTTCAAAACCG
GAAGACTGGGATGAGCGGGCCAAGATCGATGATCCCACAGACTCCAAGCC
TGAGGACTGGGACAAGCCCGAGCATATCCCTGACCCTGATGCTAAGAAGC
CCGAGGACTGGGATGAAGAGATGGACGGAGAGTGGGAACCCCCAGTGATT
CAGAACCCTGAGTACAAGGGTGAGTGGAAGCCCCGGCAGATCGACAACCC
AGATTACAAGGGCACTTGGATCCACCCAGAAATTGACAACCCCGAGTATT
CTCCCGATCCCAGTATCTATGCCTATGATAACTTTGGCGTGCTGGGCCTG
GACCTCTGGCAGGTCAAGTCTGGCACCATCTTTGACAACTTCCTCATCAC
CAACGATGAGGCATACGCTGAGGAGTTTGGCAACGAGACGTGGGGCGTAA
CAAAGGCAGCAGAGAAACAAATGAAGGACAAACAGGACGAGGAGCAGAGG
GTCGACATGCATGGTGATACTCCGACTCTTCATGAATATATGCTGGATCT
GCAACCGGAAACTACTGATCTGTACGTTTATGAACAACTGAATGATAGCT

TABLE 9-continued

Sequence of Polynucleotide Encoding C6E7m3 (SEQ ID NO: 7)

CTGAAGAGGAAGATGAAATTGATGGTCCAGCTGGTCAAGCAGAACCGGAT
CGTGCTCATTATAATATTGTAACTTTTTGTTCTAAATGTGATTCTACTCT
GCGTCTGGTTGTACAAAGCACTCATGTTGATATTCGTACTCTGGAAGATC
TGCTTATGGGTACTCTGGGTATTGTTTGTCCGATTTGTTCTCAGAAACCA
TAA

TABLE 10

Sequence of the C6E7m3 Polypeptide (SEQ ID NO: 8)

MEPAVYFKEQFLDGDGWTSRWIESKHKSDFGKFVLSSGKFYGDEEKDKGL
QTSQDARFYALSASFEPFSNKGQTLVVQFTVKHEQNIDCGGGYVKLFPNS
LDQTDMHGDSEYNIMFGPDICGPGTKKVHVIFNYKGKNVLINKDIRCKDD
EFTHLYTLIVRPDNTYEVKIDNSQVESGSLEDDWDFLPPKKIKDPDASKP
EDWDERAKIDDPTDSKPEDWDKPEHIPDPDAKKPEDWDEEMDGEWEPPVI
QNPEYKGEWKPRQIDNPDYKGTWIHPEIDNPEYSPDPSIYAYDNFGVLGL
DLWQVKSGTIFDNFLITNDEAYAEEFGNETWGVTKAAEKQMKDKQDEEQR
VDMHGDTPTLHEYMLDLQPETTDLYVYEQLNDSSEEEDEIDGPAGQAEPD
RAHYNIVTFCSKCDSTLRLVVQSTHVDIRTLEDLLMGTLGIVCPICSQKP

In one embodiment, the full-length human CRT (SEQ ID NO: 2, abbreviated as C7) is linked to the HPV-16 E7 antigen to form the C7E7 fusion protein. The nucleotide sequence encoding C7E7 is shown in Table 11. The amino acid sequence of C7E7 is shown in Table 12.

TABLE 11

Sequence of Polynucleotide Encoding C7E7 (SEQ ID NO: 9)

ATGGAGCCTGCCGTCTACTTCAAGGAGCAGTTTCTGGACGGAGACGGGTG
GACTTCCCGCTGGATCGAATCCAAACACAAGTCAGATTTTGGCAAATTCG
TTCTCAGTTCCGGCAAGTTCTACGGTGACGAGGAGAAAGATAAAGGTTTG
CAGACAAGCCAGGATGCACGCTTTTATGCTCTGTCGGCCAGTTTCGAGCC
TTTCAGCAACAAAGGCCAGACGCTGGTGGTGCAGTTCACGGTGAAACATG
AGCAGAACATCGACTGTGGGGGCGGCTATGTGAAGCTGTTTCCTAATAGT
TTGGACCAGACAGACATGCACGGAGACTCAGAATACAACATCATGTTTGG
TCCCGACATCTGTGGCCCTGGCACCAAGAAGGTTCATGTCATCTTCAACT
ACAAGGGCAAGAACGTGCTGATCAACAAGGACATCCGTTGCAAGGATGAT
GAGTTTACACACCTGTACACACTGATTGTGCGGCCAGACAACACCTATGA
GGTGAAGATTGACAACAGCCAGGTGGAGTCCGGCTCCTTGGAAGACGATT
GGGACTTCCTGCCACCCAAGAAGATAAAGGATCCTGATGCTTCAAAACCG
GAAGACTGGGATGAGCGGGCCAAGATCGATGATCCCACAGACTCCAAGCC
TGAGGACTGGGACAAGCCCGAGCATATCCCTGACCCTGATGCTAAGAAGC
CCGAGGACTGGGATGAAGAGATGGACGGAGAGTGGGAACCCCCAGTGATT

TABLE 11-continued

Sequence of Polynucleotide Encoding C7E7 (SEQ ID NO: 9)

CAGAACCCTGAGTACAAGGGTGAGTGGAAGCCCCGGCAGATCGACAACCC
AGATTACAAGGGCACTTGGATCCACCCAGAAATTGACAACCCCGAGTATT
CTCCCGATCCCAGTATCTATGCCTATGATAACTTTGGCGTGCTGGGCCTG
GACCTCTGGCAGGTCAAGTCTGGCACCATCTTTGACAACTTCCTCATCAC
CAACGATGAGGCATACGCTGAGGAGTTTGGCAACGAGACGTGGGGCGTAA
CAAAGGCAGCAGAGAAACAAATGAAGGACAAACAGGACGAGGAGCAGAGG
CTTAAGGAGGAGGAAGAAGACAAGAAACGCAAAGAGGAGGAGGAGGCAGA
GGACAAGGAGGATGATGAGGACAAAGATGAGGATGAGGAGGATGAGGAGG
ACAAGGAGGAAGATGAGGAGGAAGATGTCCCCGGCCAGGCCAAGGACGAG
CTGGTCGACATGCATGGTGATACTCCGACTCTTCATGAATATATGCTGGA
TCTGCAACCGGAAACTACTGATCTGTACTGTTATGAACAACTGAATGATA
GCTCTGAAGAGGAAGATGAAATTGATGGTCCAGCTGGTCAAGCAGAACCG
GATCGTGCTCATTATAATATTGTAACTTTTTGTTGTAAATGTGATTCTAC
TCTGCGTCTGTGTGTACAAAGCACTCATGTTGATATTCGTACTCTGGAAG
ATCTGCTTATGGGTACTCTGGGTATTGTTTGTCCGATTTGTTCTCAGAAA
CCATAA

TABLE 12

Sequence of the C7E7 Polypeptide (SEQ ID NO: 10)

MEPAVYFKEQFLDGDGWTSRWIESKNKSDFGKFVLSSGKFYGDEEKDKGL
QTSQDARFYALSASFEPFSNKGQTLVVQFTVKHEQNIDCGGGYVKLFPNS
LDQTDMHGDSEYNIMFGPDICGPGTKKVHVIFNYKGKNVLINKDIRCKDD
EFTHLYTLIVRPDNTYEVKIDNSQVESGSLEDDWDFLPPKKIKDPDASKP
EDWDEPAKIDDPTDSKPEDWDKPEHIPDPDAKKPEDWDEEMDGEWEPPVI
QNPEYKGEWKPRQIDNPDYKGTWIHPEIDNPEYSPDPSIYAYDNFGVLGL
DLWQVKsGTIFDNFLITNDEAYAEEFGNETwGvTKAAEKQMKDKQDEEQR
LKEEEEDKKRKEEEEAEDKEDDEDKDEDEEDEEDKEEDEEEDVPGQAKDE
LVDMHGDTPTLHEYMLDLQPETTDLYCYEQLNDSSEEEDEIDGPAGQAEP
DRAHYNIVTFCCKCDSTLRLCVQSTHVDIRTLEDLLMGTLGIVCPICSQK
P

In one embodiment, the full-length human CRT (SEQ ID NO: 2, abbreviated as C7) is linked to the HPV-16 E7m2 antigen to form the C7E7m2 fusion protein. The nucleotide sequence encoding C7E7m2 is shown in Table 13. The amino acid sequence of C7E7m2 is shown in Table 14.

TABLE 13

Sequence of Polynucleotide Encoding C7E7m2 (SEQ ID NO: 11)

ATGGAGCCTGCCGTCTACTTCAAGGAGCAGTTTCTGGACGGAGACGGGTG
GACTTCCCGCTGGATCGAATCCAAACACAAGTCAGATTTTGGCAAATTCG

TABLE 13-continued

Sequence of Polynucleotide Encoding C7E7m2 (SEQ ID NO: 11)

TTCTCAGTTCCGGCAAGTTCTACGGTGACGAGGAGAAAGATAAAGGTTTG
CAGACAAGCCAGGATGCACGCTTTTATGCTCTGTCGGCCAGTTTCGAGCC
TTTCAGCAACAAAGGCCAGACGCTGGTGGTGCAGTTCACGGTGAAACATG
AGCAGAACATCGACTGTGGGGGCGGCTATGTGAAGCTGTTTCCTAATAGT
TTGGACCAGACAGACATGCACGGAGACTCAGAATACAACATCATGTTTGG
TCCCGACATCTGTGGCCCTGGCACCAAGAAGGTTCATGTCATCTTCAACT
ACAAGGGCAAGAACGTGCTGATCAACAAGGACATCCGTTGCAAGGATGAT
GAGTTTACACACCTGTACACACTGATTGTGCGGCCAGACAACACCTATGA
GGTGAAGATTGACAACAGCCAGGTGGAGTCCGGCTCCTTGGAAGACGATT
GGGACTTCCTGCCACCCAAGAAGATAAAGGATCCTGATGCTTCAAAACCG
GAAGACTGGGATGAGCGGGCCAAGATCGATGATCCCACAGACTCCAAGCC
TGAGGACTGGGACAAGCCCGAGCATATCCCTGACCCTGATGCTAAGAAGC
CCGAGGACTGGGATGAAGAGATGGACGGAGAGTGGGAACCCCCAGTGATT
CAGAACCCTGAGTACAAGGGTGAGTGGAAGCCCCGGCAGATCGACAACCC
AGATTACAAGGGCACTTGGATCCACCCAGAAATTGACAACCCCGAGTATT
CTCCCGATCCCAGTATCTATGCCTATGATAACTTTGGCGTGCTGGGCCTG
GACCTCTGGCAGGTCAAGTCTGGCACCATCTTTGACAACTTCCTCATCAC
CAACGATGAGGCATACGCTGAGGAGTTTGGCAACGAGACGTGGGGCGTAA
CAAAGGCAGCAGAGAAACAAATGAAGGACAAACAGGACGAGGAGCAGAGG
CTTAAGGAGGAGGAAGAAGACAAGAAACGCAAAGAGGAGGAGGAGGCAGA
GGACAAGGAGGATGATGAGGACAAAGATGAGGATGAGGAGGATGAGGAGG
ACAAGGAGGAAGATGAGGAGGAAGATGTCCCCGGCCAGGCCAAGGACGAG
CTGGTCGACATGCATGGTGATACTCCGACTCTTCATGAATATATGCTGGA
TCTGCAACCGGAAACTACTGATCTGTACTGTTATGAACAACTGAATGATA
GCTCTGAAGAGGAAGATGAAATTGATGGTCCAGCTGGTCAAGCAGAACCG
GATCGTGCTCATTATAATATTGTAACTTTTTGTTCTAAATGTGATTCTAC
TCTGCGTCTGGTTGTACAAAGCACTCATGTTGATATTCGTACTCTGGAAG
ATCTGCTTATGGGTACTCTGGGTATTGTTTGTCCGATTTGTTCTCAGAAA
CCATAA

TABLE 14

Sequence of the C7E7m2 Polypeptide (SEQ ID NO: 12)

MEPAVYFKEQFLDGDGWTSRWIESKHKSDFGKFVLSSGKFYGDEEKDKGL
QTSQDARFYALSASFEPFSNKGQTLVVQFTVKNEQNIDCGGGYVKLFPNS
LDQTDMHGDSEYNIMFGPDICGPGTKKVHVIFNYKGKNVLINKDIRCKDD
EFTHLYTLIVRPDNTYEVKIDNSQVESGSLEDDWDFLPPKKIKDPDASKP
EDWDERAKIDDPTDSKPEDWDKPEHIPDPDAKKPEDWDEEMDGEWEPPVI
QNPEYKGEWKPRQIDNPDYKGTWIHPEIDNPEYSPDPSIYAYDNFGVLGL

TABLE 14-continued

Sequence of the C7E7m2 Polypeptide (SEQ ID NO: 12)

DLWQVKSGTIFDNFLITNDEAYAEEFGNETWGVTKAAEKQMKDKQDEEQR

LKEEEEDKKRKEEEEAEDKEDDEDKDEDEEDEEDKEEDEEEDVPGQAKDE

LVDMHGDTPTLHEYMLDLQPETTDLYCYEQLNDSSEEEDEIDGPAGQAEP

DRAHYNIVTFCSKCDSTLRLVVQSTHVDIRTLEDLLMGTLGIVCPICSQK

P

In one embodiment, the full-length human CRT (SEQ ID NO: 2, abbreviated as C7) is linked to the HPV-16 E7 antigen to form the C7E7m3 fusion protein. The nucleotide sequence encoding C7E7m3 is shown in Table 15. The amino acid sequence of C7E7m3 is shown in Table 16

TABLE 15

Sequence of Polynucleotide Encoding C7E7m3 (SEQ ID NO: 13)

ATGGAGCCTGCCGTCTACTTCAAGGAGCAGTTTCTGGACGGAGACGGGTG

GACTTCCCGCTGGATCGAATCCAAACACAAGTCAGATTTTGGCAAATTCG

TTCTCAGTTCCGGCAAGTTCTACGGTGACGAGGAGAAAGATAAAGGTTTG

CAGACAAGCCAGGATGCACGCTTTTATGCTCTGTCGGCCAGTTTCGAGCC

TTTCAGCAACAAAGGCCAGACGCTGGTGGTGCAGTTCACGGTGAAACATG

AGCAGAACATCGACTGTGGGGGCGGCTATGTGAAGCTGTTTCCTAATAGT

TTGGACCAGACAGACATGCACGGAGACTCAGAATACAACATCATGTTTGG

TCCCGACATCTGTGGCCCTGGCACCAAGAAGGTTCATGTCATCTTCAACT

ACAAGGGCAAGAACGTGCTGATCAACAAGGACATCCGTTGCAAGGATGAT

GAGTTTACACACCTGTACACACTGATTGTGCGGCCAGACAACACCTATGA

GGTGAAGATTGACAACAGCCAGGTGGAGTCCGGCTCCTTGGAAGACGATT

GGGACTTCCTGCCACCCAAGAAGATAAAGGATCCTGATGCTTCAAAACCG

GAAGACTGGGATGAGCGGGCCAAGATCGATGATCCCACAGACTCCAAGCC

TGAGGACTGGGACAAGCCCGAGCATATCCCTGACCCTGATGCTAAGAAGC

CCGAGGACTGGGATGAAGAGATGGACGGAGAGTGGGAACCCCCAGTGATT

CAGAACCCTGAGTACAAGGGTGAGTGGAAGCCCCGGCAGATCGACAACCC

AGATTACAAGGGCACTTGGATCCACCCAGAAATTGACAACCCCGAGTATT

CTCCCGATCCCAGTATCTATGCCTATGATAACTTTGGCGTGCTGGGCCTG

GACCTCTGGCAGGTCAAGTCTGGCACCATCTTTGACAACTTCCTCATCAC

CAACGATGAGGCATACGCTGAGGAGTTTGGCAACGAGACGTGGGGCGTAA

CAAAGGCAGCAGAGAAACAAATGAAGGACAAACAGGACGAGGAGCAGAGG

CTTAAGGAGGAGGAAGAAGACAAGAAACGAAAGAGGAGGAGGAGGCAGA

GGACAAGGAGGATGATGAGGACAAAGATGAGGATGAGGAGGATGAGGAGG

ACAAGGAGGAAGATGAGGAGGAAGATGTCCCCGGCCAGGCCAAGGACGAG

CTGGTCGACATGCATGGTGATACTCCGACTCTTCATGAATATATGCTGGA

TCTGCAACCGGAAACTACTGATCTGTACGTTTATGAACAACTGAATGATA

GCTCTGAAGAGGAAGATGAAATTGATGGTCCAGCTGGTCAAGCAGAACCG

TABLE 15-continued

Sequence of Polynucleotide Encoding C7E7m3 (SEQ ID NO: 13)

GATCGTGCTCATTATAATATTGTAACTTTTTGTTCTAAATGTGATTCTAC

TCTGCGTCTGGTTGTACAAAGCACTCATGTTGATATTCGTACTCTGGAAG

ATCTGCTTATGGGTACTCTGGGTATTGTTTGTCCGATTTGTTCTCAGAAA

CCATAA

TABLE 16

Sequence of the C7E7m3 Polypeptide (SEQ ID NO: 14)

MEPAVYFKEQFLDGDGWTSRWIESKHISDFGKFVLSSGKFYGDEEKDKGL

QTSQDARFYALSASFEPFSNKGQTLVVQFTVKHEQNIDCGGGYVKLFPNS

LDQTDMHGDSEYNIMFGPDICGPGTKKVHVIFNYKGKNVLINKDIRCKDD

EFTHLYTLIVRPDNTYEVKIDNSQVESGSLEDDWDFLPPKKIKDPDASKP

EDWDERAKIDDPTDSKPEDWDKPEHIPDPDAKKPEDWDEEMDGEWEPPVI

QNPEYKGEWKPRQIDNPDYKGTWIHPEIDNPEYSPDPSIYAYDNFGVLGL

DLWQVKSGTIFDNFLITNDEAYAEEFGNETWGVTKAAEKQMKDKQDEEQR

LKEEEEDKKRKEEEEAEDKEDDEDKDEDEEDEEDKEEDEEEDVPGQAKDE

LVDMHGDTPTLHEYMLDLQPETTDLYVYEQLNDSSEEEDEIDGPAGQAEP

DRAHYNIVTFCSKCDSTLRLVVQSTHVDIRTLEDLLMGTLGIVCPICSQK

P

Immunostimulatory Proteins

General. In some embodiments, the HPV fusion polypeptides of the present invention comprise an immunostimulatory polypeptide designed to enhance the immunogenicity of the mutant HPV E7 antigen attached thereto. In one embodiment, the immunostimulatory protein has a chaperone function. While not wishing to be limited by theory, proteins having a chaperone function assist in the correct folding of other proteins in the ER. In particular, some chaperones may assist in the assembly of MHC class I molecules. In some embodiments, the immunostimulatory polypeptide is a protein belonging to a super-family of molecular chaperones that facilitate the folding of non-native polypeptides, including, but not limited to, Hsp27, Hsp40, Hsp70, Hsp90, Hsp100, Hsp110 and other small Hsps. In particular embodiments, the immunostimulatory polypeptide is involved in the assembly of MHC class I/peptide complexes in antigen presenting cells, including, but not limited to calreticulin, calnexin, tapasin, and ER60.

In a particular embodiment, the immunostimulatory polypeptide comprises calreticulin or a biologically active fragment, domain, variant, or homologue thereof. Calreticulin (CRT) is a soluble $Ca^{2+}$-binding protein, which was initially isolated from rabbit endoplasmic reticulum (ER) (Ostwald and MacLennan, *J Biol Chem,* 1974, 249 (3):974-979). CRT protein, encoded by a single gene, exists ubiquitously in animals and higher plants. Human CRT gene is located on chromosome 19 (p13. 32p13. 2) and is 3.6 kb in length. It contains 9 exons and is highly conserved during the evolutionary process. Human CRT is about 46 kD, consisting of a hydrophobic signal peptide sequence of 17 amino acids and 3 functional domains: a highly conserved N-domain (amino acids 18-180 of SEQ ID NO: 2), an acidic C-domain (amino acids 291-400 of SEQ ID NO: 2) and a proline-rich P-domain (amino acids 181-290 of SEQ ID NO: 2). CRT was initially thought as an endoplasmic reticulum/sarcoplasmic reticulum protein involved in protein processing and the regulation of intracellular $Ca^{2+}$ concentration. Recently, it was found that CRT also had an antigen presentation function, and played a critical role in inducing antigen-specific cellular immunity (Basu and Srivastava. *J. Exp. Med.* 1999, 189(5):797-802). In the endoplasmic reticulum, CRT could bind to peptides which were transported into the endoplasmic reticulum through transporters that were associated with antigen processing (TAP-1 and TAP-2) and to β2 microglobulin of MHC class I molecules to assist antigen presentation (Spee and Neefjes, *J. Immunol.* 1997, 27(9):2441-2449; Sadasivan et al., *Immunity* 1996, 5(2):103-114). A complex of an exogenous CRT and a polypeptide could lead to a peptide-specific CD8+ T cell response; a complex of a CRT and a peptide purified from a tumor extract has a specific killing effect on the original tumor (Basu and Srivastava. *J. Exp. Med.* 1999, 189(5):797-802).

In some embodiments, the immunostimulatory comprises a biologically active fragment, domain, variant, or homologue of the native protein. A biologically active fragment, domain, variant, or homologue typically retains the immunostimulatory activity of the native protein. These activities include, but are not limited to (a) forming complexes with peptides in vitro; (b) when expressed in a cell, participating in folding and assembly of nascent glycoproteins, (c) when expressed in a cell, associating with peptides transported into the endoplasmic reticulum by transporters that are associated with antigen processing, and/or (d) inhibiting angiogenesis.

Methods of Preparing Vaccine Compositions of the Present Invention

General. The HPV fusion polypeptides of the present invention can be produced through the application of recombinant DNA technology. Recombinant polynucleotide constructs encoding a HPV fusion polypeptide of the present invention typically include an expression control sequence operably-linked to the coding sequences of HPV fusion polypeptide, including naturally-associated or heterologous promoter regions. As such, another aspect of the invention includes vectors containing one or more nucleic acid sequences encoding a HPV fusion polypeptide of the present invention. For recombinant expression of one or more the polypeptides of the invention, the nucleic acid containing all or a portion of the nucleotide sequence encoding the HPV fusion polypeptide is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160; 6,680,192.

In general, expression vectors useful in recombinant DNA techniques are often in the form of plasmids. In the present specification, "plasmid" and "vector" can be used interchangeably as the plasmid is the most commonly used form of vector. However, the invention is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression in that subject of a compound. Preferably, the expression control sequences are eukaryotic promoter systems in vectors capable of transforming or transfecting eukaryotic cells. Once the vector has been incorporated into the appropriate host, the host is maintained under conditions suitable for high level expression of the nucleotide sequences encoding the HPV fusion polypeptide, and the collection and purification of the HPV fusion polypeptide. See generally, U.S. Patent Publication No. 20020199213. These expression vectors are typically replicable in the host organisms either as episomes or as an integral part of the host chromosomal DNA. Commonly, expression vectors contain selection markers, e.g., ampicillin-resistance or kanamycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the invention comprise a nucleic acid encoding a HPV fusion polypeptide in a form suitable for expression of the nucleic acid in a host cell, which means that the recombinant expression vectors include one or more regulatory sequences, selected on the basis of the host cells to be used for expression that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., HPV fusion polypeptides), include, e.g., but are not limited to, 3-phosphoglycerate kinase and other glycolytic enzymes. Inducible yeast promoters include, among others, promoters from alcohol dehydrogenase, isocytochrome C, and enzymes responsible for maltose and galactose utilization. The expression vectors of the invention can be introduced into host cells to thereby produce polypeptides or peptides, including fusion polypeptides, encoded by nucleic acids as described herein (e.g., C6E7m2, C6E7m3, C7E7m2, C7E7m3, etc.).

Another aspect of the invention pertains to HPV fusion polypeptide-expressing host cells, which contain a nucleic acid encoding one or more HPV fusion polypeptides. The recombinant expression vectors of the invention can be designed for expression of a HPV fusion polypeptide in prokaryotic or eukaryotic cells. For example, a HPV fusion polypeptide can be expressed in bacterial cells such as *Escherichia coli*, insect cells (using baculovirus expression vectors), fungal cells, e.g., yeast, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g. using T7 promoter regulatory sequences and T7 polymerase.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) Gene 69: 301-315), and pET11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., a HPV fusion polypeptide, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (see, e.g., Wada, et al., 1992. Nucl. Acids Res. 20: 2111-2118). Such alteration of nucleic acid sequences of the invention can be carried out by standard DNA synthesis techniques.

In another embodiment, the HPV fusion polypeptide expression vector is a yeast expression vector. Examples of vectors for expression in yeast *Saccharomyces cerivisae* include pYepSec1 (Baldari, et al., 1987. EMBO J. 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif.), and picZ (InVitrogen Corp, San Diego, Calif.). Alternatively, a HPV fusion polypeptide can be expressed in insect cells using baculovirus expression vectors. Baculovirus vectors available for expression of polypeptides, e.g., HPV fusion polypeptide, in cultured insect cells (e.g., SF9 cells) include the pAc series (Smith, et al., *Mol. Cell. Biol.* 3: 2156-2165, 1983) and the pVL series (Lucklow and Summers, 1989. *Virology* 170: 31-39).

In yet another embodiment, a nucleic acid encoding a HPV fusion polypeptide of the invention is expressed in mammalian cells using a mammalian expression vector. Examples of mammalian expression vectors include, e.g., but are not limited to, pCDM8 (Seed, *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells useful for expression of the HPV fusion polypeptide of the present invention. See, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), in particular promoters of T cell receptors (Winoto and Baltimore, EMBO J. 8: 729-733, 1989) and immunoglobulins (Banerji, et al., 1983. *Cell* 33: 729-740; Queen and Baltimore, *Cell* 33: 741-748, 1983.), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a HPV fusion polypeptide can be expressed in bacterial cells such as *E. coli*, insect cells, yeast or mammalian cells. Mammalian cells are a preferred host for expressing nucleotide segments encoding immunoglobulins or fragments thereof. See Winnacker, *From Genes To Clones*, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. Preferably, the cells are nonhuman. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Preferred expression control sequences are promoters derived from endogenous genes, cytomegalovirus, SV40, adenovirus, bovine papillomavirus, and the like. Co et al., *J Immunol.* 148: 1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation, biolistics or viral-based transfection can be used for other cellular hosts. Other methods used to transform mammalian cells include the use of polybrene, protoplast fusion, liposomes, electroporation, and microinjection (see generally, Sambrook et al., *Molecular Cloning*). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the HPV fusion polypeptide or can be introduced on a separate vector. Cells stably transfected with the introduced nucleic acid can be identified by drug selection (e.g., cells that have incorporated the selectable marker gene will survive, while the other cells die).

A host cell that includes an HPV fusion polypeptide of the present invention, such as a prokaryotic or eukaryotic host cell in culture, can be used to produce (i.e., express) recombinant HPV fusion polypeptides. In one embodiment, the method comprises culturing the host cell of invention (into which a recombinant expression vector encoding the HPV fusion polypeptide has been introduced) in a suitable medium such that the HPV fusion polypeptide is produced. In another embodiment, the method further comprises the step of isolating the HPV fusion polypeptide from the medium or the host cell. Once expressed, the HPV fusion polypeptides are purified from culture media and host cells. The HPV fusion polypeptide can be purified according to standard procedures of the art, including HPLC purification, column chromatography, gel electrophoresis and the like. In one embodiment, the HPV fusion polypeptide is produced in a host organism by the method of Boss et al., U.S. Pat. No. 4,816,397. Purification of recombinant polypeptides is well known in the art and include ammonium sulfate precipitation, affinity chromatography purification technique, column chromatography, ion exchange purification technique, gel electrophoresis and the like (see generally Scopes, *Protein Purification* (Springer-Verlag, N.Y., 1982).

Other sequences, such as an affinity purification tag (e.g. His Tag), a peptide linker sequence, and the like, can also be included in the HPV fusion polypeptide of the present invention. In one embodiment, the HPV fusion polypeptide of the present invention, is fused to a second protein, which can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present invention can also be engineered to improve characteristics of the HPV fusion polypeptide. For instance, a region of additional amino acids, particularly charged amino acids, can be added to the N-terminus of the HPV fusion polypeptide to improve stability and persistence during purification from the host cell or subsequent handling and storage. Also, peptide moieties can be added to the HPV fusion polypeptide to facilitate purification. Such regions can be removed prior to final preparation of the HPV fusion polypeptide. The addition of peptide moieties to facilitate handling of polypeptides are familiar and routine techniques in the art. The HPV fusion polypeptide of the invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc. Chatsworth, Calif.), among others, many of which are commercially available. As described in Gentz et al., *Proc. Natl. Acad. Sci. USA* 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., *Cell* 37: 767, 1984.

Methods for Identifying and/or Screening the HPV Fusion Polypeptides of the Invention.

Methods useful to identify and screen the HPV fusion polypeptides that possess the desired immunogenicity include any immunologically-mediated techniques known within the art. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with HPV fusion polypeptide of the present invention and antigen presenting cells and the synthesis and secretion of cytokines measured by standard methods (Windhagen A; et al, *Immunity*, 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.*, 86: 4230-4, 1989); (4) mast cells can be incubated with reagents that cross-link their Fc-epsilon receptors and histamine release measured by enzyme immunoassay (Siraganian et al., *TIPS*, 4: 432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72: 1310-5, 1988); (3) the proliferation of peripheral blood mononuclear cells in response to mitogens or mixed lymphocyte reaction can be measured using $^3$H-thymidine; (4) the phagocytic capacity of granulocytes, macrophages, and other phagocytes in PBMCs can be measured by placing PMBCs in wells together with labeled particles (Peters et al., *Blood,* 72: 1310-5, 1988); and (5) the differentiation of immune system cells can be measured by labeling PBMCs with antibodies to CD molecules such as CD4 and CD8 and measuring the fraction of the PBMCs expressing these markers.

Uses of the Vaccine Compositions of the Present Invention

In one aspect, the present invention provides methods of using HPV fusion polypeptides as vaccines to treat or prevent HPV-related diseases. The common HPV-related diseases include, but are not limited to genital warts, recurrent respiratory papillomatosis, cervical intraepithelial neoplasia (CIN), cervical cancer, and anal intraepithelial neoplasia (AIN).

In one embodiment, the vaccine compositions of the present invention are used to treat or prevent genital warts. Genital warts spread through sexual contact and are highly contagious. Genital warts may be relieved naturally, but often recur.

In one embodiment, the vaccine compositions of the present invention are used to treat or prevent recurrent respiratory papillomatosis (RRP). RRP is caused by the same HPV as genital warts. According to the findings published in 1995, new RRP cases include 2,000 pediatrics and 3,500 adults cases per year. RRP mainly occurs on vocal cords, but can also spread to tracheas and lungs. The patients mainly die of surgery complications, airway obstruction, cancer transformation or extensive disease spread. Today, the primary treatment is surgery, as no drug for this disease has been approved.

In one embodiment, the vaccine compositions of the present invention are used to treat or prevent cervical intraepithelial neoplasia (CIN) and/or cervical cancer. CIN is characterized by the abnormal proliferation of cervical cells, and generally occurs before cervical cancer. The abnormal cells can be detected by routine Pap smear. It was estimated by the NCI that there were 1,200,000 women diagnosed as having low grade CIN annually. In addition, it was reported that there were 200,000-300,000 women diagnosed as having high grade CIN annually. Currently, the topical surgical treatment does not always work, as it cannot eliminate the abnormal cells completely, nor cure the viral infection. Furthermore, surgeries will result in side effects, such as decreased fertility. CIN, as a precancerous lesion of cervical cancer, is a worldwide public health problem, especially for those countries where the Pap smear is not extensively used. It is estimated that there were 13,000 new cases of invasive cervical cancer in the USA in 2002, and about 4,100 died. There are about 500,000 new cases of cervical cancer worldwide, and about 300,000 patients died of this disease. Cervical cancer is the second most common gynecologic tumor, next only to breast cancer. Although the mortality of cervical cancer has gradually decreased, invasive cervical cancers still have a very high mortality. Now it is believed that HPV is a leading factor of cervical cancer. There are more than 10 HPV types related to cervical cancer, including HPV 16, 18, 31, 35, 58, in which HPV-16 is highly related to cervical cancer and called high-risk type. Research has shown that high-risk HPV infection is a key link in the development of cervical cancer. It is generally accepted that the integration of viral DNA into the genome is a key step in cell canceration, in which the HPV-16 E6 and E7 proteins are two oncoproteins with important transformation properties.

In one embodiment, the vaccine compositions of the present invention are used to treat or prevent anal intraepithelial neoplasia (AIN). AIN is characterized in epithelial dysplasia and occurs before anus canceration. High grade AIN is mainly caused by HPV. It is predicted there are 500,000 new cases per year in the United States.

Dosage and Formulation of Pharmaceutical Compositions

The present invention envisions treating a disease, for example, HPV-related diseases, HPV-induced cancers and the like, in a mammal by the administration of the vaccine compositions of the present invention. Administration of the vaccines in accordance with the present invention may be continuous or intermittent, depending, for example, upon the recipient's physiological condition, whether the purpose of the administration is therapeutic or prophylactic, and other factors known to skilled practitioners. The administration of the vaccines of the invention may be essentially continuous over a preselected period of time or may be in a series of spaced doses. Both local and systemic administration is contemplated.

In one embodiment, the HPV fusion polypeptides are administered directly to a subject to achieve the desired immune response. In another embodiment, immune cells from a subject are contacted with the HPV fusion polypeptides ex vivo and then re-administered to the subject to achieve the desired immune response. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

Typically, an effective amount of the compositions of the present invention, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For administration of HPV fusion polypeptides, the dosage ranges from about 0.0001 to 100 mg/kg, and more usually 0.01 to 5 mg/kg every week, every two weeks or every three weeks, of the subject body weight. For example dosages can be 1 mg/kg body weight or 10 mg/kg body weight every week, every two weeks or every three weeks or within the range of 1-10 mg/kg every week, every two weeks or every three weeks.

The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In one embodiment of the present invention, a preferred dosage regimen for mice is, for each mouse, about 10 μg to about 400 μg of recombinant HPV fusion polypeptide per subcutaneous injection. Typically, one injection will result in a notable immunological protection; while two to three separate subcutaneous injections will result in a prolonged immunological protection. One skilled in the art can determine the range of the clinically effective amount and the immunization times and intervals based upon the subject and desired treatment outcome.

Toxicity. Preferably, an effective amount (e.g., dose) of HPV fusion polypeptides described herein will provide therapeutic benefit without causing substantial toxicity to the subject. Toxicity of the HPV fusion polypeptides described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the HPV fusion polypeptides described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

One or more suitable unit dosage forms having the vaccines of the invention, which, as discussed below, may optionally be formulated for sustained release (for example using microencapsulation, see WO 94/07529, and U.S. Pat. No. 4,962,091), can be administered by a variety of routes including parenteral, including by intravenous and intramuscular routes, as well as by direct injection into the diseased tissue. For example, the vaccine may be directly injected into a tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the vaccine compositions of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes. The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in *Remington's Pharmaceutical Sciences*, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in an mammal body to achieve a particular effect. One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular subject.

The vaccine compositions of the present invention may also comprise nucleic acids encoding the HPV fusion polypeptides. Pharmaceutical formulations, dosages and routes of administration for nucleic acids are generally disclosed, for example, in Felgner et al., 1987, *PNAS* 84; 7413-7417. In one embodiment nucleic acids are administered directly to a patient, e.g., to the site of the tumor or using a combination of one or more targeting agents to target the nucleic acid to an immune cell. In another embodiment, nucleic acids are contacted with immune cells isolated from the subject, and the transfected cells are introduced into the patient. The nucleic acid molecule encoding the fusion protein of the present invention may be operatively linked to essential genetic regulatory elements, such as a promoter, an enhancer, a selection marker, and the like.

Formulations of Pharmaceutical Compositions. According to the methods of the present invention, the HPV fusion polypeptides can be incorporated into pharmaceutical compositions suitable for administration. The pharmaceutical compositions generally comprise recombinant or substantially purified HPV fusion polypeptides and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (see, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the HPV fusion polypeptides are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the HPV fusion polypeptide, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. The HPV fusion polypeptides named in this invention can be present in unsalified or unesterified form, or in salified and/or esterified form, and the naming of such HPV fusion polypeptide is intended to include both the original (unsalified and unesterified) compound and its pharmaceutically-acceptable salts and esters. Also, certain HPV fusion polypeptides named in this invention can be present in more than one stereoisomeric form, and the naming of such HPV fusion polypeptides is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present invention.

Preferred examples of such carriers or diluents include, but are not limited to, water, saline, Ringer's solutions, dextrose solution, and 5% human serum albumin. Liposomes and nonaqueous vehicles such as fixed oils may also be used. The use of such media and compounds for pharmaceutically active substances is well known in the art. Except insofar as any conventional media or compound is incompatible with the HPV fusion polypeptides, use thereof in the compositions is contemplated. Supplementary active compounds can also be incorporated into the compositions.

A pharmaceutical composition of the invention is formulated to be compatible with its intended route of administration. The HPV fusion polypeptides compositions of the present invention can be administered by parenteral, topical, intravenous, oral, subcutaneous, intraarterial, intradermal, transdermal, rectal, intracranial, intraperitoneal, intranasal; intramuscular route or as inhalants. The HPV fusion polypeptides can optionally be administered in combination with other agents that are at least partly effective in treating various diseases including various actin- or microfilament-related diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the HPV fusion polypeptides in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the HPV fusion polypeptides are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the HPV fusion polypeptides is formulated into ointments, salves, gels, or creams as generally known in the art.

The HPV fusion polypeptides can also be prepared as pharmaceutical compositions in the form of suppositories (e.g., with conventional suppository bases such as cocoa butter and other glycerides) or retention enemas for rectal delivery.

In one embodiment, the HPV fusion polypeptide is prepared with carriers that will protect the HPV fusion polypeptide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

Adjuvants. In some embodiments, the HPV fusion polypeptide of the present invention is administered with a adjuvant. The present inventors have discovered that certain adjuvants act synergistically with the HPV fusion polypeptides to promote immune responses for the treatment of HPV-related diseases. Immunization protocols often use adjuvants to stimulate immune responses. Some adjuvants affect the way in which antigens are presented. For example, the immune response is increased when protein antigens are precipitated by alum. Emulsification of antigens also prolongs the duration of antigen presentation. Other adjuvants, for example, certain organic molecules obtained from bacteria, act on the subject rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

In order to reinforce the immunological effect of the HPV fusion polypeptides of the present invention, the pharmaceutical composition can comprise an immunologic adjuvant, such as complete/incomplete Freund's adjuvant, alum, calcium phosphate, oligodeoxyribonucleotide, as well as cytokines, e.g. IL-2, 4, 12, 15, interferon α, γ, granulocyte-macrophage colony stimulating factor and the like. In one embodiment, the adjuvant is Bacille Calmette-Guérin (BCG). BCG is a vaccine against tuberculosis that is prepared from a strain of the attenuated (weakened) live bovine tuberculosis *bacillus, Mycobacterium bovis*, that has lost its virulence in humans.

All publications, patent applications, issued patents, and other documents referred to in the present disclosure are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

EXAMPLES

The present invention is further illustrated by the following examples, which should not be construed as limiting in any way.

Example 1

Preparation of HPV Vaccine Polypeptides of the Present Invention

Recombinant HPV vaccine polypeptides were produced in *E. coli* according to the procedures described in this Example. Using the methods described below, it would also be possible for the skilled artisan to generate and/or compare additional HPV vaccine polypeptides to the ones shown in these examples.

1. Synthesis of HPV E7 Mutants.

The codon-optimized E7 gene, the E7m2 mutant (The double mutation C59S and C68V) and the E7m3 mutant (the triple mutation C24V, C59S and C68V) were synthesized and ligated into a transfer vector by restrictive enzymes Sal I and Not I. The residue numbers for the mutations represent the residue number within E7 sequence (SEQ ID NO: 1). The gene codons were optimized with the aid of the program Gene Designer (DNA 2.0). The rare codons were substituted by the codons which are often used in the host cells. The codons were further optimized to reduce the secondary structures that could form in the mRNA. The secondary structures in the mRNA may interfere with the protein translations.

2. Generating Expression Vectors pET28b-E7, pET28b-E7m2, pET28b-E7m3

After Sal I and Not I enzyme digestion as described above, the synthesized E7, E7m2 and E7m3 fragments were ligated to the prokaryotic expression vector pET28b. Detailed procedures were as follows. First, the expression plasmid pET28b was digested with restriction enzymes Sal I and Not I. The reaction comprised: pET28b plasmid (3 μg), 10× restriction enzyme buffer (5 μl), each Sal I and Not I enzyme (10 U each), 0.1% Triton X-100 (5 μl), 0.1% BSA (5 μl), and purified water to a total volume of 50 μl. The reaction was incubated at 37° C. for 4 to 8 h and the digested plasmid was separated by gel electrophoresis. The DNA fragment was purified from the gel and stored at −20° C. Next, the individual E7, E7m2, or E7m3 fragments were ligated into the expression vector pET28b. For the ligation reaction, the following components were added to a 0.5 ml Eppendorff tube: 10× T4 DNA ligase buffer (1.5 μl), the digested E7, E7m2, or E7m3 gene fragment obtained above (0.2 pmoles), the digested pET28b obtained above (0.02 pmoles), T4 DNA ligase (280 U) and purified water, in a total volume of 15 μl. The reaction was incubated at 10-16° C. overnight. The ligated products were used to transform *E. coli* DH5α (Tiangen Biotech, Beijing, China), according to the manufacturer's instructions. Cells were plated on media containing kanamycin. Individual colonies were selected, and plasmids were recovered with a plasmid DNA extraction kit (Tiangen Biotech, Beijing China). Sequencing was used to confirm the identity of the clones.

3. Generating C6 or C7 Fragments

DNA fragments encoding N-terminal domains of human CRT were obtained using PCR. Primers P1 and P2 for C6 amplification and primers P3 and P4 for C7 amplification were designed according to the full-length cDNA sequence of human CRT gene (GenBank Accession Nos: BC002500/BCO20493/BC007911). A Nde I restriction site was introduced into primers P1 and P3. A Sal I restriction site was introduced into primers P2 and P4. The primers were synthesized by Shanghai Yingjun Biotechnology Co., Ltd. The primer sequences are shown in Table 17.

TABLE 17

Primer Sequences for Amplifying CRT Fragments.

| Primer Name | Sequence (5' to 3') | SEQ ID NO: |
|---|---|---|
| P1 | GGAATTCCATATGGAGCCTGCCGTCTACTTCAAGGAGCAGTTTC | SEQ ID NO: 18 |
| P2 | CGCGTCGACCCTCTGCTCCTCGTCCTGTTTGTCCTTCATTTG | SEQ ID NO: 19 |
| P3 | GGAATTCCATATGGAGCCTGCCGTCTACTTCAAGGAGCAGTTTC | SEQ ID NO: 20 |
| P4 | CGCGTCGACCAGCTCGTCCTTGGCCTGGCCGGGGACATCTTC | SEQ ID NO: 21 |

PCR amplification was according to standard procedures using a plasmid carrying CRT full-length coding gene as a template. P1 and P2 were used as primers to amplify C6. P3 and P4 were used as primers to amplify C7. The PCR products were functionalized by gel electrophoresis. The DNA fragments were purified from the gel and stored at −20° C.

4. Generating Expression Vectors pET28b-C6E7, pET28b-C6E7m2, pET28b-C6E7m3, pET28b-C7E7, pET28b-C7E7m2, or pET28b-C7E7m3.

After both Sal I and Nde I enzyme digestion, the C6 or C7 fragments were ligated into prokaryotic expression vector pET28b-E7, pET28b-E7m2, or pET27E7m3. The detailed procedures were as follows. First, the expression plasmid pET28b was digested with restriction enzymes Sal I and Not I. The reaction comprised: pET28b-E7, pET28b-E7m2, or pET27E7m3 plasmid (3 μg), 10× restriction enzyme buffer (5 μl), each Sal I and Nde I enzyme (10 U each), 0.1% BSA (5 μl), and purified water to a total volume of 50 μl. The reaction was incubated at 37° C. for 4 to 8 h and the digested plasmid was separated by gel electrophoresis. The DNA fragment was purified from the gel and stored at −20° C. Next, the individual C6 or C7 fragments were ligated into the expression vector pET28b-E7, pET28b-E7m2, or pET27E7m3. For the ligation reaction, the following components were added to a 0.5 ml Eppendorff tube: 10× T4 DNA ligase buffer (1.5 μl), the digested C6 or C7 gene fragments obtained above (0.2 pmoles), the digested pET28b-E7, pET28b-E7m2, or pET27E7m3 obtained above (0.02 pmoles), T4 DNA ligase (280 U) and purified water in a total volume of 15 µl. The reaction was incubated at 10-16° C. overnight. The ligated products were used to transform *E. coli* DH5α (Tiangen Biotech, Beijing, China), according to the manufacturer's instructions. Cells were plated on media containing kanamycin. Individual colonies were selected, and plasmids were recovered with a plasmid DNA extraction kit (Tiangen Biotech, Beijing China). Sequencing was used to confirm the identity of the clones.

5. Expression of HPV Vaccine Polypeptides

The constructed expression vectors pET28b-C6E7, pET28b-C7E7, pET28b-C6E7m2, pET28b-C6E7m3, pET28b-C7E7m2, and pET28b-C7E7m3 were used to transform *Escherichia coli* BL21 (DE3). The transformed cells were cultured in 2×YT medium (20 g peptone, 10 g yeast power, 10 g sodium chloride per L) at 30° C., to which kanamycin was added to 50 µg/ml. After the OD600 of the culture reached 0.4-1.0, IPTG was added to a final concentration of 1.0 mM to induce the expression of the HPV vaccine polypeptides. Following induction at 37° C. for 3 h, cells were collected by centrifugation. The cells were diluted in 20 volumes of 20 mM Tris, 2 mM EDTA, pH 8.0, and, after a thorough mix, disrupted by sonication. Insoluble precipitates were removed by centrifugation at 13,000×g for 30 min. The proteins of interest were present in the supernatant, with the expressed product comprising approximately 20% of soluble proteins (data not shown). These results demonstrate that the HPV fusion polypeptides of the present invention exhibit the advantageous property of being expressed in soluble form in *E. coli* cells.

6. Purification of HPV Fusion Polypeptides

The proteins in the supernatant were precipitated with PEI (polyethyleneimine, Sigma-Aldrich, St. Louis, Mo.). Briefly, 10% PEI and the supernatant obtained by centrifugation were added together in a proportion of 0.08:1. The mixture was allowed to stand at 4° C. for 15 min, followed by centrifugation at 12,000 rcf for 30 min. The precipitate was then washed with buffer A (50 mM Tris, 0.5 mM EDTA, 50 mM NaCl, 5% glycerin, pH 7.9) containing 0.3 M NaCl, and the supernatant was discarded. The proteins of interest were eluted with 20 volumes of buffer A containing 0.9 M NaCl. The supernatant was collected by centrifugation and the precipitate was discarded. Next, the supernatant was precipitated with 55% $(NH_4)_2SO_4$ (7.5 g $(NH_4)_2SO_4$ per 20 ml liquid) overnight. The precipitate was collected by centrifugation.

The product sample obtained by $(NH_4)_2SO_4$ precipitation was purified by QFF (Q sepharose fast flow, GE Healthcare Biosciences, Piscataway, N.J.). Briefly, the precipitates were resolubilized with 20 volumes of 20 mM PB, pH 7.0 and applied to a Q Sepharose Fast Flow column (XK-35, 3.5×10 cm, GE Healthcare Biosciences, Piscataway, N.J.). The linear flow rate was 100 cm/h. The contaminant proteins were eluted with 0.3 M NaCl, and the proteins of interest were eluted with 0.6 M NaCl. The eluted proteins of interest were desalted with Sephadex G-25 (Sigma-Aldrich, St. Louis, Mo.), and the buffer was replaced with 20 mM PB, 4 M urea, pH 6.0. After the buffer replacement was completed, the protein sample was purified with SP chromatography (SP Sepharose fast flow, GE Healthcare Biosciences, Piscataway, N.J.) in the same buffer. All of the proteins of interest were present in the flow-through.

Sephacryl S-200 was used to further purify the sample. The loading volume was 3% of the column volume, linear rate of flow was 70 cm/hour, and the buffer was 20 mM PB, 0.2 M NaCl, pH 7.0. The eluting peak was collected. Finally, the residual endotoxin was removed by detoxigen resin (Cat. No. CS-L01, Beijing Zuoguan Co., Ltd., Beijing, China). After SDS-PAGE and subsequent Coomassie brilliant blue staining, the purity of the proteins of interest was typically >95% and endotoxin content was <2 EU/ml (see FIGS. 1A, 1B, 1C). The protein samples were stored at −80° C. and were used within one month in the functional assays described below in Examples 3-6.

Example 2

Enhanced Stability of HPV Fusion Polypeptides of the Present Invention

Studies were performed to assess the stability of the HPV fusion polypeptides as described below. These studies also assessed whether the HPV fusion polypeptides formed aggregates based upon disulfide bond formation. In particular, comparison was made between HPV vaccine polypeptides comprising the wild-type E7 sequence with those comprising the E7m2 or E7m3 mutant sequences.

Samples were prepared as described in Example 1, divided into aliquots, and stored at 4° C., −20° C., and −80° C. SDS-PAGE analysis was used to assess the stability of the fusion polypeptides of the invention following storage for varying periods of time. The samples (10 µg of total protein) were fractionated by 10% SDS-PAGE using standard techniques. In some experiments, fractionation was conducted under reducing conditions by the addition of 2 mM DTT to the gel. Gels were stained with Coomassie brilliant blue and quantified using densitometry by Tanon GIS (Gel Image System, Tanon Co, Shanghai, China).

To verify the stability and purity of the proteins after the expression and extraction from *E. coli*, freshly-prepared samples of C6E7, C6E7m2 and C6E7m3 were analyzed by SDS-PAGE (FIGS. 1A, 1B, and 1C, respectively). The gels were scanned and densitometry was used to quantify the relative amount of HPV fusion proteins. Specifically, results are expressed as a percentage of the number of pixels in band corresponding C6E7, C6E7m2, and C6E7m3 over the total number of pixels in the lane. For each HPV vaccine polypeptide, running the samples under reducing conditions yielded larger quantities of proteins of the expected molecular weight compared to the samples run under non-reducing conditions (Table 14), suggesting that disulfide bonds formed between the polypeptides in each preparation. However, the amount of C6E7m2 detected under non-reducing conditions was significantly greater than wild-type C6E7 (88.18% versus 66.43%).

To ascertain the stability of HPV fusion polypeptides upon storage, samples were placed at 4° C. for two months and then reanalyzed by SDS-PAGE (FIG. 1D and Table 14). The purity of C6E7m2 was significantly higher than that of C6E7 and C6E7m3, as evidenced by SDS-PAGE analysis. The wild-type C6E7 exhibited a large amount of degradation upon storage. All of the C6E7 degraded during storage as shown in both non-reducing and reducing SDS-PAGE (FIG. 1D). Some of the C6E7m3 was degraded, but not to the same extent as the wild-type. Almost all of the C6E7m2 remained intact during storage. Comparing the sample run under non-reducing and reducing conditions, it was observed that most of the C6E7m2 is aggregated (evidenced by the high molecular weight band on SDS-PAGE). This is possibly caused by cysteine crosslinking during storage, but the disulfide bonds are disrupted when applied to the SDS-PAGE gel under reducing conditions.

TABLE 18

Quantification of Protein Bands by Densitometry (Storage at 4° C.)

| Samples | Amount of Fusion Protein (Percent of Total Protein) | | |
|---|---|---|---|
| | C6E7 | C6E7M2 | C6E7M3 |
| Fresh sample purity | 66.43% Non-reducing | 88.18% Non-reducing | 62.2% Non-reducing |
| | 91.22% Reducing | 93.48% Reducing | 96% Reducing |
| After storage at 4° C. for two months | 4.86 Non-reducing | 12.92% Non-reducing | 13.71% Non-reducing |
| | 5.05% Reducing | 79.45% Reducing | 58.7% Reducing |

To further ascertain the stability of the HPV fusion proteins upon storage, samples were placed at −80° C. for 1.5 months and then analyzed by SDS-PAGE (FIG. 1E and Table 15). The purity of C6E7m2 is much higher than that of C6E7 and C6E7m3, as evidenced by SDS-PAGE analysis (FIG. 1E). The amount of intact C6E7 and C6E7m3 decreased significantly upon storage as shown in non-reducing gel (FIG. 1E, lanes 1 and 3). Moreover, a significant amount of aggregation of C6E7m3 is indicated by the high-molecular weight band in the SDS-PAGE gel (FIG. 1E, lane 3). C6E7m2 showed good stability and the aggregation of C6E7m2 is less severe than C6E7 and C6E7m3 (FIG. 1E, lane 2).

TABLE 19

Quantification of Protein Bands by Densitometry (Storage at 4° C.)

| Samples | Amount of Fusion Protein (Percent of Total Protein) | | |
|---|---|---|---|
| | C6E7 | C6E7M2 | C6E7M3 |
| Fresh sample purity | 65.53% Non-reducing | 80.98% Non-reducing | 62.2% Non-reducing |
| | 90.88% Reducing | 86.19% reducing | 96% Reducing |
| After storage at −80° C. for 1.5 month | 32.66% Non-reducing | 84.18% Non-reducing | 25.45% Non-reducing |
| | 90.39% Reducing | 91.92% Reducing | 82.89% Reducing |

Figure 2B:
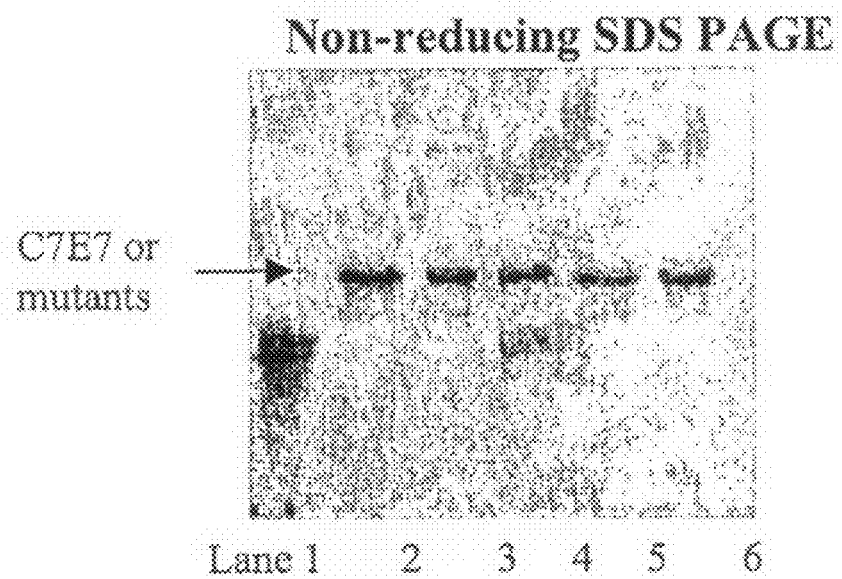

The stability of the C7E7, C7E7m2, and C7E7m3 vaccine polypeptides of the present invention was also characterized following storage at either 4° C. or −20° C. for 7 days. The results are shown in FIG. 2. After storage at 4° C. for 7 days, wild-type C7E7 was almost totally degraded (FIGS. 2A and 2B, lane 1), as evidenced by SDS-PAGE under either reducing or non-reducing conditions. By contrast, mutants C7E7m2 and C7E7m3 were largely intact following storage (FIGS. 2A and 2B, lanes 2-3, respectively). Likewise, after storage at −20° C. for 7 days, wild-type C7E7 exhibited significant degradation (FIGS. 2A and 2B, lane 4) compared to mutants C7E7m2 and C7E7m3 (FIGS. 2A and 2B, lanes 5-6, respectively). The resistance of the C7E7m2 and C7E7m3 mutants to degradation and aggregation compared to the wild type indicates that the vaccines comprising these polypeptides have utility for the production of a HPV vaccine that remains stable from the time of production until it is administered to patients. Accordingly, the HPV fusion polypeptides of the invention provide vaccine composition, which have the advantage of enhanced stability during storage compared to polypeptides comprising the wild-type E7 antigen.

Example 3

Prophylactic Effect of HPV Fusion Polypeptides of the Present Invention on Tumor Incidence In Vivo The ability of the HPV fusion polypeptides of the present invention to provide a prophylactic benefit against tumors induced by HPVs was tested using a mouse model of the human cancer. In particular, mice were challenged with HPV 16 E6/E7-transformed mouse TC-1 cells after administration of the HPV fusion polypeptides of the present invention.

The TC-1 lung metastasis model can be used to test the efficacy of various E6/E7-specific vaccines and immunotherapeutic strategies See Lin K Y, et al. Cancer Res. 56: 21-26, 1996. Tumor cell line TC-1 cell line (ATCC Accession No: CRL-2785) was obtained from primary lung epithelial cells of C57BL/6 mice. The cells were transformed with HPV-16 (Human papilloma virus) E6, E7 and human c-Ha-ras oncogenes and were found to be positive for the expression of HPV-16 E7. In all of the experiments described herein, TC-1 cells were cultured in RPMI 1640 (Gibco BRL, Gaithersburg, Md.)+10% FBS (Hyclone, Logan, Utah) medium at 37° C. in a incubator with 5% $CO_2$.

For all of the studies in this Example, C57BL/6 mice (10 per group) were immunized in the scruff of the neck with 200 μg of various immunogens (prepared as described in Example 1), and then boosted 14 d later with the same dose and regimen as the first vaccination. The control group received vehicle alone (PBS) on the same schedule. Ten days after the boost, mice were challenged in the right flank with $1.3 \times 10^5$ TC-1 cells s.c. (day 0) and observed for 50 d. Tumor growth was observed every 3-4 d. Data are presented as percent tumor incidence per group.

Figure 3A:
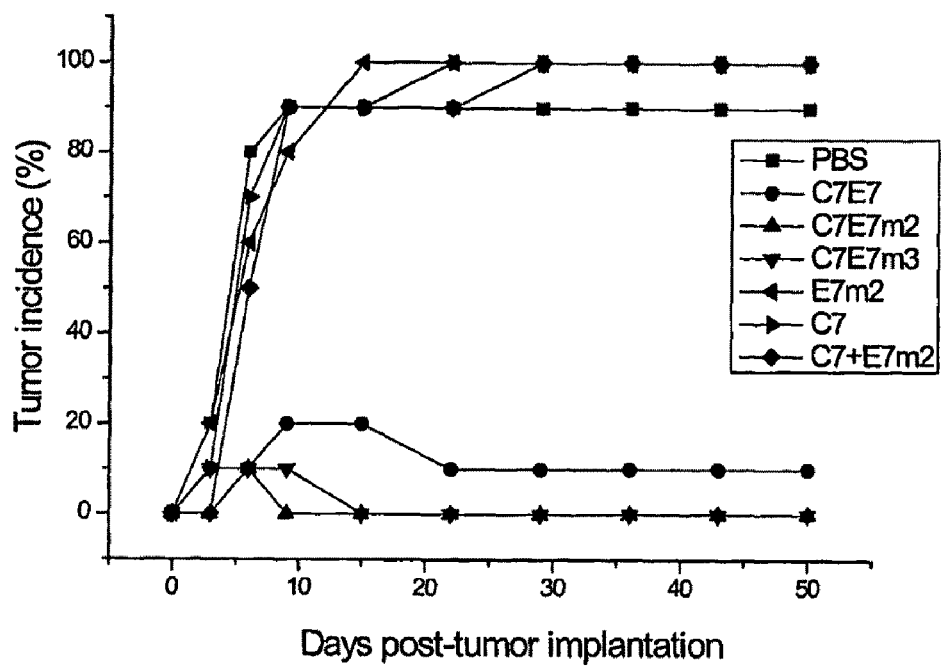
FIG. 3A compares fusion proteins comprising a full-length calreticulin immunostimulatory polypeptide.

In one study, the tumor incidence in mice vaccinated with full-length calreticulin fused to wild-type or mutant HPV16 E7 antigens was investigated. FIG. 3A shows the tumor incidence in mice administered 200 μg HPV fusion polypeptides C7E7, C7E7m2, C7E7m3, as well as the C7 and E7 polypeptides separately or in an admixture. The data indicate that the HPV fusion proteins C7E7, C7E7m2 and C7E7m3 can protect the mice from the TC-1 cell challenges. The mutant proteins C7E7m2 and C7E7m3 showed a slightly better protective effect than the wild type C7E7. The individual C7 or E7 proteins or the admixture of E7 and C7 showed no protective effect.

Figure 3B:
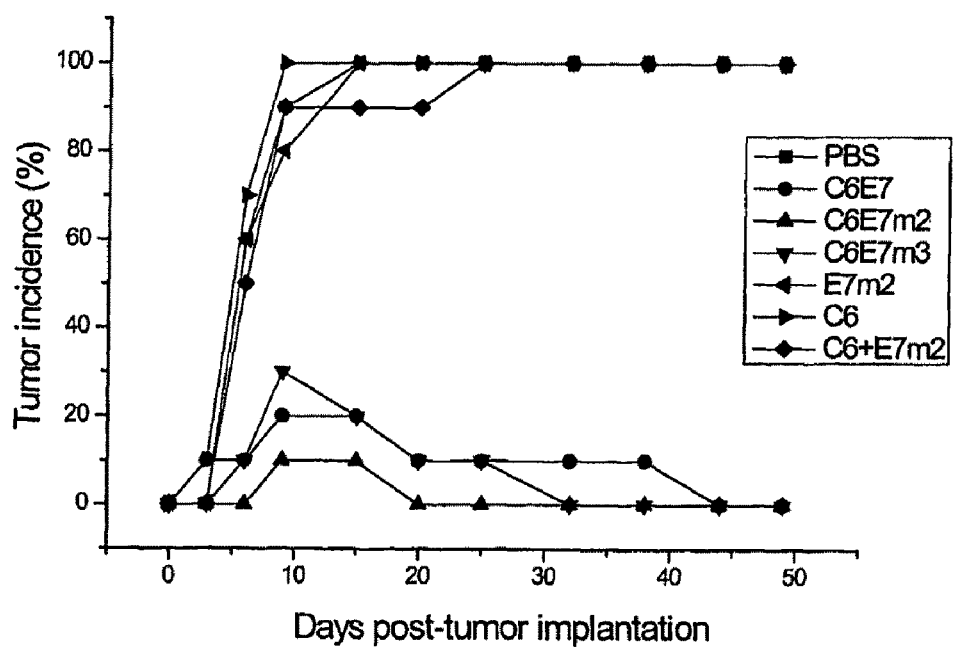
FIG. 3B compares fusion proteins comprising a N-terminal calreticulin fragment (amino acids 18-366 of SEQ ID NO: 2) as an immunostimulatory polypeptide.

In a second study, the tumor incidence in mice vaccinated with the N-terminal domain of calreticulin C6 fused to wild-type or mutant HPV16 E7 antigens was investigated. FIG. 3B shows the tumor incidence in mice administered 200 μg HPV fusion polypeptides C6E7, C6E7m2, C6E7m3, as well as the C6 and E7 polypeptides provided separately or in an admixture. The results are similar to those shown in FIG. 3A and reveal that the N-terminal domain of calreticulin (C6) can substitute well for the full-length calreticulin in providing a protective effect.

The results of these studies indicate that the C6E7m2, C6E7m3, C7E7m2, and C7E7m3 fusion proteins of the present invention are able to provide a protective effect against the formation of HPV-induced tumors. The protective effects for the mutant E7 proteins were shown to be slightly better than the protective effect seen with the wild-type C6E7 or C7E7 polypeptides. Because the TC-1 cells in the mouse model express the same tumor antigen that would be expressed in human HPV-induced tumors, the results of this study are predictive of similar prophylactic effects in humans. As such, the vaccine compositions comprising the HPV fusion polypeptides of the invention are useful in methods for preventing an HPV-related disease, such as cervical cancer, in which cells express an HPV antigen.

Example 4

Therapeutic Effect of HPV Fusion Polypeptides of the Present Invention on Tumor Incidence In Vivo The ability of the HPV fusion polypeptides of the present invention to provide a therapeutic benefit against tumors induced by HPVs was tested using a mouse model of the human cancer. In particular, mice were challenged with HPV16 E6/E7-transformed mouse TC-1 cells before administration of the HPV fusion polypeptides of the present invention.

For the studies in this Example, C57BL/6 mice (10 per group) were injected with $1.5 \times 10^5$ TC-1 cells s.c in the right flank (day 0). At 5 and 19 days post-implantation, the mice were immunized in the scruff of the neck with various immunogens (prepared as described in Example 1). The control group received vehicle alone (PBS) on the same schedule. The presence of tumors was monitored in the mice for 70 days in the groups receiving C7E7, C7E7m2, C7E7m3, C6E7, C6E7m2, C6E7m3, and for 40 days in the other groups. Data are presented as percent tumor incidence per group.

Figure 4A:
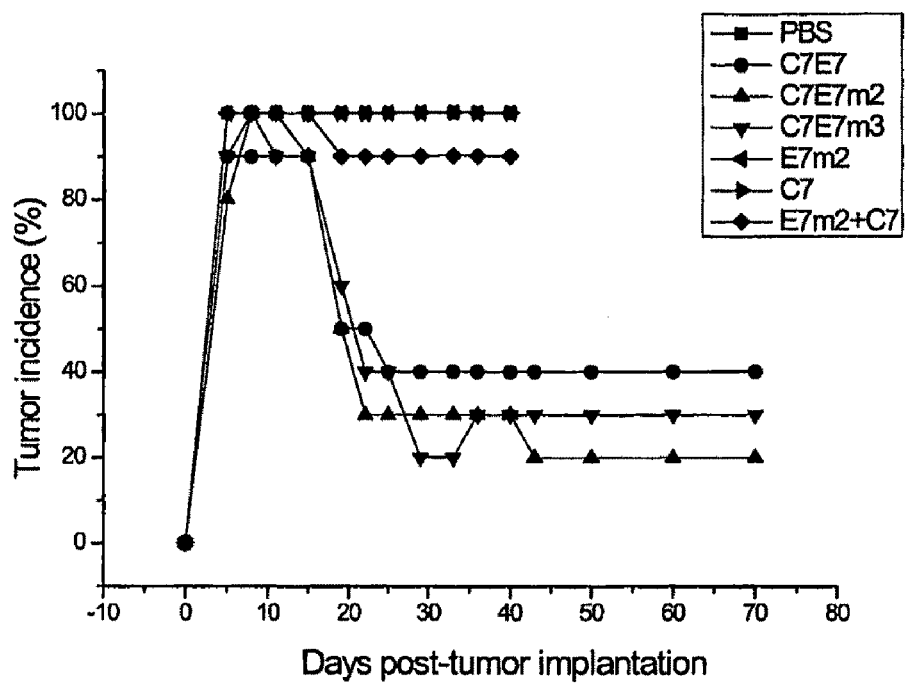
FIG. 4A compares fusion proteins comprising a full-length calreticulin immunostimulatory polypeptide.

In one study, the tumor incidence in mice administered the full-length calreticulin fused to wild-type or mutant HPV E7 antigens was investigated. FIG. 4A shows the tumor incidence in mice immunized with 300 µg C7E7, C7E7m2, C7E7m3 or equalmolar C7, E7m2, and C7+E7m2. The data clearly show that the fusion proteins elicit strong anti-cancer activity in mice. The fusion protein of C7 and E7 mutants C7E7m2, C7E7m3 have better anti-cancer activity than the wild type.

Figure 4B:
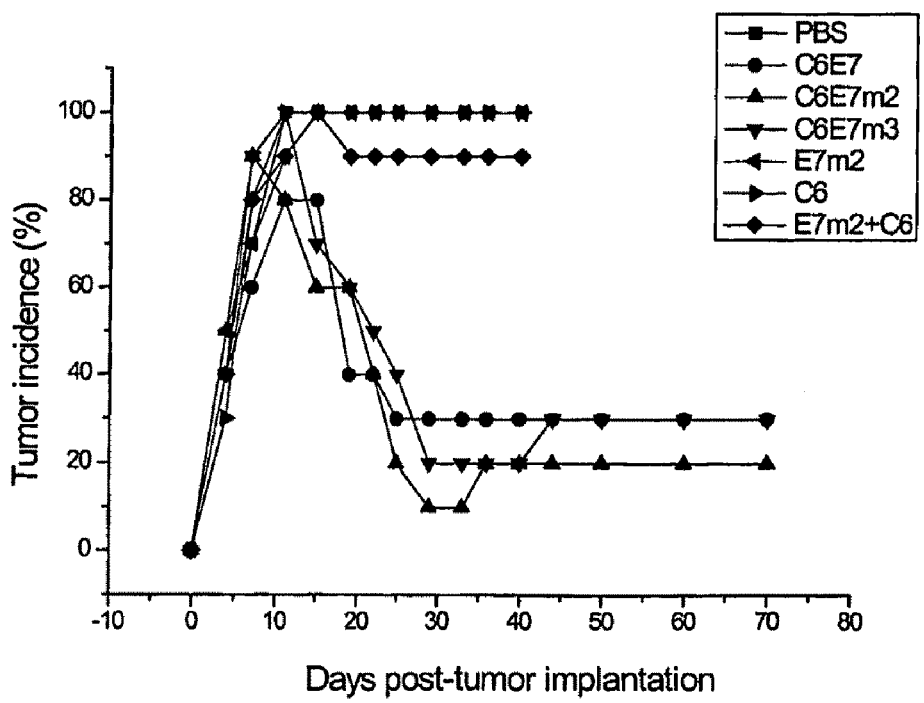
FIG. 4B compares fusion proteins comprising a N-terminal calreticulin fragment as an immunostimulatory polypeptide.

In a second study, the tumor incidence in mice administered the N-terminal domain (amino acids 18-366 of SEQ ID NO:2) of calreticulin fused to wild-type or mutant HPV E7 antigens was investigated. FIG. 4B shows the tumor incidence in mice immunized with 300 µg C6E7, C6E7m2, C6E7m3 or equalmolar C6, E7m2, and C6+E7m2. The results are similar to those shown in FIG. 4A and reveal that the N-terminal domain of calreticulin (C6) can substitute well for the full-length calreticulin in eliciting an anti-cancer response.

Figure 4C:
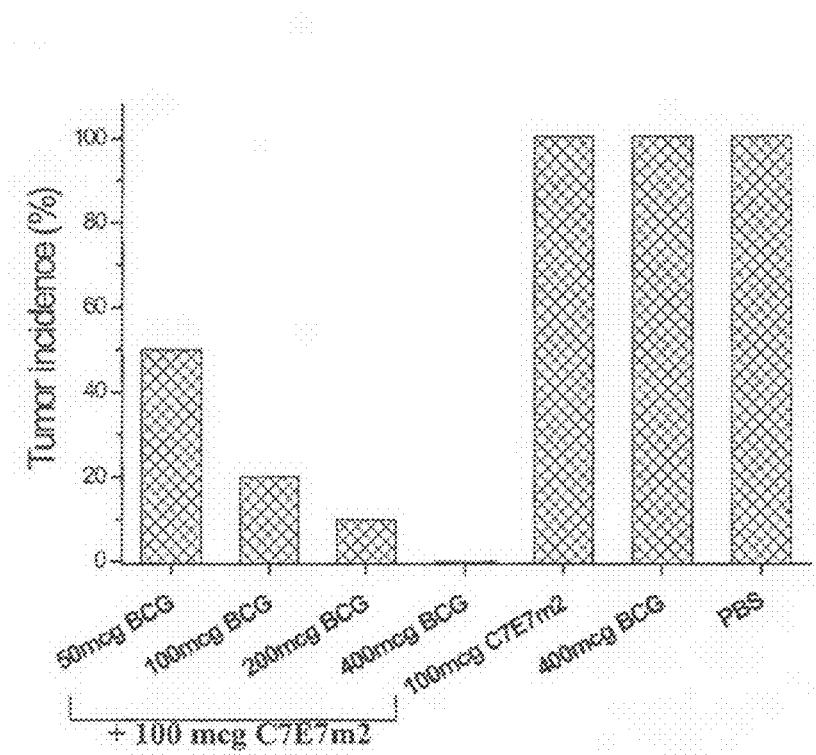
FIG. 4C compares fusion proteins comprising a full-length calreticulin immunostimulatory polypeptide administered in combination with BCG.

In a third study, the tumor incidence in mice administered the full-length calreticulin fused to wild-type or mutant HPV E7 antigens in combination with BCG was investigated. FIG. 4C shows the tumor incidence in mice immunized with 100 µg C7E7m2 or C7E7m2 in combination with BCG (50 µg, 100 µg, 200 µg or 400 µg) or 400 µg BCG. The results indicate that BCG enhances the antitumor activity of C7E7m2.

Figure 4D:
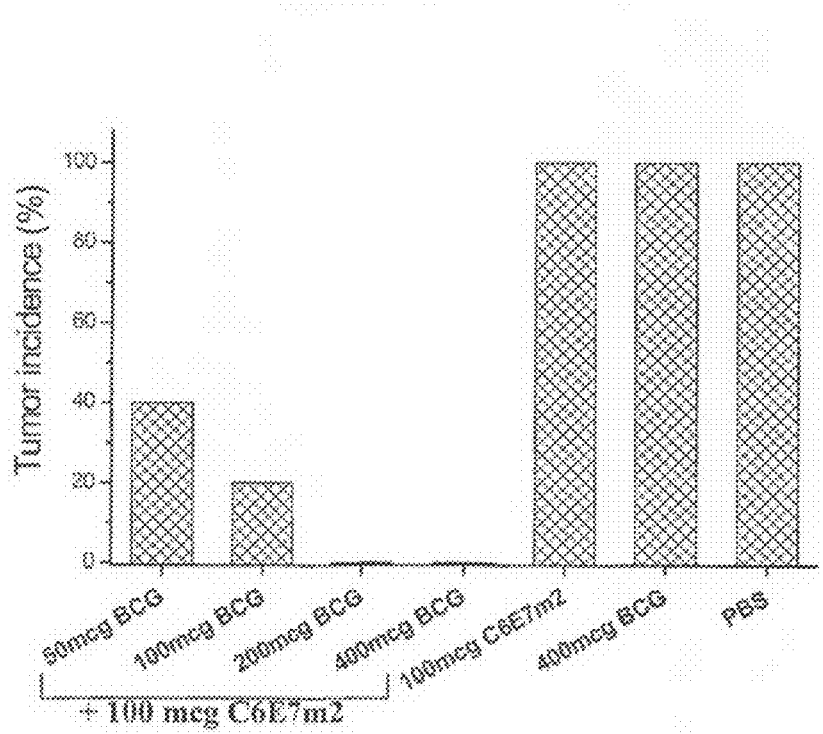
FIG. 4D compares fusion proteins comprising a N-terminal calreticulin fragment as an immunostimulatory polypeptide administered in combination with BCG.

In a fourth study, the tumor incidence in mice administered the N-terminal domain (amino acids 18-366) of calreticulin fused to wild-type or mutant HPV E7 antigens in combination with BCG was investigated. FIG. 4D shows the tumor incidence in mice immunized with 100 µg C6E7m2 or C6E7m2 in combination with BCG (50 µg, 100 µg, 200 µg or 400 µg) or 400 µg BCG. The results indicate that BCG enhances the antitumor activity of C6E7m2. In particular, the synergistic effect observed with the combination of the HPV fusion polypeptide and BCG suggests that BCG may be an effective adjuvant for use in human clinical trials.

In addition to decreasing the tumor incidence in mice administered the 111$^3$V vaccine compositions of the present invention, the size of tumors was also decreased. Mice (n=10 per group) were implanted with $1.5 \times 10^5$ E7-expressing TC-1 tumor cells s.c. in the right flank on day 0. On day 5, mice were injected with either PBS, 200 µg BCG or C6E7m2 alone, 60 µg E7 or E7m2 alone, or BCG admixed with E7, E7m2, or C6E7m2. Tumor growth was observed every 3-4 days, and the length and width of the tumor was measured with a vernier caliper. Tumor volume was calculated by the formula: length×width$^2$÷2, and the changes of tumor growth were plotted.

Figure 5:
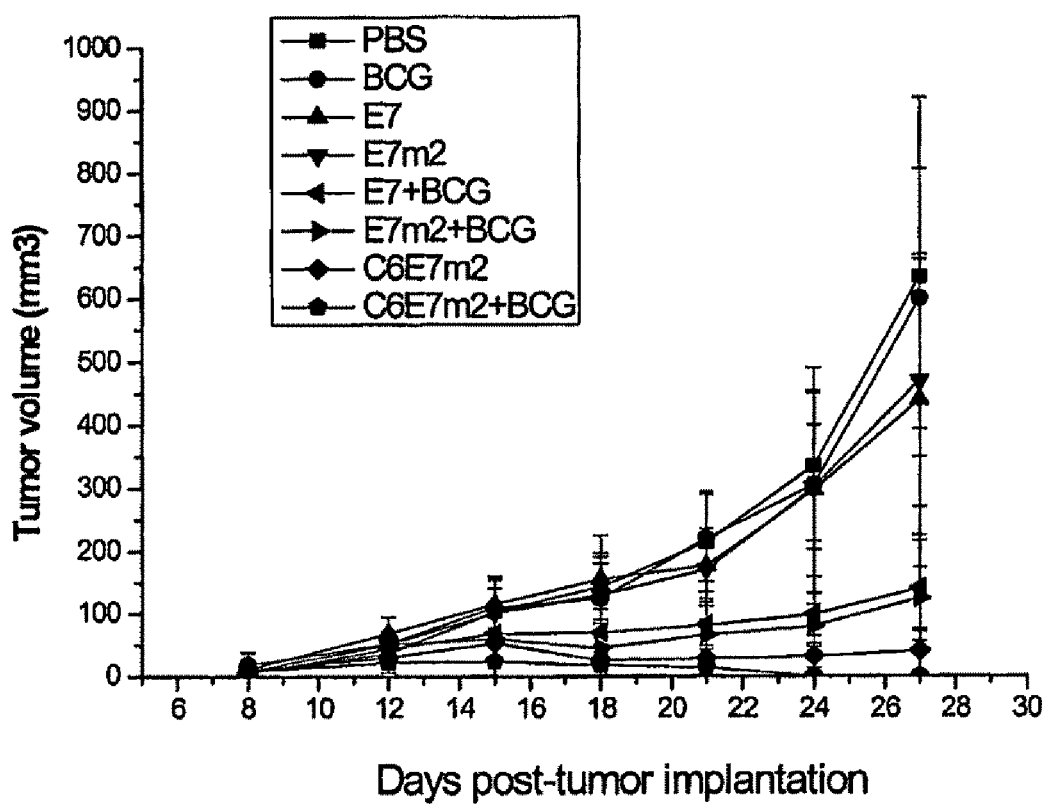
FIG. 5 is a graph of tumor volume in mice administered recombinant HPV fusion polypeptides of the present invention in combination with BCG after challenge with TC-1 tumor cells. The fusion proteins comprise a N-terminal calreticulin fragment as an immunostimulatory polypeptide.

FIG. 5 shows the therapeutic effect of HPV fusion polypeptides of the present invention on tumor size. In this experiment 200 µg BCG could synergistically inhibit TC-1 tumor growth with C6E7m2, E7 and E7m2. However, BCG, E7, or E7m2 alone elicited little or no inhibitory effect on TC-1 tumor growth. The largest inhibitory effects were seen with C6E7m2 either alone or in combination with BCG. The results indicate that the HPV vaccine compositions of the present invention inhibit growth of TC-1 tumors in challenged C57BL/6 mice to a greater extent than vaccine compositions comprising the wild type E7 antigen.

The results of these studies indicate that the C6E7m2, C6E7m3, C7E7m2, and C7E7m3 fusion proteins of the present invention are able to provide a therapeutic effect in treating HPV-induced tumors. The therapeutic effects for the mutant E7 proteins were shown to be slightly better than the protective effect seen with the wild-type C6E7 or C7E7 polypeptides. Furthermore, combined administration with BCG enhances the therapeutic effect of the vaccine compositions of the present invention. Because the TC-1 cells in the mouse model express the same tumor antigen that would be expressed in human HPV-induced tumors, the results of this study are predictive of similar therapeutic effects in humans. As such, the vaccine compositions comprising the HPV fusion polypeptides of the invention are useful in methods for treating an HPV-related disease, such as cervical cancer, in which cells express an HPV antigen.

Example 5

Effect of HPV Fusion Polypeptides of the Present Invention on Inducing a Cytotoxic T-Lymphocyte (CTL) Response The ability of the HPV fusion polypeptides of the present invention to induce a cytotoxic T-lymphocyte response against cells expressing HPV antigen was investigated using an in vitro cytotoxicity assay. For these studies, C57BL/6 mice were injected subcutaneously in the scruff of the neck with various immunogens (prepared as described in Example 1) or PBS. Mice were boosted 7 days later with the same dose and regimen as the first vaccination. Seven days after the boost, spleens were aseptically removed and single cell suspensions were prepared. Erythrocytes were lysed in Tris-buffered ammonium chloride. Pooled splenocytes were restimulated for 5 days with mitomycin C-treated TC-1 cells (20 μg/ml mitomycin C, incubated at 37° C. for 1 h). The splenocytes were tested for cytolytic activity against the following target cells: Lewis (irrelevant target) or the E7-expressing TC-1.

The cytolytic activity of T cells was determined by quantitative measurements of lactate dehydrogenase (LDH) using CytoTox 96 nonradioactive cytotoxicity assay kits (Promega Corp, Madison, Wis., USA) according to manufacturer's protocol. Briefly, effector cells and target cells ($5 \times 10^3$ per well) were mixed at various ratios (11:1, 33:1, 100:1) in a final volume of 200 μl. After a 4 h incubation at 37° C., 50 μl of the cultured media were collected and the amount of LDH in the media was determined. The percentage of specific lysis was determined as 100×[(experimental release—effector spontaneous release target spontaneous release)/(target maximum release—target spontaneous release)].

Figure 6A:
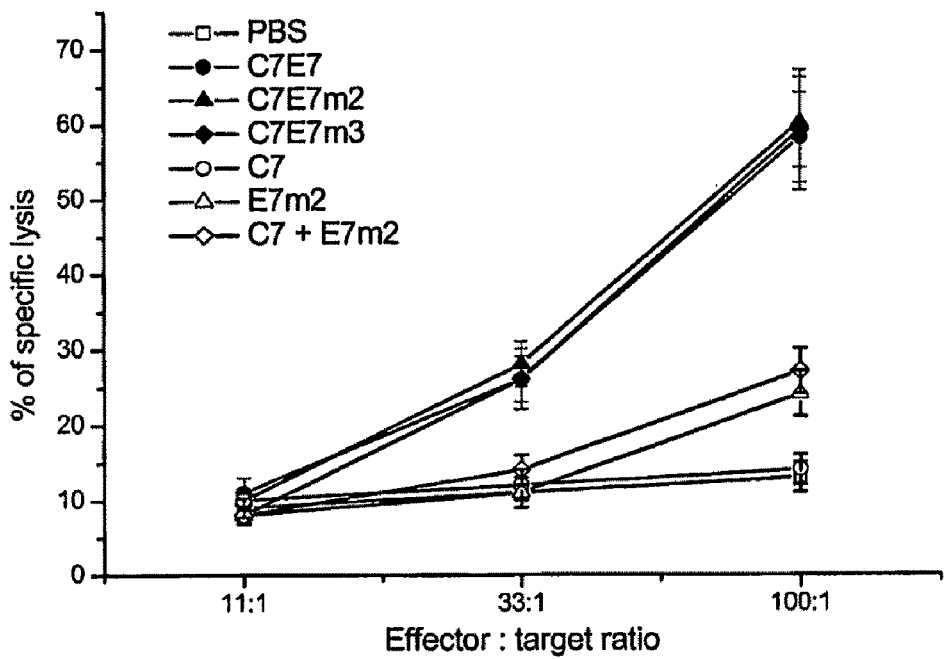
FIG. 6A compares mice immunized with fusion proteins comprising a full-length calreticulin immunostimulatory polypeptide.

In one study, the cytolytic activity of T-cells from mice administered the full-length calreticulin fused to wild-type or mutant HPV16 E7 antigens was investigated. FIG. 6A shows a comparison of cytolytic activity from effector cells of mice immunized with 300 μg of either C7E7, C7E7m2, C7E7m3, equalmolar amount of C7, E7m2, an admixture of C7 and E7m2 or PBS. The data indicate that the fusion protein of calreticulin and E7 (or its mutants) can stimulate specific CTL responses in mice, while the individual proteins were not as effective at stimulating a specific CTL response.

Figure 6B:
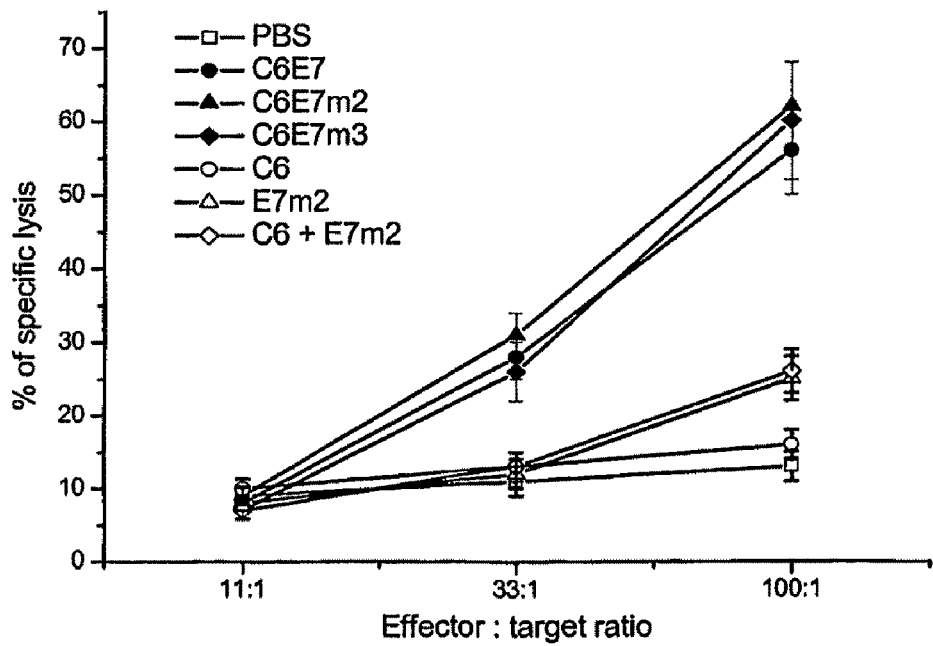
FIG. 6B compares mice immunized with fusion proteins comprising a N-terminal calreticulin fragment as an immunostimulatory polypeptide.

In a second study, the cytolytic activity of T-cells from mice administered the N-terminal domain (amino acids 18-366) of calreticulin fused to wild-type or mutant HPV16 E7 antigens was investigated. FIG. 6B shows a comparison of cytolytic activity from effector cells of mice immunized with 300 μg of either C6E7, C6E7m2, C6E7m3, equalmolar amount of C6, E7m2, an admixture of C6 and E7m2 or PBS. The results are similar to those shown in FIG. 6A and reveal that the N-terminal domain of calreticulin (C6) can substitute well for the full-length calreticulin in stimulating specific CTL responses.

Figure 6C:
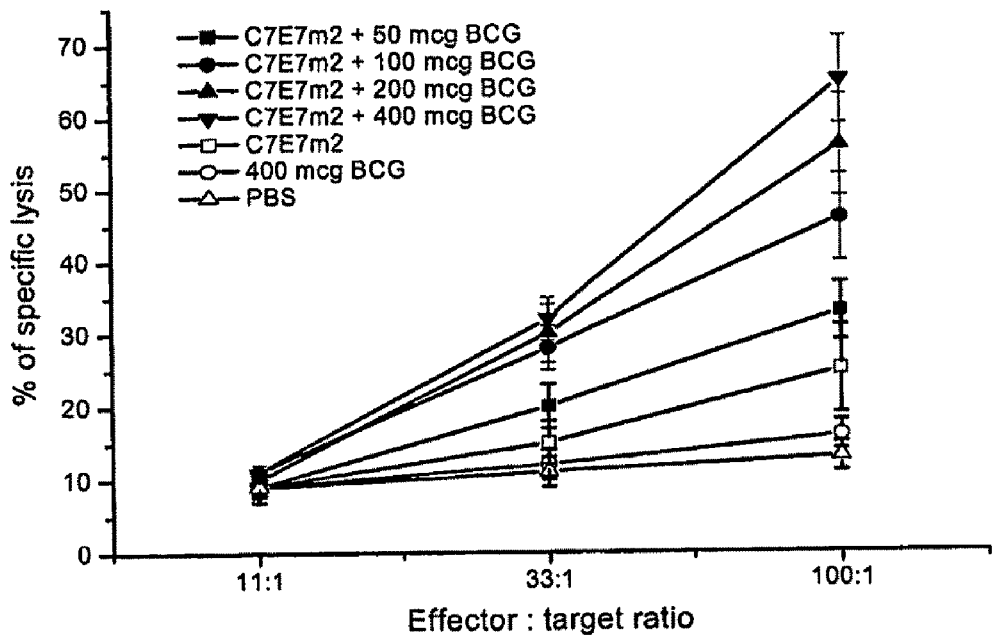
FIG. 6C compares mice immunized with fusion proteins comprising a full-length calreticulin immunostimulatory polypeptide in combination with BCG.

In a third study, the cytolytic activity of T-cells from mice administered the full-length calreticulin fused to wild-type or mutant HPV E7 antigens in combination with BCG was investigated. FIG. 6C shows a comparison of cytolytic activity from effector cells of mice immunized with 100 μg C7E7m2, 100 μg C7E7m2 in combination with different amounts of BCG (50 μg, 100 μg, 200 μg or 400 μg) or 400 μg BCG. The data show that BCG can cooperatively function with the HPV vaccines of this invention to stimulate cat responses.

Figure 6D:
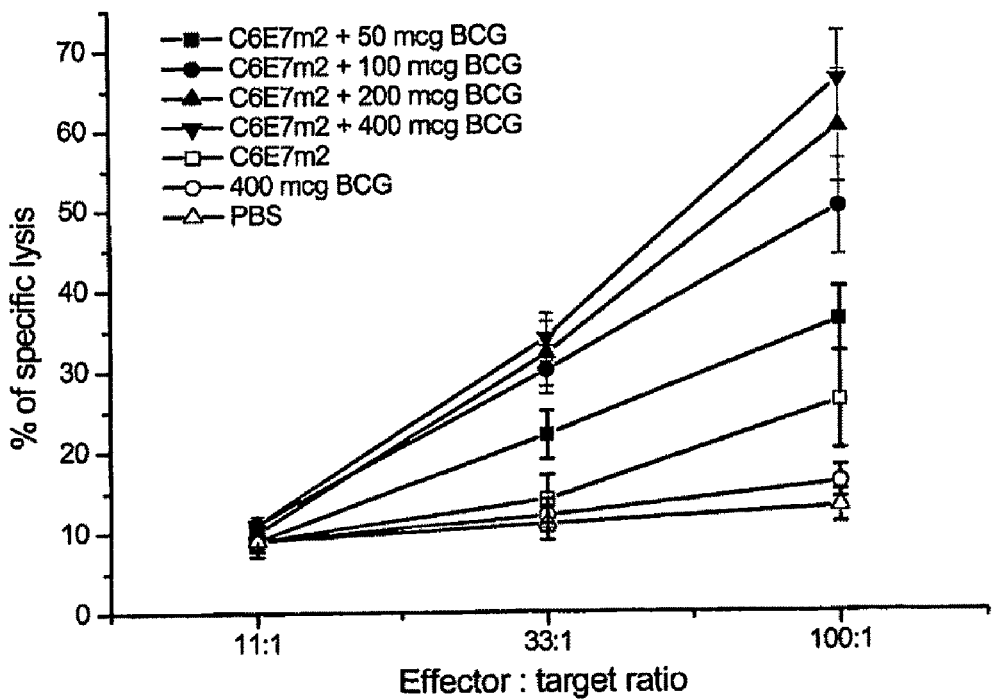
FIG. 6D compares mice immunized with fusion proteins comprising a N-terminal calreticulin fragment as an immunostimulatory polypeptide in combination with BCG.

In a fourth study, the cytolytic activity of T-cells from mice administered the N-terminal domain (amino acids 18-366) of calreticulin fused to wild-type or mutant HPV E7 antigens in combination with BCG was investigated. FIG. 6D shows a comparison of cytolytic activity from effector cells of mice immunized with 100 μg C6E7m2, 100 μg C6E7m2 in combination with different amounts of BCG (50 μg, 100 μg, 200 μg or 400 μg) or 400 μg BCG. The data show that BCG can cooperatively function with the HPV vaccines of this invention to stimulate CTL responses.

These studies indicate that the HPV vaccine compositions of the present invention are useful in stimulating an immune response, i.e., a cytotoxic T-lymphocyte response, against cells expressing the HPV16 E7 antigen. The results support the idea that the vaccine compositions may be used to direct an immune attack against HPV-induced cancer cells in humans. As such, the HPV fusion polypeptide compositions of the present invention are useful in methods of treating or preventing an HPV-related disease through the stimulation of an immune response.

Example 6

Effect of HPV Fusion Polypeptides of the Present Invention on Cytokine Production The ability of the HPV fusion polypeptides of the present invention to induce cytokine production was investigated by detecting IFN-γ production in an antibody capture ELISA. In these studies, C57BL/6 mice (three per group) were immunized subcutaneously in the scruff of the neck with various immunogens of the present invention (prepared as described in Example 1) or PBS and then boosted 14 days later with the same dose and regimen as the first vaccination. Fourteen days after the boost, pooled splenocytes were harvested and made into single-cell suspensions. Using 96-well flat-bottomed plates, $6 \times 10^5$ splenocytes were cultured using RPMI 1640 medium supplemented with 10% fetal calf serum (FCS; Hyclone, Logan, Utah) in a total volume of 0.2 ml. Triplicate cultures were restimulated for 72 h with either medium, 1.4 μM E7 or 1.4 μM HBsAg as an irrelevant antigen. Pooled supernatants from triplicate wells were collected by centrifugation and frozen at −80° C. until analyzed. IFN-γ content was measured by antibody capture ELISA according to manufacturer's instructions (PharMingen, San Diego, Calif.). IFN-γ content in culture supernatants was extrapolated from a curve generated using recombinant cytokines as standard (PharMingen).

Figure 7A:
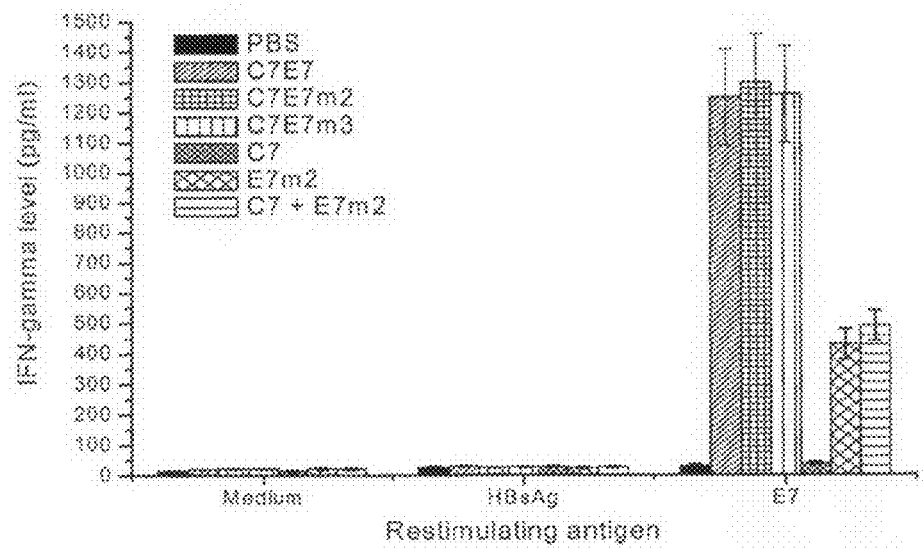
FIG. 7A compares mice immunized with fusion proteins comprising a full-length calreticulin immunostimulatory polypeptide.

In one study, cytokine production in splenocytes from mice administered the full-length calreticulin fused to wild-type or mutant HPV E7 antigens was investigated. FIG. 7A shows a comparison of IFN-γ production from splenocytes of mice immunized with 300 μg of either C7E7, C7E7m2, C7E7m3, equalmolar amount of C7, E7m2, an admixture of C7 and E7m2 or PBS. The data indicate that the fusion protein of calreticulin and E7 (or its mutants) can stimulate Th1-type cytokine release in mice, while the individual proteins were not as effective at stimulating cytokine release.

Figure 7B:
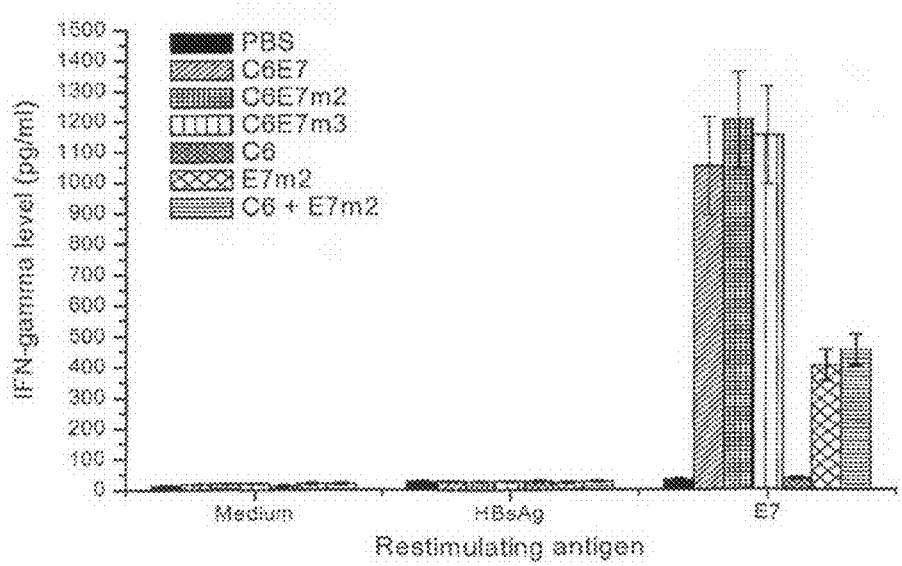
FIG. 7B compares mice immunized with fusion proteins comprising a N-terminal calreticulin fragment as an immunostimulatory polypeptide.

In a second study, cytokine production in splenocytes from mice administered the N-terminal domain (amino acids 18-366) of calreticulin fused to wild-type or mutant HPV E7 antigens was investigated. FIG. 7B shows a comparison of IFN-γ production from splenocytes of mice immunized with 300 μg of either C6E7, C6E7m2, C6E7m3, equalmolar amount of C6, E7m2, an admixture of C6 and E7m2 or PBS. The results are similar to those shown in FIG. 7A and reveal that the N-terminal domain of calreticulin (C6) can substitute well for the full-length calreticulin in stimulating Th1-type cytokine releases.

Figure 7C:
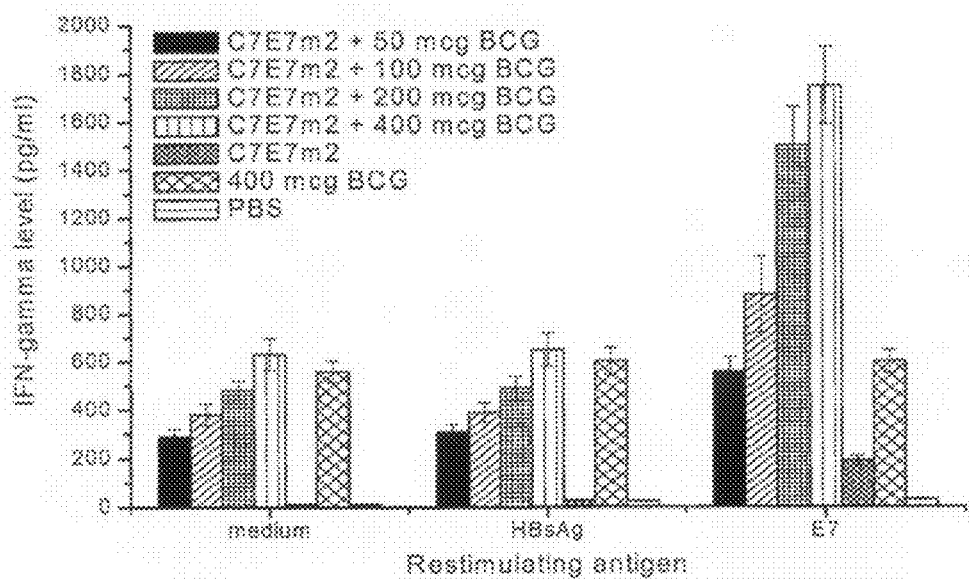
FIG. 7C compares mice immunized with fusion proteins comprising a full-length calreticulin immunostimulatory polypeptide in combination with BCG.

In a third study, cytokine production in splenocytes from mice administered the full-length calreticulin fused to wild-type or mutant HPV E7 antigens in combination with BCG was investigated. FIG. 7C shows a comparison of IFN-γ production from splenocytes of mice immunized with 100 μg C7E7m2, 100 μg C7E7m2 in combination with different amounts of BCG (50 μg, 100 μg, 200 μg or 400 μg) or 400 μg BCG. The data show that BCG can co-operatively function with the HPV fusion polypeptide vaccines of the invention to stimulate Th1-type cytokine production.

Figure 7D:
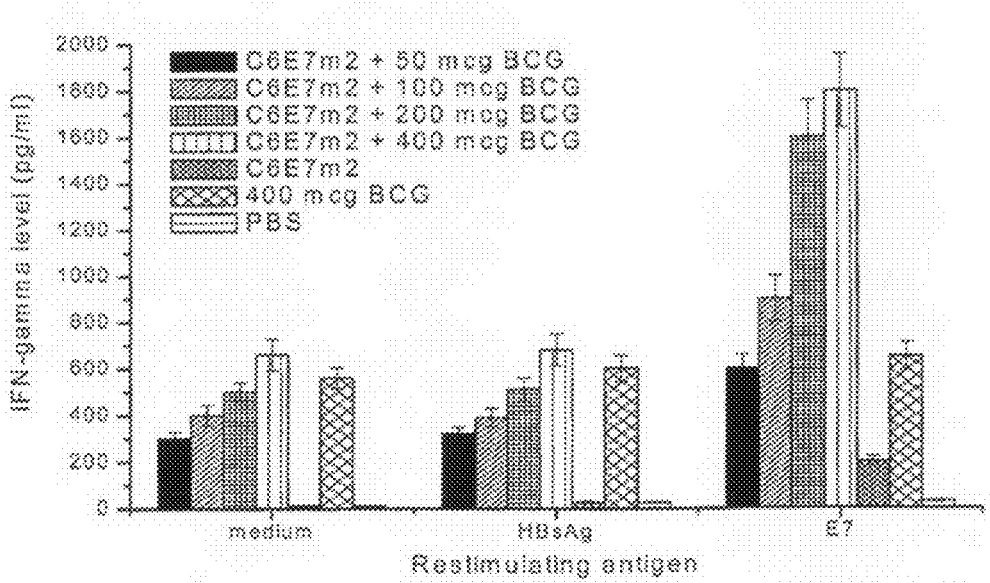
FIG. 7D compares mice immunized with fusion proteins comprising a N-terminal calreticulin fragment as an immunostimulatory polypeptide in combination with BCG.

In a fourth study, cytokine production in splenocytes from mice administered the N-terminal domain (amino acids 18-366 of SEQ ID NO:2) of calreticulin fused to wild-type or mutant HPV 16 E7 antigens in combination with BCG was investigated. FIG. 7D shows a comparison of IFN-γ production from splenocytes of mice immunized with 100 µg C6E7m2, 100 µg C6E7m2 in combination with different amounts of BCG (50 µg, 100 µg, 200 µg or 400 µg) or 400 µg BCG. The data show that BCG can co-operatively function with the HPV fusion polypeptide vaccines of the invention to stimulate Th1-type cytokine production.

These studies indicate that the HPV vaccine compositions of the present invention are useful in stimulating a specific immune response—cytokine production—when challenged with the HPV E7 antigen. The results support the idea that the vaccine compositions may be used to direct an immune attack against HPV-induced cancer cells in humans. As such, the HPV fusion polypeptide compositions of the present invention are useful in methods of treating or preventing an HPV-related disease through the stimulation of an immune response.

Example 7

Therapeutic and Prophylatic Vaccination of Human Subjects (Prophetic)

The HPV fusion polypeptides of the present invention can be used in treatment of HPV infections and diseases caused thereby. Specifically, the invention provides for both prophylactic and therapeutic methods of treating a subject at risk of (or susceptible to) a disorder or having a disorder associated with a HPV infection. Administration of a prophylactic HPV fusion polypeptide can occur prior to the manifestation of symptoms characteristic of the infection, such that a disease or condition is prevented or, alternatively, delayed in its progression. In therapeutic applications, HPV fusion polypeptides of the present invention are administered to a subject suspected of, or already suffering from, a HPV infection. An amount adequate to accomplish therapeutic or prophylactic treatment is defined as a therapeutically- or prophylactically-effective dose.

In this Example, human subjects having an HPV-related disease, e.g. cervical cancer, are administered the vaccine compositions of the present invention. HPV fusion polypeptides are prepared as described in Example 1. An vaccine comprising C6E7m2 or C7E7m3 (with or without BCG as an adjuvant) is administered to a human subject having an abnormal Papanikolaou test (pap smear) result. The pap test checks for changes in the cells of the cervix and can detect abnormal cervical cells. As such, the pap test is an indicator of subjects having or at risk for having an HPV-related disease. After treatment, patient condition is monitored for occurrence of tumors and/or reduction in tumor size. A successful treatment using the vaccine compositions of the invention is characterized by the prevention or delay in the onset of tumors or a reduction in tumor size in the subject compared to a normal subject (i.e., one without viral infection).

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

Other embodiments are set forth within the following claims.

---

What is claimed is:

1. A vaccine composition comprising a fusion protein of an immunostimulatory polypeptide and a mutant HPV antigen, wherein
    the immunostimulatory polypeptide is calreticulin or a fragment of calreticulin comprising amino acids 18-180 of SEQ ID NO:2; and
    the mutant HPV antigen is an HPV16 E7 polypeptide comprising substitutions in the cysteine residues corresponding to cysteine-59 and cysteine-68 of SEQ ID NO:1.

2. The vaccine composition of claim 1, wherein the substitutions are C59S and C68V.

3. The vaccine composition of claim 1, wherein the E7 polypeptide further comprises a substitution at the cysteine residue corresponding to cysteine-24 of SEQ ID NO:1.

4. The vaccine composition of claim 3, wherein the substitutions are C24V, C59S, and C68V.

5. The vaccine composition of claim 1, wherein the fusion protein is selected from the group consisting of: SEQ ID NOS: 6, 8, 12, and 14.

6. The vaccine composition of claim 1 further comprising BCG as an adjuvant.

7. A method for the treatment or prevention of a human papilloma virus related disease, comprising administering to a subject an effective amount of a fusion protein comprising an immunostimulatory polypeptide and a mutant HPV antigen, wherein the immunostimulatory polypeptide is calreticulin or a fragment of calreticulin comprising amino acids 18-180 of SEQ ID NO:2; and the mutant HPV antigen is an E7 polypeptide comprising substitutions in the cysteine residues corresponding to cysteine-59 and cysteine-68 of SEQ ID NO:1, thereby treating or preventing the HPV-related disease in the subject.

8. The method of claim 7, wherein the human papilloma virus related disease is selected from the group consisting of: cervical cancer, anal intraepithelial neoplasia, cervical intraepithelial neoplasia, anogenital warts, recurrent respiratory tract papilloma and vaginal intraepithelial neoplasia.

9. The method of claim 7, wherein the fusion protein is administered prior to the occurrence of a human papilloma virus related disease.

10. The method of claim 7, wherein the substitutions are C59S and C68V.

11. The method of claim 7, wherein the E7 polypeptide further comprises a substitution at the cysteine residue corresponding to cysteine 24 of SEQ ID NO: 1.

12. The method of claim 11, wherein the substitutions are C24V, C59S, and C68V.

13. The method of claim 7, wherein the fusion protein is selected from the group consisting of: SEQ ID NOS: 6, 8, 12, and 14.

14. The method of claim 7 further comprising the step of administering an effective amount of BCG as an adjuvant.

* * * * *